(12) United States Patent
Kahvejian et al.

(10) Patent No.: US 11,208,475 B1
(45) Date of Patent: Dec. 28, 2021

(54) METHODS AND COMPOSITIONS FOR TREATING INFLAMMATORY OR AUTOIMMUNE DISEASES OR CONDITIONS USING SEROTONIN RECEPTOR ACTIVATORS

(71) Applicant: Flagship Pioneering Innovations V, Inc., Cambridge, MA (US)

(72) Inventors: Avak Kahvejian, Lexington, MA (US); Jordi Mata-Fink, Baltimore, MD (US); Jonathan Barry Hurov, Bedford, MA (US); Chengyi Jenny Shu, Cambridge, MA (US); George Huck Neubauer, Malden, MA (US); Manuel Andreas Fankhauser, Bern (CH); Julian Alexander Stanley, Oregon City, OR (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 16/262,474

(22) Filed: Jan. 30, 2019

Related U.S. Application Data

(60) Provisional application No. 62/623,629, filed on Jan. 30, 2018.

(51) Int. Cl.
| | |
|---|---|
| *C07K 16/24* | (2006.01) |
| *A61P 37/06* | (2006.01) |
| *A61K 31/137* | (2006.01) |
| *A61K 9/00* | (2006.01) |
| *A61K 31/506* | (2006.01) |
| *A61K 45/06* | (2006.01) |

(52) U.S. Cl.
CPC .......... *C07K 16/244* (2013.01); *A61K 9/0019* (2013.01); *A61K 31/137* (2013.01); *A61K 31/506* (2013.01); *A61P 37/06* (2018.01); *A61K 45/06* (2013.01)

(58) Field of Classification Search
None
See application file for complete search history.

(56) References Cited

U.S. PATENT DOCUMENTS

| | | | |
|---|---|---|---|
| 2007/0027178 A1* | 2/2007 | Lee | C07D 471/04 514/291 |
| 2009/0286760 A1* | 11/2009 | Chen | A61K 31/405 514/165 |
| 2012/0190751 A1* | 7/2012 | Palmqvist | A61K 31/155 514/632 |
| 2013/0267500 A1* | 10/2013 | Anderson | A61K 31/55 514/217.01 |
| 2014/0350064 A1* | 11/2014 | Chen | A61P 3/04 514/415 |

FOREIGN PATENT DOCUMENTS

| | | | | |
|---|---|---|---|---|
| WO | WO 2007/10075 | * | 9/2007 | ............. A61K 31/00 |
| WO | WO 2012030953 | * | 3/2012 | ............. A61K 31/00 |
| WO | WO-2018/022664 A1 | | 2/2018 | |

OTHER PUBLICATIONS

Krishnadas et al., Journal of Medical Case Reports 2011, 5:112; 5 pages total (Year: 2011).*
Definition of biologic response modifier therapy at NIH National Cancer Institute website: https://www.cancer.gov/publications/dictionaries/cancer-terms/def/biological-response-modifier-therapy; downloaded Dec. 18, 2020 (Year: 2020).*
Vivian P. Bykerk, information on inflammatory arthritis downloaded Dec. 18, 2020 from the website: https://www.hss.edu/conditions_understanding-inflammatory-arthritis-an-introduction.asp; 14 pages total (Year: 2020).*
An archived (Jul. 2016) website from the Mayo Clinic (The Wayback Machine—https://web.archive.org/web/20160713233549/http://www.mayoclinic.org:80/drugs-suppl . . . ); 15 pages total (Year: 2016).*
De las Casas-Engel et al., "Serotonin skews human macrophage polarization through HTR2B and HTR7," J Immunol. 190(5):2301-10 (2013) (11 pages).
Eugene-Olsen et al., "Serotonin modulates immune function in T cells from HIV-seropositive subjects," Clin Immunol Immunopathol. 84(2):115-21 (1997).
Guseva et al., "Serotonin 5-HT7 receptor is critically involved in acute and chronic inflammation of the gastrointestinal tract," Inflamm Bowel Dis. 20(9):1516-29 (2014).
Holst et al., "The serotonin receptor 5-HT7R regulates the morphology and migratory properties of dendritic cells," J Cell Sci. 128(15):2866-80 (2015).
León-Ponte et al., "Serotonin provides an accessory signal to enhance T-cell activation by signaling through the 5-HT7 receptor," Blood. 109(8):3139-46 (2007) (9 pages).
Li et al., "Serotonin activates dendritic cell function in the context of gut inflammation," Am J Pathol. 178(2):662-71 (2011).
Magrini et al., "Serotonin-mediated tuning of human helper T cell responsiveness to the chemokine CXCL12," PLoS One. 6(8):e22482 (2011) (10 pages).
Mikulski et al., "Serotonin activates murine alveolar macrophages through 5-HT2C receptors," Am J Physiol Lung Cell Mol Physiol. 299(2):L272-80 (2010).

(Continued)

*Primary Examiner* — Christina M Borgeest
(74) *Attorney, Agent, or Firm* — Clark & Elbing LLP

(57) ABSTRACT

The present invention provides methods for treating inflammatory or autoimmune diseases or conditions using serotonin receptor activators, such as serotonin receptor activating antibodies, among others. The invention also features compositions containing serotonin receptor activators, methods of diagnosing patients with a serotonin receptor-associated inflammatory or autoimmune disease or condition, and methods of predicting the response of an inflammatory or autoimmune disease or condition in a subject to treatment with serotonin receptor activators.

10 Claims, No Drawings

(56) References Cited

OTHER PUBLICATIONS

Müller et al., "5-hydroxytryptamine modulates migration, cytokine and chemokine release and T-cell priming capacity of dendritic cells in vitro and in vivo," PLoS One. 4(7):e6453 (2009) (8 pages).

Shajib et al., "Interleukin 13 and serotonin: linking the immune and endocrine systems in murine models of intestinal inflammation," PLoS One. 8(8):e72774 (2013) (12 pages).

Young et al., "Serotonin regulation of T-cell subpopulations and of macrophage accessory function," Immunology. 84(1):148-52 (1995).

Young et al., "Stimulation of splenic T-lymphocyte function by endogenous serotonin and by low-dose exogenous serotonin," Immunology. 80(3):395-400 (1993).

* cited by examiner

METHODS AND COMPOSITIONS FOR TREATING INFLAMMATORY OR AUTOIMMUNE DISEASES OR CONDITIONS USING SEROTONIN RECEPTOR ACTIVATORS

CROSS-REFERENCE

This application claims the benefit of U.S. Provisional Application No. 62/623,629, filed Jan. 30, 2018, which is incorporated herein by reference in its entirety.

BACKGROUND

Epidemiological data provide evidence of a steady rise in inflammatory and autoimmune disease throughout westernized societies over the last decades. The net % increase/year incidence and prevalence of autoimmune diseases worldwide have been reported to be 19% and 12%, respectively (Lerner et al., Intl J Celiac Dis. 3:151, 2015). Thus, there remains a need in the field for treatments of immune conditions such as autoimmune disease.

SUMMARY OF THE INVENTION

The present invention provides methods for treating inflammatory or autoimmune diseases or conditions using serotonin receptor activators, such as serotonin receptor activating antibodies, among others. The invention also features compositions containing serotonin receptor activators, methods of diagnosing patients with a serotonin receptor-associated inflammatory or autoimmune disease or condition, and methods of predicting the response of an inflammatory or autoimmune disease or condition in a subject to treatment with serotonin receptor activators, such as HTR1F, HTR2B, HTR2C, HTR3A, HRT6, or HTR7 activators.

In a first aspect, the invention provides a method of modulating an immune response in a subject in need thereof by administering to the subject an effective amount of a serotonin receptor activator.

In another aspect, the invention provides a method of modulating an immune response in a subject in need thereof by contacting an immune cell, spleen, lymph node, secondary lymphoid organ, tertiary lymphoid organ, barrier tissue, skin, gut, airway, or wound with an effective amount of a serotonin receptor activator.

In another aspect, the invention provides a method of modulating an immune cell activity in a subject in need thereof by contacting an immune cell, spleen, lymph node, secondary lymphoid organ, tertiary lymphoid organ, barrier tissue, skin, gut, airway, or wound with an effective amount of a serotonin receptor activator.

In a first aspect, the invention provides a method of treating a subject with inflammatory or autoimmune disease or condition, by administering to the subject an effective amount of a serotonin receptor-specific activator, such as a serotonin receptor-specific activator.

In another aspect, the invention provides a method of treating a subject with an inflammatory or autoimmune disease or condition by contacting an immune cell, spleen, lymph node, secondary lymphoid organ, tertiary lymphoid organ, barrier tissue, skin, gut, airway, or wound with an effective amount of a serotonin receptor-specific activator.

In another aspect, the invention provides a method of treating a subject identified as having an inflammatory or autoimmune disease or condition by administering to the subject an effective amount of a serotonin receptor-specific activator, such as a serotonin receptor-specific activator.

In another aspect, the invention provides a method of treating a subject identified as having an inflammatory or autoimmune disease or condition by contacting an immune cell, spleen, lymph node, secondary lymphoid organ, tertiary lymphoid organ, barrier tissue, skin, gut, airway, or wound with an effective amount of a serotonin receptor-specific activator.

In another aspect, the invention provides a method of decreasing levels of one or more pro-inflammatory cytokine in a subject in need thereof by administering to the subject an effective amount of a serotonin receptor activator. In some embodiments, the subject is a subject with a serotonin receptor-associated inflammatory or autoimmune disease or condition. In some embodiments, the one or more pro-inflammatory cytokine includes interleukin-8 (IL-8). In some embodiments, the method further includes determining the level of one or more pro-inflammatory cytokine after administration of the serotonin receptor activator.

In another aspect, the invention provides a method of decreasing levels of one or more cytokine in a subject in need thereof by administering to the subject an effective amount of a serotonin receptor activator. In some embodiments, the subject is a subject with a serotonin receptor-associated inflammatory or autoimmune disease or condition. In some embodiments, the one or more cytokine includes IL-8. In some embodiments, the method further includes determining the level of one or more cytokine after administration of the serotonin receptor activator.

In some embodiments of any of the above aspects, the inflammatory or autoimmune disease or condition is serotonin receptor-associated inflammatory or autoimmune disease or condition.

In another aspect, the invention provides a method of treating a subject with an inflammatory or autoimmune disease or condition by: a) identifying a subject with serotonin receptor-associated inflammatory or autoimmune disease or condition; and b) administering to the subject an effective amount of a serotonin receptor activator.

In another aspect, the invention provides a method of treating a subject with an inflammatory or autoimmune disease or condition by: a) identifying a subject with serotonin receptor-associated inflammatory or autoimmune disease or condition; and b) contacting an immune cell, spleen, lymph node, secondary lymphoid organ, tertiary lymphoid organ, barrier tissue, skin, gut, airway, or wound with an effective amount of a serotonin receptor activator.

In another aspect, the invention provides a method of treating a subject with a serotonin receptor-associated inflammatory or autoimmune disease or condition by administering to the subject an effective amount of a serotonin receptor activator.

In another aspect, the invention provides a method of treating a subject with a serotonin receptor-associated inflammatory or autoimmune disease or condition by contacting an immune cell, spleen, lymph node, secondary lymphoid organ, tertiary lymphoid organ, barrier tissue, skin, gut, airway, or wound with an effective amount of a serotonin receptor activator.

In some embodiments of any of the above aspects, the method includes contacting an immune cell with an effective amount of a serotonin receptor activator. In some embodiments of any of the above aspects, the method includes contacting the spleen with an effective amount of a serotonin receptor activator. In some embodiments of any of the above aspects, the method includes contacting a lymph node with an effective amount of a serotonin receptor activator. In some embodiments of any of the above aspects, the method includes contacting a secondary lymphoid organ with an effective amount of a serotonin receptor activator. In some embodiments of any of the above aspects, the method includes contacting a tertiary lymphoid organ with an effective amount of a serotonin receptor activator. In some embodiments of any of the above aspects, the method includes contacting a barrier tissue with an effective amount of a serotonin receptor activator. In some embodiments of any of the above aspects, the method includes contacting the skin with an effective amount of a serotonin receptor activator. In some embodiments of any of the above aspects, the method includes contacting the gut with an effective amount of a serotonin receptor activator. In some embodiments of any of the above aspects, the method includes contacting an airway with an effective amount of a serotonin receptor activator. In some embodiments of any of the above aspects, the method includes contacting a wound with an effective amount of a serotonin receptor activator.

In some embodiments of any of the above aspects, the method includes contacting an immune cell with an effective amount of a serotonin receptor activator that increases expression or activity of one or more serotonin receptors (e.g., one or more serotonin receptors listed in Table 1, e.g., HTR1F, HTR2B, HTR2C, HTR3A, HRT6, and/or HTR7) in the immune cell.

In some embodiments of any of the above aspects, the method includes modulating an immune cell activity.

In some embodiments of any of the above aspects, the immune cell activity is immune cell migration, proliferation, recruitment, lymph node homing, lymph node egress, differentiation, activation, polarization, cytokine production, degranulation, maturation, antibody-dependent cell-mediated cytotoxicity (ADCC), antibody-dependent cellular phagocytosis (ADCP), antigen presentation, or serotonin receptor expression.

In some embodiments of any of the above aspects, immune cell lymph node homing, and/or serotonin receptor expression is increased. In some embodiments of any of the above aspects, immune cell migration, proliferation, recruitment, lymph node egress, differentiation, activation, polarization, cytokine production, degranulation, maturation, ADCC, ADCP, and/or antigen presentation is decreased. In some embodiments, polarization toward a pro-inflammatory state (e.g., an M1 phenotype) is decreased. In some embodiments, polarization toward an anti-inflammatory state (e.g., an M2 phenotype) is increased.

In another aspect, the invention provides a method of decreasing macrophage production of one or more pro-inflammatory cytokine by contacting a macrophage with an effective amount of a serotonin receptor activator. In some embodiments, the macrophage is a macrophage expressing one or more serotonin receptors (e.g., one or more serotonin receptors listed in Table 1, e.g., HTR1F, HTR2B, HTR2C, HTR3A, HRT6, and/or HTR7). In some embodiments, the one or more pro-inflammatory cytokine includes IL-8.

In another aspect, the invention provides a method of modulating (e.g., decreasing) macrophage cytokine production in a subject in need thereof, by contacting a macrophage with an effective amount of a serotonin receptor activator.

In another aspect, the invention provides a method of modulating (e.g., decreasing) macrophage cytokine production in a subject in need thereof by administering to the subject an effective amount of a serotonin receptor activator.

In some embodiments of any of the above aspects, macrophage cytokine production of pro-inflammatory cytokines is decreased.

In another aspect, the invention provides a method of decreasing pro-inflammatory cytokine levels in a subject in need thereof by administering to the subject an effective amount of a serotonin receptor activator.

In some embodiments of any of the above methods, the pro-inflammatory cytokine is IL-8.

In another aspect, the invention provides a method of modulating macrophage polarization in a subject in need thereof by administering to the subject an effective amount of a serotonin receptor activator. In some embodiments, polarization toward a pro-inflammatory state (e.g., an M1 phenotype) is decreased. In some embodiments, polarization toward an anti-inflammatory state (e.g., an M2 phenotype) is increased.

In some embodiments of any of the above aspects, the serotonin receptor-associated inflammatory or autoimmune disease or condition is associated with decreased expression of one or more serotonin receptors (e.g., one or more serotonin receptors listed in Table 1, e.g., HTR1F, HTR2B, HTR2C, HTR3A, HRT6, and/or HTR7) in immune cells (e.g., macrophages or T cells, e.g., CD4+ or CD8+ T cells).

In some embodiments of any of the above aspects, the method further includes contacting an immune cell isolated from the subject with a serotonin receptor activator and evaluating the response of the immune cell prior to administration of the serotonin receptor activator.

In another aspect, the invention provides a method of treating a subject having an inflammatory or autoimmune disease or condition, the method including the steps of a) contacting an immune cell isolated from the subject with a serotonin receptor activator and evaluating a response of the immune cell; and b) administering to the subject an effective amount of a serotonin receptor activator if the response of the immune cell is modulated by the serotonin receptor activator (e.g., if the serotonin receptor activator decreases immune cell migration, proliferation, recruitment, lymph node egress, differentiation, activation, polarization, cytokine production, degranulation, maturation, ADCC, ADCP, and/or antigen presentation).

In another aspect, the invention provides a method of treating a subject having an inflammatory or autoimmune disease or condition, the method including the steps of a) contacting an immune cell isolated from the subject with a serotonin receptor activator and evaluating a response of the immune cell; and b) contacting an immune cell, spleen, lymph node, secondary lymphoid organ, tertiary lymphoid organ, barrier tissue, skin, gut, airway, or wound with an effective amount of a serotonin receptor activator if the response of the immune cell is modulated by the serotonin receptor activator (e.g., if the serotonin receptor activator decreases immune cell migration, proliferation, recruitment, lymph node egress, differentiation, activation, polarization, cytokine production, degranulation, maturation, ADCC, ADCP, and/or antigen presentation).

In another aspect, the invention provides a method of treating a subject having an inflammatory or autoimmune disease or condition, the method including the steps of a) contacting an immune cell isolated from the subject with a serotonin receptor activator and evaluating a response of the immune cell; and b) administering to the subject an effective amount of a serotonin receptor activator.

In another aspect, the invention provides a method of predicting the response of an inflammatory or autoimmune disease or condition in a subject to treatment with a serotonin receptor activator by contacting an immune cell isolated from the subject with a serotonin receptor activator and evaluating the response of the immune cell.

In some embodiments of any of the above aspects, the evaluating includes assessing immune cell migration, immune cell proliferation, immune cell recruitment, immune cell lymph node homing, immune cell lymph node egress, immune cell differentiation, immune cell activation, immune cell polarization, immune cell cytokine production (e.g., IL-8 production), immune cell degranulation, immune cell maturation, immune cell ADCC, immune cell ADCP, immune cell antigen presentation, or immune cell serotonin receptor expression.

In another aspect, the invention provides a method of predicting the response of an inflammatory or autoimmune disease or condition in a subject to treatment with a serotonin receptor activator by: a) isolating an immune cell from the subject; b) measuring the expression of one or more serotonin receptors (e.g., a serotonin receptor listed in Table 1, e.g., HTR1F, HTR2B, HTR2C, HTR3A, HRT6, and/or HTR7) in the immune cell; and c) comparing serotonin receptor expression in the immune cell to a reference, wherein decreased expression of one or more serotonin receptors in the immune cell as compared to the reference indicates that the subject will respond to treatment with a serotonin receptor activator.

In another aspect, the invention provides a method of determining if an immune cell expresses a functional serotonin receptor by contacting the immune cell with a serotonin receptor agonist and evaluating pro-inflammatory cytokine production (e.g., IL-8 release from the immune cell). In some embodiments, a decrease in pro-inflammatory cytokine production (e.g., IL-8 production) indicates that the immune cell expresses a functional serotonin receptor.

In some embodiments of any of the above aspects, the method further includes contacting the immune cell with a serotonin receptor activator.

In another aspect, the invention provides a method of characterizing an inflammatory or autoimmune disease or condition in a subject by: a) isolating an immune cell from the subject; b) measuring the expression of one or more serotonin receptors (e.g., a serotonin receptor listed in Table 1, e.g., HTR1F, HTR2B, HTR2C, HTR3A, HRT6, and/or HTR7) in the immune cell; and c) comparing serotonin receptor expression in the immune cell to a reference, wherein decreased expression of one or more serotonin receptors in the immune cell as compared to the reference indicates that the subject has a serotonin receptor-associated inflammatory or autoimmune disease or condition.

In another aspect, the invention provides a method of identifying a subject as having a serotonin receptor-associated inflammatory or autoimmune disease or condition by: a) isolating an immune cell from the subject; b) measuring the expression of one or more serotonin receptors (e.g., a serotonin receptor listed in Table 1, e.g., HTR1F, HTR2B, HTR2C, HTR3A, HRT6, and/or HTR7) in the immune cell; and c) comparing serotonin receptor expression in the immune cell to a reference, wherein decreased expression of one or more serotonin receptors in the immune cell as compared to the reference indicates that the subject has a serotonin receptor-associated inflammatory or autoimmune disease or condition.

In some embodiments of any of the above aspects, the method further includes providing a serotonin receptor activator suitable for administration to the subject. In some embodiments of any of the above aspects, the method further includes administering to the subject an effective amount of a serotonin receptor activator.

In some embodiments of any of the above aspects, the serotonin receptor activator is a serotonin receptor-specific activator.

In some embodiments of any of the above aspects, the serotonin receptor activator or serotonin receptor-specific activator is a serotonin receptor function activator.

In some embodiments of any of the above aspects, the serotonin receptor activator or serotonin receptor-specific activator is a serotonin receptor signaling activator.

In some embodiments of any of the above aspects, the serotonin receptor activator or serotonin receptor-specific activator increases serotonin receptor expression or activity.

In some embodiments of any of the above aspects, the inflammatory or autoimmune disease or condition is allergy, asthma, inflammatory bowel disease (IBD), Crohn's, Ulcerative Colitis, dermatitis, fibrosis, wound-healing, systemic lupus erythematosus (SLE), small vessel vasculitis, or rheumatoid arthritis.

In some embodiments of any of the above aspects, the inflammatory or autoimmune disease or condition is an IL-8 associated inflammatory or autoimmune disease or condition. In some embodiments, the IL-8-associated inflammatory or autoimmune disease or condition is collagen-induced arthritis, coxsackie myocarditis, glomerulonephritis, pemphigus vulgaris, psoriasis, rheumatoid arthritis, uveitis, scleroderma, dermatitis, Crohn's disease, inclusion body myositis, juvenile myositis, or idiopathic pulmonary fibrosis.

In some embodiments of any of the above aspects, the inflammatory or autoimmune disease or condition is a serotonin receptor-associated inflammatory or autoimmune disease or condition.

In some embodiments of any of the above aspects, the serotonin receptor activator or serotonin receptor-specific activator is administered locally. In some embodiments of any of the above aspects, the serotonin receptor activator or serotonin receptor-specific activator is administered to or near a lymph node, the spleen, a secondary lymphoid organ, a tertiary lymphoid organ, barrier tissue, skin, the gut, an airway, or a wound. In some embodiments of any of the above aspects, the serotonin receptor activator or serotonin receptor-specific activator is administered to or near a lymph node. In some embodiments of any of the above aspects, the serotonin receptor activator or serotonin receptor-specific activator is administered to or near the spleen. In some embodiments of any of the above aspects, the serotonin receptor activator or serotonin receptor-specific activator is administered to or near a secondary lymphoid organ. In some embodiments of any of the above aspects, the serotonin receptor activator or serotonin receptor-specific activator is administered to or near a tertiary lymphoid organ. In some embodiments of any of the above aspects, the serotonin receptor activator or serotonin receptor-specific activator is administered to or near a barrier tissue. In some embodiments of any of the above aspects, the serotonin receptor activator or serotonin receptor-specific activator is administered to or near the skin. In some embodiments of any of the above aspects, the serotonin receptor activator or serotonin receptor-specific activator is administered to or near the gut. In some embodiments of any of the above aspects, the serotonin receptor activator or serotonin receptor-specific activator is administered to or near an airway. In some embodiments of any of the above aspects, the serotonin receptor activator or serotonin receptor-specific activator is administered to or near a wound.

In some embodiments of any of the above aspects, the serotonin receptor activator or serotonin receptor-specific activator is administered systemically.

In some embodiments of any of the above aspects, the method further includes administering a second therapeutic agent.

In some embodiments of any of the above aspects, the serotonin receptor activator or serotonin receptor-specific activator decreases the development of high endothelial venules (HEVs) or tertiary lymphoid organs (TLOs), decreases immune cell migration, decreases immune cell proliferation, decreases immune cell recruitment, increases immune cell lymph node homing, decreases immune cell lymph node egress, decreases immune cell differentiation, decreases immune cell activation, decreases immune cell polarization, decreases immune cell cytokine production, decreases immune cell degranulation, decreases immune cell maturation, decreases immune cell ADCC, decreases immune cell ADCP, decreases immune cell antigen presentation, decreases immune cell serotonin receptor expression (e.g., expression of one or more serotonin receptors listed in Table 1, e.g., HTR1F, HTR2B, HTR2C, HTR3A, HRT6, and/or HTR7), decreases inflammation, decreases auto-antibody levels, increases organ function, or decreases rate or number of relapses or flare-ups.

In some embodiments of any of the above aspects, the method further includes measuring one or more of the development of HEVs or TLOs, immune cell migration, immune cell proliferation, immune cell recruitment, immune cell lymph node homing, immune cell lymph node egress, immune cell differentiation, immune cell activation, immune cell polarization, immune cell cytokine production, immune cell degranulation, immune cell maturation, immune cell ADCC, immune cell ADCP, or immune cell antigen presentation, symptoms of an autoimmune or inflammatory condition, inflammation, auto-antibody levels, organ function, the rate or number of relapses or flare-ups, viral load, or immune cell serotonin receptor expression (e.g., expression of one or more serotonin receptors listed in Table 1, e.g., HTR1F, HTR2B, HTR2C, HTR3A, HRT6, and/or HTR7) before administration of the serotonin receptor activator or serotonin receptor-specific activator.

In some embodiments of any of the above aspects, the method further includes measuring one or more of development of HEVs or TLOs, immune cell migration, immune cell proliferation, immune cell recruitment, immune cell lymph node homing, immune cell lymph node egress, immune cell differentiation, immune cell activation, immune cell polarization, immune cell cytokine production, immune cell degranulation, immune cell maturation, immune cell ADCC, immune cell ADCP, or immune cell antigen presentation, symptoms of an autoimmune or inflammatory condition, inflammation, auto-antibody levels, organ function, the rate or number of relapses or flare-ups, viral load, or immune cell serotonin receptor expression (e.g., expression of one or more serotonin receptors listed in Table 1, e.g., HTR1F, HTR2B, HTR2C, HTR3A, HRT6, and/or HTR7) after administration of the serotonin receptor activator or serotonin receptor-specific activator.

In some embodiments of any of the above aspects, the serotonin receptor activator or serotonin receptor-specific activator is administered in an amount sufficient to decrease the development of HEVs or TLOs, decrease immune cell migration, decrease immune cell proliferation, decrease immune cell recruitment, increase immune cell lymph node homing, decrease immune cell lymph node egress, decrease immune cell differentiation, decrease immune cell activation, decrease immune cell polarization, decrease immune cell cytokine production, decrease immune cell degranulation, decrease immune cell maturation, decrease immune cell ADCC, decrease immune cell ADCP, decrease immune cell antigen presentation, reduce immune cell serotonin receptor expression (e.g., expression of one or more serotonin receptors listed in Table 1, e.g., HTR1F, HTR2B, HTR2C, HTR3A, HRT6, and/or HTR7), treat the autoimmune or inflammatory condition, reduce symptoms of an autoimmune or inflammatory condition, reduce inflammation, reduce auto-antibody levels, increase organ function, or decrease the rate or number of relapses or flare-ups.

In some embodiments of any of the foregoing aspects, the method further includes monitoring the progression of the inflammatory or autoimmune disease or condition after administration of the serotonin receptor activator or serotonin receptor-specific activator (e.g., monitoring one or more of organ function, inflammation, auto-antibody levels, the rate or number of relapses or flare-ups, development of HEVs or TLOs, immune cell migration, immune cell proliferation, immune cell recruitment, lymph node homing, lymph node egress, immune cell differentiation, immune cell activation, immune cell polarization, immune cell cytokine production, immune cell degranulation, immune cell maturation, ADCC, ADCP, and/or immune cell serotonin receptor expression (e.g., expression of one or more serotonin receptors listed in Table 1, e.g., HTR1F, HTR2B, HTR2C, HTR3A, HRT6, and/or HTR7)).

In some embodiments of any of the above aspects, the cytokine is IL-8.

In some embodiments of any of the above aspects, decreased IL-8 production reduces neutrophil migration, neutrophil activation, neutrophil recruitment, and/or neutrophil lymph node egress.

In some embodiments of any of the above aspects, the subject is a human.

In some embodiments of any of the above aspects, the subject is not diagnosed as having a neuropsychiatric disorder or migraine headaches.

In another aspect, the invention provides a therapy for treating an inflammatory or autoimmune disease or condition containing a serotonin receptor activator and a second agent selected from the group consisting of a disease-modifying anti-rheumatic drug (DMARD), a biologic response modifier (a type of DMARD), a corticosteroid, a nonsteroidal anti-inflammatory medication (NSAID), prednisone, prednisolone, methylprednisolone, methotrexate, hydroxycholorquine, sulfasalazine, leflunomide, cyclophosphamide, azathioprine, tofacitinib, adalimumab, abatacept, anakinra, kineret, certolizumab, etanercept, golimumab, infliximab, rituximab tocilizumab, an antiviral compound, a nucleoside-analog reverse transcriptase inhibitor (NRTI), a non-nucleoside reverse transcriptase inhibitor (NNRTI), an antibacterial compound, an antifungal compound, an antiparasitic compound, 6-mercaptopurine, 6-thioguanine, abatacept, adalimumab, alemtuzumab, aminosalicylates, antibiotics, anti-histamines, anti-TNFα, azathioprine, belimumab, beta interferon, calcineurin inhibitors, certolizumab, cromolyn, cyclosporin A, cyclosporine, dimethyl fumarate, fingolimod, fumaric acid esters, glatiramer acetate, hydroxyurea, IFNγ, IL-11, leflunomide, leukotriene receptor antagonist, long-acting beta2 agonist, mitoxantrone, mycophenolate mofetil, natalizumab, ocrelizumab, pimecrolimus, probiotics, retinoids, salicylic acid, short-acting beta2 agonist, sulfasalazine, tacrolimus, teriflunomide, theophylline, ustekinumab, vedolizumab, a neurotransmission modulator, or a neuronal growth factor modulator In some embodiments of any of the above aspects, the serotonin receptor activator is a serotonin receptor function activator.

In some embodiments of any of the above aspects, the serotonin receptor activator is a serotonin receptor signaling activator.

In another aspect, the invention provides a pharmaceutical composition including a serotonin receptor activator.

In some embodiments of any of the above aspects, the serotonin receptor is a serotonin receptor activating antibody or an antigen binding fragment thereof. In some embodiments of any of the above aspects, the serotonin receptor activating antibody is a serotonin receptor-specific activating antibody or an antigen binding fragment thereof (e.g., an HTR1F-specific activating antibody, an HTR2B-specific activating antibody, an HTR2C-specific activating antibody, an HRT3A-specific activating antibody, an HTR6-specific activating antibody, or an HTR7-specific activating antibody).

In some embodiments of any of the above aspects, the serotonin receptor activator is a small molecule serotonin receptor activator (e.g., agonist) listed in Table 2.

In some embodiments of any of the above aspects, the serotonin receptor activator is a neurotoxin. In some embodiments, the neurotoxin is a neurotoxin listed in Table 11. In some embodiments, the neurotoxin is cholera toxin or *Clostridium difficile* toxin A.

In some embodiments of any of the above aspects, the serotonin receptor activator is a serotonin receptor-specific activator. In some embodiments, the serotonin receptor-specific activator is a serotonin receptor-specific antibody or an antigen binding fragment thereof (e.g., an HTR1F-specific activating antibody, an HTR2B-specific activating antibody, an HTR2C-specific activating antibody, an HTR3A-specific activating antibody, an HTR6-specific activating antibody, or an HTR7-specific activating antibody). In some embodiments, the serotonin receptor-specific activator is a serotonin receptor-selective small molecule activator (e.g., agonist).

In some embodiments of any of the above aspects, the serotonin receptor activating antibody exhibits one or more of the following activities: (a) binds to an extracellular region of the serotonin receptor; or (b) agonizes the serotonin receptor. In some embodiments of any of the above aspects, the serotonin receptor activating antibody is an HTR1F-specific activating antibody and binds to an extracellular domain of HTR1F (amino acids 1-29, 84-97, 162-178, 312-329) or to amino acids 99-108 and/or 306-310 of HTR1F. In some embodiments of any of the above aspects, the serotonin receptor activating antibody is an HTR2B-specific activating antibody and binds to one or more of residues D135, V136, S139, T140, K211, F217, W337, F340, N344, or Y370 of HTR2B. In some embodiments of any of the above aspects, the serotonin receptor activating antibody is an HTR2C-specific activating antibody and binds to one or more of residues P159, S456, or V458 of HTR2C. In some embodiments of any of the above aspects, the serotonin receptor activating antibody is an HTR3A-specific activating antibody and binds to an extracellular domain of HTR3A (amino acids 24-241, 293-302, 476-478), binds to amino acids 178, 432, 436, and/or 440 of HTR3A, or binds to the expansion of amino acid 306(G) in the 5HTR3-AL isoform. In some embodiments of any of the above aspects, the serotonin receptor activating antibody is an HTR6-specific activating antibody and binds to an extracellular domain of HTR6 (amino acids 1-34, 86-100, 168-184, and/or 291-295). In some embodiments of any of the above aspects, the serotonin receptor activating antibody is an HTR7-specific activating antibody and binds to one or more of sites 5, 66, or 401 of HTR7.

In some embodiments of the above aspects, the composition further includes a second therapeutic agent.

In some embodiments of any of the above aspects, the composition further includes a pharmaceutically acceptable excipient.

In some embodiments of any of the above aspects, the second therapeutic agent is a DMARD, a biologic response modifier (a type of DMARD), a corticosteroid, an NSAID, prednisone, prednisolone, methylprednisolone, methotrexate, hydroxychloroquine, sulfasalazine, leflunomide, cyclophosphamide, azathioprine, tofacitinib, adalimumab, abatacept, anakinra, kineret, certolizumab, etanercept, golimumab, infliximab, rituximab tocilizumab, an antiviral compound, an NRTI, an NNRTI, an antibacterial compound, an antifungal compound, an antiparasitic compound, 6-mercaptopurine, 6-thioguanine, abatacept, adalimumab, alemtuzumab, aminosalicylates, antibiotics, anti-histamines, anti-TNFα, azathioprine, belimumab, beta interferon, calcineurin inhibitors, certolizumab, cromolyn, cyclosporin A, cyclosporine, dimethyl fumarate, fingolimod, fumaric acid esters, glatiramer acetate, hydroxyurea, IFNγ, IL-11, leflunomide, leukotriene receptor antagonist, long-acting beta2 agonist, mitoxantrone, mycophenolate mofetil, natalizumab, ocrelizumab, pimecrolimus, probiotics, retinoids, salicylic acid, short-acting beta2 agonist, sulfasalazine, tacrolimus, teriflunomide, theophylline, ustekinumab, vedolizumab, a serotonin receptor signaling activator, a serotonin receptor function activator, a neurotransmission modulator, or a neuronal growth factor modulator.

In some embodiments of any of the above aspects, the neurotransmission modulator is neurotoxin listed in Table 11, or a modulator (e.g., agonist or antagonist) of a neurotransmitter receptor listed in Table 7 or a neurotransmitter listed in Table 8. In some embodiments, the modulator of a neurotransmitter receptor listed in Table 7 or a neurotransmitter listed in Table 8 is an agonist or antagonist listed in Tables 9A-9J or a modulator listed in Table 10.

In some embodiments of any of the above aspects, the neuronal growth factor modulator is an agonist or antagonist of a neuronal growth factor listed in Table 12. In some embodiments, the modulator of a neuronal growth factor listed in Table 12 is an antibody listed in Table 13 or an agonist or antagonist listed in Table 14. In some embodiments, the modulator of a neuronal growth factor listed in Table 12 is selected from the group consisting of etanercept, thalidomide, lenalidomide, pomalidomide, pentoxifylline, bupropion, DOI, disitertide, and trabedersen.

In some embodiments of any of the above aspects, the serotonin receptor function activator is a serotonin receptor activating antibody or an antigen binding fragment thereof. In some embodiments of any of the above aspects, the serotonin receptor function activator is a serotonin receptor-specific activating antibody or an antigen binding fragment thereof (e.g., an HTR1F-specific activating antibody, an HTR2B-specific activating antibody, an HTR2C-specific activating antibody, an HTR3A-specific activating antibody, an HTR6-specific activating antibody, or an HTR7-specific activating antibody). In some embodiments of any of the above aspects, the serotonin receptor function activator is a small molecule serotonin activator (e.g., agonist) listed in Table 2. In some embodiments of any of the above aspects, the serotonin receptor function activator is a neurotransmission blocker. In some embodiments, the neurotransmission blocker is a neurotoxin listed in Table 11. In some embodiments, the neurotoxin is cholera toxin or *Clostridium difficile* toxin A.

In some embodiments of any of the above aspects, the serotonin receptor signaling activator is a small molecule activator. In some embodiments of any of the above aspects, the serotonin receptor signaling activator is a small molecule activator listed in Table 3.

In some embodiments of any of the above aspects, the serotonin receptor small molecule activator (e.g., agonist) is a HTR1F agonist listed in Table 2.

In some embodiments of any of the above aspects, the serotonin receptor small molecule activator (e.g., agonist) is a HTR2B agonist listed in Table 2.

In some embodiments of any of the above aspects, the serotonin receptor small molecule activator (e.g., agonist) is a HTR2C agonist listed in Table 2.

In some embodiments of any of the above aspects, the serotonin receptor small molecule activator (e.g., agonist) is a HTR3A agonist listed in Table 2.

In some embodiments of any of the above aspects, the serotonin receptor small molecule activator (e.g., agonist) is a HTR6 agonist listed in Table 2.

In some embodiments of any of the above aspects, the serotonin receptor small molecule activator (e.g., agonist) is a HTR7 agonist listed in Table 2.

In some embodiments of any of the above aspects, the serotonin receptor small molecule activator is a serotonin reuptake inhibitor, a serotonin-norepinephrine-dopamine reuptake inhibitor (SNDRI), a serotonin-norepinephrine reuptake inhibitor (SNRI), or a serotonin releasing agent listed in Table 2.

In some embodiments of any of the above aspects, the serotonin receptor activator or serotonin receptor-specific activator is selected from the group consisting of an antibody, a small molecule, and a viral vector. In some embodiments, the antibody is a serotonin receptor activating antibody or an antigen binding fragment thereof. In some embodiments, the serotonin receptor activating antibody is a serotonin receptor-specific activating antibody or an antigen binding fragment thereof (e.g., an HTR1F-specific activating antibody, an HTR2B-specific activating antibody, an HTR2C-specific activating antibody, an HTR3A-specific activating antibody, an HTR6-specific activating antibody, or an HTR7-specific activating antibody). In some embodiments, the small molecule is a small molecule listed in Table 2 or Table 3. In some embodiments, the viral vector is a viral vector expressing a neurotoxin. In some embodiments, the neurotoxin is a neurotoxin listed in Table 11. In some embodiments, the neurotoxin is cholera toxin or *Clostridium difficile* toxin A.

In some embodiments of any of the above aspects, the serotonin receptor activator or serotonin receptor-specific activator does not cross the blood brain barrier. In some embodiments, the serotonin receptor activator or the serotonin receptor-specific activator has been modified to prevent blood brain barrier crossing by conjugation to a targeting moiety, formulation in a particulate delivery system, addition of a molecular adduct, or through modulation of its size, polarity, flexibility, or lipophilicity.

In some embodiments of any of the above aspects, the serotonin receptor activator or serotonin receptor-specific activator does not have a direct effect on the central nervous system or gut.

In some embodiments of any of the above aspects, the serotonin receptor activator or serotonin receptor specific activator decreases the development of HEVs or TLOs, decreases immune cell migration, decreases immune cell proliferation, decreases immune cell recruitment, increases immune cell lymph node homing, decreases immune cell lymph node egress, decreases immune cell differentiation, decreases immune cell activation, decreases immune cell polarization, decreases immune cell cytokine production, decreases immune cell degranulation, decreases immune cell maturation, decreases immune cell ADCC, decreases immune cell ADCP, decreases immune cell antigen presentation, decreases immune cell serotonin receptor expression (e.g., expression of one or more serotonin receptors listed in Table 1, e.g., HTR1F, HTR2B, HTR2C, HTR3A, HRT6, and/or HTR7) decreases inflammation, decreases auto-antibody levels, increases organ function, or decreases the rate or number of relapses or flare-ups.

In some embodiments of any of the above aspects, the serotonin receptor is a serotonin receptor listed in Table 1. In some embodiments of any of the above aspects, the serotonin receptor is HTR1F, HTR2B, HTR2C, HTR3A, HRT6, or HTR7.

In some embodiments of any of the above aspects, the immune cell is selected from the group consisting of a T effector cell, a T helper cell (e.g., a CD4+ T cell), a cytotoxic T cell (e.g., a CD8+ T cell), a Th1 cell, a Th2 cell, a Th17 cell, a B cell, a natural killer (NK) cell, an innate lymphoid cell 1 (ILC1), an ILC2, an ILC3, a monocyte, a macrophage, a dendritic cell, a neutrophil, an M1 macrophage, an M2 macrophage, and an antigen presenting cell.

In some embodiments of any of the above aspects, the immune cell is a macrophage. In some embodiments of any of the above aspects, the method decreases macrophage migration, macrophage proliferation, macrophage recruitment, macrophage lymph node egress, macrophage differentiation, macrophage activation, macrophage polarization, macrophage cytokine production, macrophage maturation, macrophage antigen presentation, macrophage serotonin receptor expression (e.g., expression of one or more serotonin receptors listed in Table 1, e.g., HTR1F, HTR2B, HTR2C, HTR3A, HRT6, and/or HTR7), macrophage ADCC, or macrophage ADCP. In some embodiments of any of the above aspects, the method increases macrophage lymph node homing and/or improves organ function. In some embodiments of any of the above aspects, the cytokine is a pro-inflammatory cytokine. In some embodiments of any of the above aspects, the cytokine is IL-8. In some embodiments, the method decreases inflammation, auto-antibody levels, or the rate or number of relapses or flare-ups.

In some embodiments of any of the above aspects, the immune cell is a T cell (e.g., a CD8+ T cell or a CD4+ T cell). In some embodiments of any of the above aspects, the method decreases T cell migration, T cell proliferation, T cell recruitment, T cell lymph node egress, T cell differentiation, T cell activation, T cell polarization, T cell cytokine production, T cell maturation, T cell antigen presentation, T cell serotonin receptor expression (e.g., expression of one or more serotonin receptors listed in Table 1, e.g., HTR1F, HTR2B, HTR2C, HTR3A, HRT6, and/or HTR7), T cell ADCC, or T cell ADCP. In some embodiments of any of the above aspects, the method increases T cell lymph node homing and/or improves organ function. In some embodiments of any of the above aspects, the cytokine is a pro-inflammatory cytokine. In some embodiments of any of the above aspects, the cytokine is IL-8. In some embodiments, the method decreases inflammation, auto-antibody levels, or the rate or number of relapses or flare-ups.

In some embodiments of any of the above aspects, the immune cell is a dendritic cell. In some embodiments of any of the above aspects, the method decreases dendritic cell migration, dendritic cell proliferation, dendritic cell recruitment, dendritic cell lymph node egress, dendritic cell differentiation, dendritic cell activation, dendritic cell polarization, dendritic cell cytokine production, dendritic cell maturation, dendritic cell antigen presentation, dendritic cell serotonin receptor expression (e.g., expression of one or more serotonin receptors listed in Table 1, e.g., HTR1F, HTR2B, HTR2C, HTR3A, HRT6, and/or HTR7), dendritic cell ADCC, or dendritic cell ADCP. In some embodiments of any of the above aspects, the method increases dendritic cell lymph node homing and/or improves organ function. In some embodiments of any of the above aspects, the cytokine is a pro-inflammatory cytokine. In some embodiments of any of the above aspects, the cytokine is IL-8. In some embodiments, the method decreases inflammation, auto-antibody levels, or the rate or number of relapses or flare-ups.

In some embodiments of any of the above aspects, the immune cell is a neutrophil. In some embodiments of any of the above aspects, the method decreases neutrophil migration, neutrophil proliferation, neutrophil differentiation, neutrophil maturation, neutrophil recruitment, neutrophil activation, neutrophil antigen presentation, neutrophil serotonin receptor expression (e.g., expression of one or more serotonin receptors listed in Table 1, e.g., HTR1F, HTR2B, HTR2C, HTR3A, HRT6, and/or HTR7), neutrophil ADCC, or neutrophil ADCP. In some embodiments of any of the above aspects, the method increases neutrophil lymph node homing and/or improves organ function. In some embodiments, the cytokine is a pro-inflammatory cytokine. In some embodiments of any of the above aspects, the cytokine is IL-8. In some embodiments, the method decreases inflammation, auto-antibody levels, or the rate or number of relapses or flare-ups. In some embodiments of any of the above aspects, the method reduces neutrophil migration, neutrophil activation, neutrophil recruitment, or neutrophil lymph node egress by decreasing IL-8 cytokine production by macrophages, T cells, or dendritic cells.

Definitions

As used herein, "administration" refers to providing or giving a subject a therapeutic agent (e.g., a serotonin receptor activator), by any effective route. Exemplary routes of administration are described herein below.

As used herein, the term "agonist" refers to an agent (e.g., a small molecule or antibody) that increases receptor activity. An agonist may activate a receptor by directly binding to the receptor, by acting as a cofactor, by modulating receptor conformation (e.g., maintaining a receptor in an open or active state). An agonist may increase receptor activity by 10%, 20%, 30%, 40%, 50%, 60%, 70%, 80%, 90%, 95%, 98% or more. An agonist may induce maximal receptor activation or partial activation depending on the concentration of the agonist and its mechanism of action.

As used herein, the term "analog" refers to a protein of similar nucleotide or amino acid composition or sequence to any of the proteins or peptides of the invention, allowing for variations that do not have an adverse effect on the ability of the protein or peptide to carry out its normal function (e.g., bind to a receptor or promote synapse formation). Analogs may be the same length, shorter, or longer than their corresponding protein or polypeptide. Analogs may have about 60% (e.g., about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, or about 99%) identity to the amino acid sequence of the naturally occurring protein or peptide. An analog can be a naturally occurring protein or polypeptide sequence that is modified by deletion, addition, mutation, or substitution of one or more amino acid residues.

As used herein, the term "antagonist" refers to an agent (e.g., a small molecule or antibody) that reduces or inhibits receptor activity. An antagonist may reduce receptor activity by directly binding to the receptor, by blocking the receptor binding site, by modulating receptor conformation (e.g., maintaining a receptor in a closed or inactive state). An antagonist may reduce receptor activity by 10%, 20%, 30%, 40%, 50%, 60%, 70%, 80%, 90%, 95%, 98% or more. An antagonist may also completely block or inhibit receptor activity. Antagonist activity may be concentration-dependent or -independent.

As used herein, the term "antibody" refers to a molecule that specifically binds to, or is immunologically reactive with, a particular antigen and includes at least the variable domain of a heavy chain, and normally includes at least the variable domains of a heavy chain and of a light chain of an immunoglobulin. Antibodies and antigen-binding fragments, variants, or derivatives thereof include, but are not limited to, polyclonal, monoclonal, multispecific, human, humanized, primatized, or chimeric antibodies, heteroconjugate antibodies (e.g., bi- tri- and quad-specific antibodies, diabodies, triabodies, and tetrabodies), single-domain antibodies (sdAb), epitope-binding fragments, e.g., Fab, Fab' and F(ab')$_2$, Fd, Fvs, single-chain Fvs (scFv), rIgG, single-chain antibodies, disulfide-linked Fvs (sdFv), fragments containing either a $V_L$ or $V_H$ domain, fragments produced by an Fab expression library, and anti-idiotypic (anti-Id) antibodies. Antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Moreover, unless otherwise indicated, the term "monoclonal antibody" (mAb) is meant to include both intact molecules as well as antibody fragments (such as, for example, Fab and F(ab')$_2$ fragments) that are capable of specifically binding to a target protein. Fab and F(ab')$_2$ fragments lack the Fc fragment of an intact antibody.

The term "antigen-binding fragment," as used herein, refers to one or more fragments of an immunoglobulin that retain the ability to specifically bind to a target antigen. The antigen-binding function of an immunoglobulin can be performed by fragments of a full-length antibody. The antibody fragments can be a Fab, F(ab')$_2$, scFv, SMIP, diabody, a triabody, an affibody, a nanobody, an aptamer, or a domain antibody. Examples of binding fragments encompassed by the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment containing two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb (Ward et al., Nature 341:544-546, 1989) including $V_H$ and $V_L$ domains; (vi) a dAb fragment that consists of a $V_H$ domain; (vii) a dAb that consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv)). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In other embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, the terms "effective amount," "therapeutically effective amount," and a "sufficient amount" of a composition, antibody, vector construct, viral vector or cell described herein refer to a quantity sufficient to, when administered to a subject, including a mammal (e.g., a human), effect beneficial or desired results, including effects at the cellular level, tissue level, or clinical results, and, as such, an "effective amount" or synonym thereto depends upon the context in which it is being applied. For example, in the context of treating inflammatory or autoimmune disease or condition it is an amount of the composition, antibody, vector construct, viral vector or cell sufficient to achieve a treatment response as compared to the response obtained without administration of the composition, antibody, vector construct, viral vector or cell. The amount of a given composition described herein that will correspond to such an amount will vary depending upon various factors, such as the given agent, the pharmaceutical formulation, the route of administration, the type of disease or disorder, the identity of the subject (e.g., age, sex, weight) or host being treated, and the like, but can nevertheless be routinely determined by one skilled in the art. Also, as used herein, a "therapeutically effective amount" of a composition, antibody, vector construct, viral vector or cell of the present disclosure is an amount that results in a beneficial or desired result in a subject as compared to a control. As defined herein, a therapeutically effective amount of a composition, antibody, vector construct, viral vector or cell of the present disclosure may be readily determined by one of ordinary skill by routine methods known in the art. Dosage regimen may be adjusted to provide the optimum therapeutic response.

As used herein, the terms "increasing" and "decreasing" refer to modulating resulting in, respectively, greater or lesser amounts, of function, expression, or activity of a metric relative to a reference. For example, subsequent to administration of a serotonin receptor activator in a method described herein, the amount of a marker of a metric (e.g., immune cell suppression or inactivation) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "innervated" refers to a tissue (e.g., a lymph node, spleen, primary, secondary and tertiary lymphoid organ, barrier tissue such as skin, gut, and airway, wounds) that contains nerves. "Innervation" refers to the process of nerves entering a tissue.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect.

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, a "pharmaceutical composition" or "pharmaceutical preparation" is a composition or preparation having pharmacological activity or other direct effect in the mitigation, treatment, or prevention of disease, and/or a finished dosage form or formulation thereof and which is indicated for human use.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "proliferation" refers to an increase in cell numbers through growth and division of cells.

As used herein, the term "reference" refers to a level, expression level, copy number, sample or standard that is used for comparison purposes. For example, a reference sample can be obtained from a healthy individual (e.g., an individual who does not have an inflammatory or autoimmune disease). A reference level can be the level of expression of one or more reference samples. For example, an average expression (e.g., a mean expression or median expression) among a plurality of individuals (e.g., healthy individuals, or individuals who do not have an inflammatory or autoimmune disease). In other instances, a reference level can be a predetermined threshold level, e.g., based on functional expression as otherwise determined, e.g., by empirical assays.

As used herein, the term "sample" refers to a specimen (e.g., blood, blood component (e.g., serum or plasma), urine, saliva, amniotic fluid, cerebrospinal fluid, tissue (e.g., lymph node, gut, skin, barrier tissue, airway tissue, or wound tissue), pancreatic fluid, chorionic villus sample, and cells, e.g., immune cells) isolated from a subject.

As used herein, the terms "subject" and "patient" refer to an animal (e.g., a mammal, such as a human). A subject to be treated according to the methods described herein may be one who has been diagnosed with a particular condition, or one at risk of developing such conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

"Treatment" and "treating," as used herein, refer to the medical management of a subject with the intent to improve, ameliorate, stabilize (i.e., not worsen), prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

As used herein, the term "under-expressed" refers to a nucleic acid or polypeptide that is expressed or caused to be expressed or produced in a cell at a lower level than is normally expressed in the corresponding wild-type cell. For example, a serotonin receptor is "under-expressed" in an immune cell when the serotonin receptor is present at a lower level in the immune cell compared to the level in a healthy cell of the same tissue or cell type from the same species or individual. A serotonin receptor is under-expressed when serotonin receptor expression is decreased by 1.1-fold or more (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) compared to a reference (e.g., a healthy cell of the same type).

As used herein, the term "activation" refers to the response of an immune cell to a perceived insult. When immune cells become activated, they proliferate, secrete pro-inflammatory cytokines, differentiate, present antigens, become more polarized, and become more phagocytic and cytotoxic. Factors that stimulate immune cell activation include pro-inflammatory cytokines, pathogens, and non-self antigen presentation (e.g., antigens from pathogens presented by dendritic cells, macrophages, or B cells).

As used herein, the terms "antibody-dependent cell mediated cytotoxicity" and "antibody-dependent cellular toxicity" (ADCC) refer to the killing of an antibody-coated target cell by a cytotoxic effector cell through a non-phagocytic process, characterized by the release of the content of cytotoxic granules or by the expression of cell death-inducing molecules. ADCC is triggered through interaction of target-bound antibodies (belonging to IgG or IgA or IgE classes) with certain Fc receptors (FcRs), glycoproteins present on the effector cell surface that bind the Fc region of immunoglobulins (Ig). Effector cells that mediate ADCC include natural killer (NK) cells, monocytes, macrophages, neutrophils, eosinophils and dendritic cells.

As used herein, the terms "antibody-dependent cell mediated phagocytosis" and "antibody-dependent cellular phagocytosis" (ADCP) refer to the phagocytosis (e.g., engulfment) of an antibody-coated target cell by immune cells (e.g., phagocytes). ADCP is triggered through interaction of target-bound antibodies (belonging to IgG or IgA or IgE classes) with certain Fc receptors (FcRs, e.g., FcγRIIa, FcγRIIIa, and FcγRI), glycoproteins present on the effector cell surface that bind the Fc region of immunoglobulins (Ig).

Effector cells that mediate ADCP include monocytes, macrophages, neutrophils, and dendritic cells.

As used herein, the term "antigen presentation" refers to a process in which fragments of antigens are displayed on the cell surface of immune cells. Antigens are presented to T cells and B cells to stimulate an immune response. Antigen presenting cells include dendritic cells, B cells, and macrophages. Mast cells and neutrophils can also be induced to present antigens.

As used herein, the term "anti-inflammatory cytokine" refers to a cytokine produced or secreted by an immune cell that reduces inflammation. Immune cells that produce and secrete anti-inflammatory cytokines include T cells (e.g., Th cells) macrophages, B cells, and mast cells. Anti-inflammatory cytokines include IL4, IL-11, IL-13, interferon alpha (IFNα) and transforming growth factor-beta (TGFβ). As used herein, the term "chemokine" refers to a type of small cytokine that can induce directed chemotaxis in nearby cells. Classes of chemokines include CC chemokines, CXC chemokines, C chemokines, and CX3C chemokines. Chemokines can regulate immune cell migration and homing, including the migration and homing of monocytes, macrophages, T cells, mast cells, eosinophils, and neutrophils. Chemokines responsible for immune cell migration include CCL19, CCL21, CCL14, CCL20, CCL25, CCL27, CXCL12, CXCL13, CCR9, CCR10, and CXCR5. Chemokines that can direct the migration of inflammatory leukocytes to sites of inflammation or injury include CCL2, CCL3, CCL5, CXCL1, CXCL2, and CXCL8.

As used herein, the term "cytokine" refers to a small protein involved in cell signaling. Cytokines can be produced and secreted by immune cells, such as T cells, B cells, macrophages, and mast cells, and include chemokines, interferons, interleukins, lymphokines, and tumor necrosis factors.

As used herein, the term "cytokine production" refers to the expression, synthesis, and secretion (e.g., release) of cytokines by an immune cell.

As used herein, the term "cytotoxicity" refers to the ability of immune cells to kill other cells. Immune cells with cytotoxic functions release toxic proteins (e.g., perforin and granzymes) capable of killing nearby cells. Natural killer cells, ILCs, and cytotoxic T cells (e.g., CD8+ T cells) are the primary cytotoxic effector cells of the immune system, although dendritic cells, neutrophils, eosinophils, mast cells, basophils, macrophages, and monocytes have been shown to have cytotoxic activity.

As used herein, the term "differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, immune cell, or endothelial cell). Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). By "committed" or "differentiated" is meant a cell that expresses one or more markers or other characteristic of a cell of a particular lineage.

As used herein, the term "degranulation" refers to a cellular process in which molecules, including antimicrobial and cytotoxic molecules, are released from intracellular secretory vesicles called granules. Degranulation is part of the immune response to pathogens and invading microorganisms by immune cells such as granulocytes (e.g., neutrophils, basophils, and eosinophils), mast cells, and lymphocytes (e.g., natural killer cells, ILCs, and cytotoxic T cells). The molecules released during degranulation vary by cell type and can include molecules designed to kill the invading pathogens and microorganisms or to promote an immune response, such as inflammation.

As used herein, the term "immune dysregulation" refers to a condition in which the immune system is disrupted or responding to an insult. Immune dysregulation includes aberrant activation (e.g., autoimmune disease), activation in response to an injury or disease (e.g., disease-associated inflammation), and activation in response to a pathogen or infection (e.g., parasitic infection). Immune dysregulation can be treated using the methods and compositions described herein to direct immune cells to carry out beneficial functions and reduce harmful activities (e.g., reducing activation and pro-inflammatory cytokine secretion in subjects with autoimmune disease).

As used herein, the term "modulating an immune response" refers to any alteration in a cell of the immune system or any alteration in the activity of a cell involved in the immune response. Such regulation or modulation includes an increase or decrease in the number of various cell types, an increase or decrease in the activity of these cells, or any other changes that can occur within the immune system. Cells involved in the immune response include, but are not limited to, T lymphocytes (T cells), B lymphocytes (B cells), natural killer (NK) cells, innate lymphoid cells (ILCs), macrophages, eosinophils, mast cells, dendritic cells and neutrophils. In some cases, "modulating" the immune response means the immune response is stimulated or enhanced, and in other cases "modulating" the immune response means suppression of the immune system.

As used herein, the term "lymph node egress" refers to immune cell exit from the lymph nodes, which occurs during immune cell recirculation. Immune cells that undergo recirculation include lymphocytes (e.g., T cells, B cells, and natural killer cells), which enter the lymph node from blood to survey for antigen and then exit into lymph and return to the blood stream to perform antigen surveillance.

As used herein, the term "lymph node homing" refers to directed migration of immune cells to a lymph node. Immune cells that return to lymph nodes include T cells, B cells, macrophages, and dendritic cells.

As used herein, the term "migration" refers to the movement of immune cells throughout the body. Immune cells can migrate in response to external chemical and mechanical signals. Many immune cells circulate in blood including peripheral blood mononuclear cells (e.g., lymphocytes such as T cells, B cells, and natural killer cells), monocytes, macrophages, dendritic cells, and polymorphonuclear cells (e.g., neutrophils and eosinophils). Immune cells can migrate to sites of infection, injury, or inflammation, back to the lymph nodes, or to tumors or cancer cells.

As used herein, the term "phagocytosis" refers to the process in which a cell engulfs or ingests material, such as other cells or parts of cells (e.g., bacteria), particles, or dead or dying cells. A cell that capable of performing this function is called a phagocyte. Immune phagocytes include neutrophils, monocytes, macrophages, mast cells, B cells, eosinophils, and dendritic cells.

As used herein, the term "polarization" refers to the ability of an immune cell to shift between different functional states. A cell that is moving toward one of two functional extremes is said to be in the process of becoming more polarized. The term polarization is often used to refer to macrophages, which can shift between states known as M1 and M2. M1, or classically activated, macrophages secrete pro-inflammatory cytokines (e.g., IL-12, TNF, IL-6, IL-8, IL-1B, MCP-1, and CCL2), are highly phagocytic, and respond to pathogens and other environmental insults. M1 macrophages can also be detected by expression of Nos2. M2, or alternatively activated, macrophages secrete a different set of cytokines (e.g., IL-10) and are less phagocytic. M2 macrophages can detected by expression of Arg1, IDO, PF4, CCL24, IL10, and IL4Rα. Cells become polarized in response to external cues such as cytokines, pathogens, injury, and other signals in the tissue microenvironment.

As used herein, the term "pro-inflammatory cytokine" refers to a cytokine secreted from immune cells that promotes inflammation. Immune cells that produce and secrete pro-inflammatory cytokines include T cells (e.g., Th cells) macrophages, B cells, and mast cells. Pro-inflammatory cytokines include interleukin-1 (IL-1, e.g., IL-1β), IL-5, IL-6, IL-8, IL-10, IL-12, IL-13, IL-18, tumor necrosis factor (TNF, e.g., TNFα), interferon gamma (IFNγ), and granulocyte macrophage colony stimulating factor (GMCSF).

As used herein, the term "pro-survival cytokine" refers to a cytokine that promotes the survival of immune cells (e.g., T cells). Pro-survival cytokines include IL-2, IL-4, IL-6, IL-7, and IL-15.

As used herein, the term "recruitment" refers to the re-distribution of immune cells to a particular location (e.g., the site of infection, injury, or inflammation). Immune cells that can undergo this re-distributed and be recruited to sites of injury or disease include monocytes, macrophages, T cells, B cells, dendritic cells, and natural killer cells.

As used herein, the term "serotonin receptor-associated inflammatory or autoimmune disease or condition" refers to an inflammatory or autoimmune disease or condition that is associated with immune cells in which a serotonin receptor is expressed (e.g., immune cells that express one or more serotonin receptors (e.g., one or more serotonin receptors listed in Table 1, e.g., HTR1F, HTR2B, HTR2C, HTR3A, HRT6, and/or HTR7) or immune cells having decreased expression of one or more serotonin receptors (e.g., one or more serotonin receptors listed in Table 1, e.g., HTR1F, HTR2B, HTR2C, HTR3A, HRT6, and/or HTR7) compared to a reference (e.g., an immune cell from a subject that does not have an inflammatory or autoimmune disease or condition)). The immune cells can be systemic immune cells or immune cells that have infiltrated the affected tissue or tissues (e.g., infiltrating immune cells or tissue resident immune cells). Serotonin receptor-associated inflammatory or autoimmune diseases or conditions can be identified by assessing an immune cell or a biopsy of an immune-cell infiltrated tissue sample for immune cell serotonin receptor expression (e.g., gene or protein expression) and comparing it to serotonin receptor expression in a reference cell.

The term "serotonin receptor activating antibody" refers to antibodies that are capable of binding to serotonin receptors (e.g., a serotonin receptor listed in Table 1) and activating or increasing serotonin receptor function and/or inducing one or more signal transduction pathways mediated by serotonin receptors. The term "serotonin receptor-specific activating antibody" refers to antibodies that bind specifically to one type of serotonin receptor (e.g., HTR1F, HTR2B, HTR2C, HTR3A, HRT6, or HTR7) and activate or increase serotonin receptor function and/or induce one or more signal transduction pathways mediated by the serotonin receptor. Serotonin receptor activating antibodies and serotonin receptor-specific activating antibodies activate or increase serotonin receptor function and/or induce one or more serotonin receptor-mediated signal transduction pathways by at least 10% (e.g., 10%, 20%, 30%, 40%, 50%, 60%, 70%, 80%, 90%, 95%, 98% or more).

As used herein, the term "serotonin receptor activator" refers to an agent that activates or increases serotonin receptor function, activation, or signaling. Serotonin receptor activators include serotonin receptor activating antibodies and antigen binding fragments thereof, small molecules that activate (e.g., agonize) serotonin receptors, and other agents that activate a serotonin receptor to induce or increase serotonin receptor expression, serotonin receptor binding, serotonin receptor function, or signal transduction downstream of serotonin receptors Serotonin receptor activators increase serotonin receptor function or signaling by 10% or more (e.g., 10%, 20%, 30%, 40%, 50%, 60%, 70%, 80%, 90%, 95%, 98% or more).

As used herein, the term "serotonin receptor-specific activator" refers to a serotonin receptor activator that selectively induces or increases the function or signaling of a single serotonin receptor (e.g., HTR1F, HTR2B, HTR2C, HTR3A, HRT6, or HTR7) without substantially affecting the function or signaling of other serotonin receptors. Serotonin receptor-specific activators include serotonin receptor-specific activating antibodies and small molecule serotonin receptor-selective activators (e.g., agonists). Serotonin receptor-specific activators increase serotonin receptor function or signaling by 10% or more (e.g., 10%, 20%, 30%, 40%, 50%, 60%, 70%, 80%, 90%, 95%, 98% or more).

As used herein, the term "serotonin receptor function activator" refers to a type of serotonin receptor activator that induces or increases serotonin receptor function, such as by increasing the expression or activity of a serotonin receptor. Exemplary serotonin receptor function activators include serotonin receptor activating antibodies and small molecule serotonin receptor agonists. Serotonin receptor function activators increase serotonin receptor function by 10% or more (e.g., 10%, 20%, 30%, 40%, 50%, 60%, 70%, 80%, 90%, 95%, 98% or more).

As used herein, the term "serotonin receptor signaling activator" refers to a type of serotonin receptor activator that activates or increases the intracellular signaling that is downstream of serotonin receptor activation or interaction with a binding partner. Exemplary serotonin receptor signaling activators include small molecule agonists directed to molecules in downstream signaling cascades. Serotonin receptor signaling activators increase downstream signaling by 10% or more (e.g., 10%, 20%, 30%, 40%, 50%, 60%, 70%, 80%, 90%, 95%, 98% or more).

As used herein, the terms "serotonin receptor small molecule activator," "small molecule serotonin receptor activator," "serotonin receptor small molecule agonist," and "small molecule serotonin receptor agonist" refer to a small molecule that activates function or signaling of a serotonin receptor (e.g., one or more serotonin receptors listed in Table 1, e.g., HTR1F, HTR2B, HTR2C, HTR3A, HRT6, and/or HTR7) and has an EC50 of 10 µM or lower. A "serotonin receptor small molecule agonist" acts by binding directly to a serotonin receptor, while a "serotonin receptor small molecule activator" includes both agonists that bind directly to a serotonin receptor and small molecule activators that have an indirect effect on serotonin receptors (e.g., a serotonin reuptake inhibitor). The serotonin receptor agonist may be selective for a single serotonin receptor (e.g., primarily induces or increases the function or activation of a single serotonin receptor compared to other serotonin receptors), or the serotonin receptor agonist may exhibit similar activation of multiple serotonin receptors (e.g., more than one serotonin receptor listed in Table 1). Serotonin receptor agonists for use in the methods and compositions described herein are provided in Table 2.

As used herein, the term "IL-8-associated inflammatory or autoimmune disease or condition" refers to an inflammatory or autoimmune disease or condition in which IL-8 is elevated. Exemplary IL-8-associated inflammatory or autoimmune diseases or conditions include collagen-induced arthritis, coxsackie myocarditis, glomerulonephritis, pemphigus vulgaris, psoriasis, rheumatoid arthritis, uveitis, scleroderma, dermatitis, Crohn's disease, inclusion body myositis, juvenile myositis, and idiopathic pulmonary fibrosis.

As used herein, an agent that "does not cross the blood brain barrier" is an agent that does not significantly cross the barrier between the peripheral circulation and the brain and spinal cord. This can also be referred to as a "blood brain barrier impermeable" agent. Agents will have a limited ability to cross the blood brain barrier if they are not lipid soluble or have a molecular weight of over 600 Daltons. Agents that typically cross the blood brain barrier can be modified to become blood brain barrier impermeable based on chemical modifications that increase the size or alter the hydrophobicity of the agent, packaging modifications that reduce diffusion (e.g., packaging an agent within a microparticle or nanoparticle), and conjugation to biologics that direct the agent away from the blood brain barrier (e.g., conjugation to a pancreas-specific antibody). An agent that does not cross the blood brain barrier is an agent for which 30% or less (e.g., 30%, 25%, 20%, 15%, 10%, 5%, 2% or less) of the administered agent crosses the blood brain barrier.

As used herein, an agent that "does not have a direct effect on the central nervous system (CNS) or gut" is an agent that does not directly alter neurotransmission, neuronal numbers, or neuronal morphology in the CNS or gut when administered according to the methods described herein. This may be assessed by administering the agents to animal models and performing electrophysiological recordings or immunohistochemical analysis. An agent will be considered not to have a direct effect on the CNS or gut if administration according to the methods described herein has an effect on neurotransmission, neuronal numbers, or neuronal morphology in the CNS or gut that is 50% or less (e.g., 50%, 45%, 40%, 35%, 30%, 25%, 20%, 15%, 10%, 5%, or less) of the effect observed if the same agent is administered directly to the CNS or gut.

As used herein, the term "migraine" refers to a neurological disorder characterized by moderate to severe headaches often accompanied by nausea, vomiting, or sensitivity to light.

As used herein, the term "neuropsychiatric disorder" refers to a psychiatric or mental disorder that may cause suffering or an impaired ability to function. A neuropsychiatric disorder is a syndrome characterized by clinically significant disturbance in an individual's cognition, emotion regulation, or behavior that reflects a dysfunction in the psychological, biological, or developmental processes underlying mental functioning. Neuropsychiatric disorders may be diagnosed by psychiatrists, psychologists, neurologists, or physicians. Neuropsychiatric disorders include mood disorders (e.g., depression, bipolar depression, major depressive disorder), psychotic disorders (e.g., schizophrenia, schizoaffective disorder), personality disorders (e.g., borderline personality disorder, obsessive compulsive personality disorder, narcissistic personality disorder), eating disorders, sleep disorders, sexual disorders, anxiety disorders (e.g., generalized anxiety disorder, social anxiety disorder, post-traumatic stress disorder), developmental disorders (e.g., autism, attention deficit disorder, attention deficit hyperactivity disorder), benign forgetfulness, childhood learning disorders, Alzheimer's disease, addiction, and others listed in the *Diagnostic and Statistical Manual of Mental Disorders* (DSM).

As used herein, the term "neuronal growth factor modulator" refers to an agent that regulates neuronal growth, development, or survival. Neuronal growth factors include proteins that promote neurogenesis, neuronal growth, and neuronal differentiation (e.g., neurotrophic factors NGF, NT3, BDNF, CNTF, and GDNF), proteins that promote neurite outgrowth (e.g., axon or dendrite outgrowth or stabilization), or proteins that promote synapse formation (e.g., synaptogenesis, synapse assembly, synaptic adhesion, synaptic maturation, synaptic refinement, or synaptic stabilization). These processes lead to innervation of tissue, including neural tissue, muscle, lymph nodes and tumors, and the formation of synaptic connections between two or more neurons and between neurons and non-neural cells (e.g., immune cells). A neuronal growth factor modulator may block one or more of these processes (e.g., through the use of antibodies that block neuronal growth factors or their receptors) or promote one or more of these processes (e.g., through the use of these proteins or analogs or peptide fragments thereof). Exemplary neuronal growth factors are listed in Table 12. Neuronal growth factor modulators decrease or increase neurite outgrowth, innervation, synapse formation, or any of the aforementioned processes by 10% or more (e.g., 10%, 20%, 30%, 40%, 50%, 60%, 70%, 80%, 90%, 95%, 98% or more).

As used herein, the term "neurotransmission modulator" refers to an agent that either induces or increases neurotransmission or decreases or blocks neurotransmission. Neurotransmission modulators can increase or decrease neurotransmission by 10%, 20%, 30%, 40%, 50%, 60%, 70%, 80%, 90%, 95%, 98% or more. Exemplary neurotransmitters and neurotransmitter receptors are listed in Tables 7 and 8. Neurotransmission modulators may increase neurotransmission by increasing neurotransmitter synthesis or release, preventing neurotransmitter reuptake or degradation, increasing neurotransmitter receptor activity, increasing neurotransmitter receptor synthesis or membrane insertion, decreasing neurotransmitter degradation, and regulating neurotransmitter receptor conformation. Neurotransmission modulators that increase neurotransmission include neurotransmitters and analogs thereof and neurotransmitter receptor agonists. Neurotransmission modulators may decrease neurotransmission by decreasing neurotransmitter synthesis or release, increasing neurotransmitter reuptake or degradation, decreasing neurotransmitter receptor activity, decreasing neurotransmitter receptor synthesis or membrane insertion, increasing neurotransmitter degradation, regulating neurotransmitter receptor conformation, and disrupting the pre- or postsynaptic machinery. Neurotransmission modulators that decrease or block neurotransmission include antibodies that bind to or block the function of neurotransmitters, neurotransmitter receptor antagonists, and toxins that disrupt synaptic release.

DETAILED DESCRIPTION

Described herein are compositions and methods for the treatment of an inflammatory or autoimmune disease or condition in a subject (e.g., a mammalian subject, such as a human) by administering serotonin receptor activators.

Serotonin receptor activators include activators specific to a serotonin receptor (e.g., serotonin receptor-specific activating antibodies) and non-specific activators that could potentially affect other proteins due to their having shared binding partners or signaling pathways with serotonin receptors. These methods and compositions provide new mechanistic approaches for treating inflammatory or autoimmune diseases or conditions.

Serotonin Receptors

Serotonin receptors are a family of G protein-coupled receptor and ligand-gated ion channels found in the central and peripheral nervous systems. The serotonin receptors may be activated by the neurotransmitter serotonin, which acts as their natural ligand. Serotonin receptors modulate the release of many neurotransmitters, including glutamate, GABA, dopamine, epinephrine/norepinephrine, and acetylcholine, as well as many hormones, including oxytocin, prolactin, vasopressin, cortisol, corticotropin, and substance P, among others. They also influence various biological and neurological processes such as aggression, anxiety, appetite, cognition, learning, memory, mood, nausea, sleep, and thermoregulation The present invention relates to the surprising discovery that serotonin receptors (especially HTR1F, HTR2B, HTR2C, HRT3A, HTR6, and HTR7) are highly expressed on macrophages, dendritic cells, and T cells. The addition of serotonin receptor agonists to cultured M2 macrophages reduced macrophage production of the pro-inflammatory cytokine IL-8. IL8 is the primary cytokine for driving the recruitment and activation of neutrophils. These findings indicate that activation of serotonin receptors reduces the production of pro-inflammatory cytokines and may protect the host from excessive, aberrant immune responses. Through this mechanism, activation of serotonin receptors can reduce inflammation, induce tolerance, and be used as a therapeutic strategy for treating inflammatory and autoimmune diseases or conditions, particularly diseases or conditions driven by macrophages in barrier tissue (e.g., allergy, asthma, inflammatory bowel disease (IBD), Crohn's, Ulcerative Colitis, dermatitis, fibrosis, and wound-healing) and diseases driven by neutrophils (e.g. systemic lupus erythematosus, small vessel vasculitis and rheumatoid arthritis).

Serotonin Receptor Activators

Serotonin receptor activators described herein can activate or increase serotonin receptor function or signaling in order to treat inflammatory or autoimmune diseases or conditions. Serotonin receptor activators can be grouped into categories based on their mechanism of action and their effect on serotonin receptors: 1) serotonin receptor-specific activators (e.g., activators that only activate the function or signaling of a single serotonin receptor, such as serotonin receptor-specific activating antibodies or serotonin receptor-selective small molecule agonists), 2) serotonin receptor function activators (e.g., activators that increase the activity or more than one serotonin receptor, such as non-selective serotonin receptor small molecule activators), and 3) serotonin receptor signaling activators (e.g., activators that activate downstream signaling pathways or intracellular events that occur after activation of serotonin receptors).

Serotonin Receptor-Specific Activators

In some embodiments, the serotonin receptor activator is a serotonin receptor-specific activator. Serotonin receptor-specific activators selectively increase or activate the function, expression, activation, or signaling of a single serotonin receptor (e.g., a serotonin receptor in Table 1, e.g., HTR1F, HTR2B, HTR2C, HTR3A, HTR6, or HTR7) without directly affecting other serotonin receptors. Serotonin receptor-specific activators include serotonin receptor-specific activating antibodies or antigen binding fragments thereof and serotonin receptor-selective small molecule activators. Serotonin receptor-specific activators can increase serotonin receptor function, expression, or signaling by 5% or more (e.g., 5%, 10%, 15%, 20%, 25%, 30%, 40%, 50%, 60%, 70%, 80%, 90%, 95%, 99%, or more).

In some embodiments, the serotonin receptor activating antibody is a serotonin receptor-specific activating antibody or an antigen binding fragment thereof that binds to a serotonin receptor and activates or increases serotonin receptor function. Serotonin receptor-specific activating antibodies include antibodies having one or more of the following functional properties: has agonistic activity (e.g., activates a serotonin receptor); or binds to one or more extracellular regions of a serotonin receptor. In some embodiments, the serotonin receptor-specific activating antibody is a HTR1F-specific activating antibody and binds to an extracellular domain of HTR1F (amino acids 1-29, 84-97, 162-178, and/or 312-329) or to amino acids 99-108 and/or 306-310 of HTR1F. In some embodiments, the serotonin receptor-specific activating antibody is a HTR2B-specific activating antibody and binds to one or more of residues D135, V136, S139, T140, K211, F217, W337, F340, N344, or Y370 of HTR2B. In some embodiments, the serotonin receptor-specific activating antibody is a HTR2C-specific activating antibody and binds to one or more of residues P159, S456, or V458 of HTR2C. In some embodiments, the serotonin receptor-specific activating antibody is a HTR3A-specific activating antibody and binds to an extracellular domain of HTR3A (amino acids 24-241, 293-302, and/or 476-478) or to amino acids 178, 432, 436, and/or 440 of HTR3A, or to the expansion of amino acid 306(G) in the 5HTR3A-AL isoform. In some embodiments, the serotonin receptor-specific activating antibody is a HTR6-specific activating antibody and binds to an extracellular domain of HTR6 (amino acids 1-34, 86-100, 168-184, and/or 291-295). In some embodiments, the serotonin receptor-specific activating antibody is a HTR7-specific activating antibody and binds to one or more glycosylation sites (e.g., glycosylation sites 5 or 66) or a lipidation site (e.g., lipidation site 401) of HTR7. Antibodies having one or more of these functional properties are routinely screened and selected once the desired functional property is identified herein (e.g., by screening of phage display or other antibody libraries).

In some embodiments, the serotonin receptor-specific activator is a small molecule activator (e.g., agonist) that is selective for a specific serotonin receptor (e.g., a serotonin receptor listed in Table 1, e.g., an HTR1F-selective activator, an HTR2B-selective activator, an HTR2C-selective activator, an HTR3A-selective activator, an HTR6-selective activator, or an HTR7-selective activator). Serotonin receptor-specific small molecule activators for use in the methods and compositions described herein are included in Table 2.

Serotonin Receptor Function Activators

In some embodiments, the serotonin receptor activator is a serotonin receptor function activator. Serotonin receptor function activators activate or increase serotonin receptor function by increasing serotonin receptor expression or activation. Serotonin receptor function activators include serotonin receptor-specific activators that activate or increase serotonin receptor function or expression (e.g., serotonin receptor-specific activating antibodies or antigen binding fragments thereof or small molecule serotonin receptor-selective activators), or serotonin receptor activating antibodies or antigen binding fragments thereof or small molecule serotonin receptor activators that bind to or activate more than one serotonin receptor In some embodiments, the serotonin receptor activating antibodies bind to or increase the activity of more than one serotonin receptor (e.g., at least two or more serotonin receptors listed in Table 1) and have one or more of the following functional properties: agonizes the serotonin receptors; or binds to one or more extracellular regions of the serotonin receptors. Antibodies or antibody-like molecules having one or more of these functional properties are routinely screened and selected once the desired functional property is identified herein (e.g., by screening of phage display or other antibody libraries).

In some embodiments, the serotonin receptor function activator is a non-selective serotonin receptor activator (e.g., an agonist that activates two or more serotonin receptors listed in Table 1). Non-selective serotonin receptor activators for use in the methods and compositions described herein are included in Table 2.

In some embodiments, the serotonin receptor function activator activates a serotonin receptor (e.g., multiple serotonin receptors listed in Table 1) by inhibiting or reducing serotonin reuptake or increasing serotonin release. Agents that can be used to inhibit serotonin reuptake include serotonin reuptake inhibitors, serotonin-norepinephrine-dopamine reuptake inhibitors (SNDRIs), and serotonin-norepinephrine reuptake inhibitors (SNRIs). Agents that can be used to increase serotonin release include serotonin releasing agents. Serotonin reuptake inhibitors, SNRIs, SNDRIs, and serotonin releasing agents for use in the methods and compositions described herein are provided in Table 2.

Serotonin Receptor Signaling Activators

In some embodiments, the serotonin receptor activator is a serotonin receptor signaling activator. Serotonin receptor signaling activators include agents that activate or increase signaling that occurs downstream of serotonin receptor activation, such as small molecule activators of intracellular signaling cascades (e.g., activators of G protein signaling, beta arrestin signaling, the phosphatidylinositol-calcium second messenger system, ERK1, ERK2, or MAP kinase). Exemplary small molecule receptor signaling activators for use in the methods and compositions described herein are provided in Table 3.

Neurotransmission Blockers

In some embodiments, the serotonin receptor activator is a neurotransmission blocker. Neurotransmission blockers decrease or block neurotransmission by decreasing neurotransmitter synthesis or release, increasing neurotransmitter reuptake or degradation, decreasing neurotransmitter receptor activity, and/or disrupting the pre- or post-synaptic machinery. In some embodiments, the neurotransmission blocker is a bacterial neurotoxin that stimulates the release of serotonin or neuropeptides. In some embodiments, the neurotoxin is a neurotoxin listed in Table 11. In some embodiments, the neurotoxin is cholera toxin or *Clostridium difficile* toxin A.

TABLE 1

SEROTONIN RECEPTORS

| Receptor | Accession Number (Entrez Gene ID) |
|---|---|
| HTR1A | 3350 |
| HTR1B | 3351 |
| HTR1D | 3352 |
| HTR1E | 3354 |
| HTR1F | 3355 |
| HTR2A | 3356 |
| HTR2B | 3357 |
| HTR2C | 3358 |
| HTR3A | 3359 |
| HTR3B | 9177 |
| HTR3C | 170572 |
| HTR3D | 200909 |
| HTR3E | 285242 |
| HTR4 | 3360 |
| HTR5A | 3361 |
| HRT5BP | 645694 |
| HTR6 | 3362 |
| HTR7 | 3365 |

TABLE 2

SMALL MOLECULE SEROTONIN RECEPTOR ACTIVATORS

| Receptor | Activators |
|---|---|
| HTR1A agonists | azapirones, such as alnespirone, binosperone, buspirone, enilospirone, etapirone, geprione, ipsaprione, revosprione, zalosprione, perosprione, tiosperone, umespirone, and tandospirone; 8-OH-DPAT, befiradol, F-15,599, lesopitron, MKC-242, LY-283,284, osemozotan, repinotan, U-92,016-A, RU-24969, 2C-B, 2C-E, 2C-T-2, aripiprazole, asenapine, bacoside, befiradol, brexpiprazole, bufotenin, cannabidiol, fibanserin |
| HTR1B agonists | triptans, such as sumatriptan, rizatriptan, eletriptan, donitripatn, almotriptan, frovatriptan, avitriptan, zolmitriptan, and naratriptan; ergotamine, 5-carboxamidotryptamine, CGS-12066A, CP-93,129, CP-94,253, CP-122,288, CP-135,807, RU-24969, vortioxetine, ziprasidone, asenapine |
| HTR1D agonists | triptans, such as sumatriptan, rizatriptan, and naratriptan; ergotamine, 5-(nonyloxy)tryptaime, 5-(t-butyl)-N-methyltryptamine, CP-286,601, PNU-109,291, PNU-142,633, GR-46611, L-694,247, L-772,405, CP-122,288, and CP-135,807 |
| HTR1E agonists | BRL-54443, eletriptan |
| HTR1F agonists | Almotriptan Malate, Eletriptan Hydrobromide, Lasmiditan, CHEMBL3617549, CHEMBL3617550, CHEMBL3617557, CHEMBL177238, CHEMBL177258, CHEMBL369705, CHEMBL173949, CHEMBL431041, CHEMBL104720, CHEMBL321080, CHEMBL105261, CHEMBL105955, CHEMBL102250, CHEMBL104753, CHEMBL105958, CHEMBL105722, CHEMBL105091, CHEMBL420475, CHEMBL186951, CHEMBL186662, CHEMBL187581, |

TABLE 2-continued

SMALL MOLECULE SEROTONIN RECEPTOR ACTIVATORS

| Receptor | Activators |
| --- | --- |
| | CHEMBL187308, CHEMBL339980, CHEMBL128, LY-334,370, LY-334,370, 5-n-butyryloxy-DMT, BRL-54443, eletriptan, LY-344,864, naratriptan, lasmiditan |
| HTR2A agonists | 25I-NBOH, O-4310, OSU-6162, 25CN-NBOH, 25I-NBOH, 25I-NBOMe, (R)-DOI, TCB-2, mexamine, O-4310, PHA-57378, OSU-6162, 25CN-NBOH, juncosamine, efavirenz, mefloquine, lisuride, 2C-B |
| HTR2B agonists | Methylergonovine Maleate, CHEMBL2337490, CHEMBL2337493, CHEMBL2337492, CHEMBL494947, CHEMBL2337494, CHEMBL2337106, CHEMBL595195, CHEMBL2337503, CHEMBL2337488, CHEMBL609306, CHEMBL595194, CHEMBL2337500, CHEMBL3416053, CHEMBL2337496, CHEMBL594717, CHEMBL2337105, CHEMBL3416060, CHEMBL595553, CHEMBL3416039, CHEMBL593545, CHEMBL3416056, CHEMBL3416061, CHEMBL3416047, CHEMBL2337499, CHEMBL594469, CHEMBL3416040, CHEMBL1093699, CHEMBL3416046, CHEMBL3416049, CHEMBL27, CHEMBL3736433, CHEMBL3736156, CHEMBL3416041, CHEMBL3416042, fenfluramine, pergolide, cabergoline, mefloquine, BW-723086, Ro60-0175, VER-3323, 6-APB, guanfacine, norfenfluramine, 5-MeO-DMT, DMT, mCPP, aminorex, chlorphentermine, MEM, MDA, LSD, psilocin, MDMA |
| HTR2C agonists | |
| | CHEMBL1091452, CHEMBL1092029, CHEMBL1092167, CHEMBL1093699, CHEMBL1628670, CHEMBL170319, CHEMBL170854, CHEMBL171774, CHEMBL172159, CHEMBL1901802, CHEMBL2011548, CHEMBL2011553, CHEMBL2011556, CHEMBL2011564, CHEMBL2011565, CHEMBL2011566, CHEMBL2011567, CHEMBL2011569, CHEMBL2011570, CHEMBL203013, CHEMBL208936, CHEMBL209106, CHEMBL209155, CHEMBL209254, CHEMBL209714, CHEMBL210215, CHEMBL210484, CHEMBL210802, CHEMBL2110670, CHEMBL211153, CHEMBL2260565, CHEMBL2260567, CHEMBL2260568, CHEMBL2260569, CHEMBL2337102, CHEMBL2337103, CHEMBL2337104, CHEMBL2337105, CHEMBL2337106, CHEMBL2337488, CHEMBL2337489, CHEMBL2337490, CHEMBL2337491, CHEMBL2337492, CHEMBL2337493, CHEMBL2337494, CHEMBL2337495, CHEMBL2337496, CHEMBL2337497, CHEMBL2337498, CHEMBL2337499, CHEMBL2337500, CHEMBL2337501, CHEMBL2337502, CHEMBL2337503, CHEMBL2337504, CHEMBL2391541, CHEMBL2396668, CHEMBL2397877, CHEMBL2397879, CHEMBL2397884, CHEMBL2397895, CHEMBL2397896, CHEMBL2397901, CHEMBL2397902, CHEMBL2397905, CHEMBL2397906, CHEMBL2397908, CHEMBL2397915, CHEMBL303516, CHEMBL30713, CHEMBL309760, CHEMBL3416032, CHEMBL3416033, CHEMBL3416034, CHEMBL3416035, CHEMBL3416036, CHEMBL3416037, CHEMBL3416038, CHEMBL3416039, CHEMBL3416040, CHEMBL3416041, CHEMBL3416042, CHEMBL3416043, CHEMBL3416044, CHEMBL3416045, CHEMBL3416046, CHEMBL3416047, CHEMBL3416048, CHEMBL3416049, CHEMBL3416051, CHEMBL3416053, CHEMBL3416054, CHEMBL3416055, CHEMBL3416056, CHEMBL3416057, CHEMBL3416058, CHEMBL3416059, CHEMBL3416060, CHEMBL3416061, CHEMBL3416062, CHEMBL3416063, CHEMBL3416064, CHEMBL3416065, CHEMBL3416066, CHEMBL3416067, CHEMBL353998, CHEMBL355474, CHEMBL3589578, CHEMBL3589582, CHEMBL3589595, CHEMBL360328, CHEMBL379819, CHEMBL379983, CHEMBL39, CHEMBL407909, CHEMBL425423, CHEMBL425777, CHEMBL438611, CHEMBL451543, CHEMBL478, CHEMBL494947, CHEMBL593545, CHEMBL593547, CHEMBL594469, CHEMBL594477, CHEMBL594489, CHEMBL594717, CHEMBL594718, CHEMBL595194, CHEMBL595195, CHEMBL595196, CHEMBL595553, CHEMBL595554, CHEMBL595555, CHEMBL595645, CHEMBL595646, CHEMBL596108, CHEMBL596327, CHEMBL596328, CHEMBL608135, CHEMBL609306, CHEMBL609595, CHEMBL6616, CHEMBL76301, CHEMBL76307, CHEMBL76474, CHEMBL76781, CHEMBL77880, CHEMBL80246, CHEMBL80366, CHEMBL80482, CHEMBL80731, CHEMBL80862, lorcaserin, lisuride, A-372,159, AL-38022A, CP-809,101, fenfluramine, mesulergine, MK-212, naphthyllisopropylamine, norfenfluramine, ORG-12,962, ORG-37,684, oxaflozane, PNU-22395, PNU-181731, lysergamides, phenethylamines, piperazines, tryptamines, Ro60-0175, vabicaserin, WAY-629, WAY-161,503, WAY-163,909, and YM-348 |
| HTR3A agonists | CHEMBL53929, CHEMBL11608, CHEMBL429317, CHEMBL402757, CHEMBL254352, CHEMBL257155, CHEMBL402540, CHEMBL3769507, CHEMBL2204360, CHEMBL3261479, CHEMBL3261482, CHEMBL3261481, CHEMBL3261485, CH EMBL3261486, CH EMBL3261483, CHEMBL1643882, CHEMBL1643881, CHEMBL1643884, CHEMBL46, CHEMBL1110, CHEMBL289469, CHEMBL1189679, CHEMBL1110, CHEMBL289469, CHEMBL1643880, CH EMBL1643882, CH EMBL1643882, CH EMBL1643884, CHEMBL46, CHEMBL1110, CHEMBL1189679, CHEMBL1643881, CHEMBL1643895, CHEMBL289469, CHEMBL1643880, 2-methyl-5-HT, alpha-methyltryptamine, bufotenin, chlorophenylbiguanide, ethanol, ibogaine, phenylbiguanide, quipazine, RS-56812, SR-57227, varenicline, YM-31636 |
| HTR4 agonists | cisapride, tegaserod, prucalopride, BIMU-8, CJ-033,466, ML-10302, mosapride, renzapride, RS-67506, RS-67333, SL65.1055, zacopride, metoclopramide, sulpride |

TABLE 2-continued

SMALL MOLECULE SEROTONIN RECEPTOR ACTIVATORS

| Receptor | Activators |
| --- | --- |
| HTR6 agonists | CHEMBL1950351, CHEMBL179408, CHEMBL368209, CHEMBL180425, CHEMBL179926, CHEMBL369759, CHEMBL175471, CHEMBL3633184, CHEMBL1950776, CHEMBL1950775, CHEMBL1950760, CHEMBL1950774, CHEMBL1950773, CHEMBL1950776, CHEMBL1950760, CHEMBL1950750, CHEMBL1950775, CHEMBL1950773, CHEMBL1950774, CHEMBL1950750, CHEMBL1950762, CHEMBL2376482, CHEMBL2376483, CHEMBL520795, CHEMBL520129, CHEMBL482562, CHEMBL566410, CHEMBL566219, CHEMBL578411, CHEMBL566218, CHEMBL566213, CHEMBL571762, CHEMBL3289978, CHEMBL3290016, CHEMBL3289995, CHEMBL3289954, CHEMBL3290014, CHEMBL3290006, CHEMBL3289991, CHEMBL3290017, CHEMBL3290008, CHEMBL3290012, CHEMBL3289993, CHEMBL3290003, CHEMBL506736, CHEMBL506736, CHEMBL506736, CHEMBL579981, CHEMBL176292, CHEMBL362628, CHEMBL179407, CHEMBL175884, CHEMBL368390, CHEMBL427134, CHEMBL177124, CHEMBL176028, CHEMBL2376487, CHEMBL2376485, CHEMBL26379, CHEMBL1550957, CHEMBL2376484, CHEMBL2376486, CHEMBL2413988, EMDT, WAY-181,187, WAY-208,466, N-(inden-5-yl)imidazothiazole-5-sulfonamide, E-6837, E-6801, and EMD-386,088 |
| HTR7 agonists | CHEMBL39, CHEMBL3321798, CHEMBL3321794, CHEMBL445334, CHEMBL18840, CHEMBL222755, CHEMBL389718, CHEMBL225284, CHEMBL371300, CHEMBL224820, AS-19, 5-CT, 5-MeOT, 8-OH-DAPT, aripiprazole, E-55888, E-57431, LP-12, LP-44, MSD-5a, RA-7, and N,N-Dimethyltryptamine |
| Serotonin reuptake inhibitors | Alaproclate, cericlamine, citalopram, dapoxetine, escitalopram, femoxetine, fluoxetine, fluvoxamine, ifoxetine, indalpine, omiloxetine, panuramine, paroxetine, pirandamine, RTI-353, sertraline, zimelidine, desmethylcitalopram, didesmethylcitalopram, seproxetine ((S)-norfluoxetine), desvenlafaxine, cianopramine, litoxetine, lubazodone, SB-649,915, trazodone, vilazodone, vortioxetine, dextromethorphan, dextropropoxyphene, dimenhydrinate, diphenhydramine, mepyramine (pyrilamine), mifepristone, delucemine, mesembrenone, mesembrine, roxindole, duloxetine, levomilnacipran, milnacipran, dapoxetine, sibutramine, chlorpheniramine, dextropmethorphan, methadone |
| Serotonin-norepinephrine-dopamine reuptake inhibitors (SNDRIs) and serotonin-norepinephrine reuptake inhibitors (SNRIs) | Mazindol, nefazodone, sibutramine, venlafaxine, esketamine, duloxetine, ketamine, phencyclidine, tripelennamine, mepiprazole, amitifadine, AN788, ansofaxine, centanafadine, atomoxetine, desvenlafaxine, milnacipran, levomilnacipran, dasotraline, Lu AA34893, Lu AA37096, NS-2360, tedatioxetine, tesofensine, bicifadine, BMS-866,949, brasofensine, diclofensine, DOV-216,303, EXP-561, liafensine, NS-2359, RG-7166, SEP-227,162, SEP-228,425, SEP-228,432, naphyrone, 3,3-Diphenylcyclobutanamine, 3,4-Dichlorotametraline, D-161, desmethylsertraline, DMNPC, DOV-102,677, fezolamine, GSK1360707F, indatraline, JNJ-7925476, JZ-IV-10, JZAD-IV-22, LR-5182, methylnaphthidate, MI-4, PRC200-SS, PRC050, PRC025, SKF-83,959, TP1, phenyltropanes (e.g., WF-23, dichloropane, and RTI-55), *Ginkgo biloba* extract, St John's Wort, hyperforin, adhyperforin, and uliginosin B |
| Serotonin releasing agents | Cloforex, dexfenfluramine, etolorex, fenfluramine, flucetorex, indeloxazine, levofenfluramine, tramadol, carbamazepine, amiflamine (FLA-336), viqualine (PK-5078), 2-Methyl-3,4-methylenedioxyamphetamine (2-Methyl-MDA), 3-Methoxy-4-methylamphetamine (MMA), 3-Methyl-4,5-methylenedioxyamphetamine (5-Methyl-MDA), 3,4-Ethylenedioxy-N-methylamphetamine (EDMA), 4-Methoxyamphetamine (PMA), 4-Methoxy-N-ethylamphetamine (PMEA), 4-Methoxy-N-methylamphetamine (PMMA), 4-Methylthioamphetamine (4-MTA), 5-(2-Aminopropyl)-2,3-dihydrobenzofuran (5-APDB), 5-Indanyl-2-aminopropane (IAP), 5-Methoxy-6-methylaminoindane (MMAI), 5-Trifluoromethyl-2-aminoindane (TAI), 5,6-Methylenedioxy-2-aminoindane (MDAI), 5,6-Methylenedioxy-N-methyl-2-aminoindane (MDMAI), 6-Chloro-2-aminotetralin (6-CAT), 6-Tetralinyl-2-aminopropane (TAP), 6,7-Methylenedioxy-2-aminotetralin (MDAT), 6,7-Methylenedioxy-N-methyl-2-aminotetralin (MDMAT), N-Ethyl-5-trifluoromethyl-2-aminoindane (ETAI), N-Methyl-5-indanyl-2-aminopropane, aminorex, MDEA, MBDB, αMT, 5MeO-NMT, NMT, NETP, Dimethyl-Serotonin, 5MeO-NET, αET and αMT |

TABLE 3

SEROTONIN RECEPTOR SIGNALING ACTIVATORS

| Signaling protein or pathway | Activators |
| --- | --- |
| ERK1, ERK2 MAPK | Ceramide C6, t-butylhydroquinone JNK activators (e.g., Anisomycin), p38 MAPK inhibitors (e.g., U-46619, AEBSF hydrochloride) |

Agent Modalities

A serotonin receptor activator can be selected from a number of different modalities. A serotonin receptor activator can be a nucleic acid molecule (e.g., DNA molecule or RNA molecule, e.g., mRNA), a small molecule (e.g., a small molecule serotonin receptor activator, an activator of a signaling cascade, or an epigenetic modifier), or a polypeptide (e.g., an antibody molecule or antibody-like molecule, e.g., an antibody or antigen binding fragment thereof). A serotonin receptor activator can also be a viral vector expressing a serotonin receptor activator (e.g., a neurotoxin) or a cell infected with a viral vector. Any of these modalities can be a serotonin receptor activator directed to target (e.g., to increase or activate) serotonin receptor function, serotonin receptor expression, serotonin receptor binding, or serotonin receptor signaling.

The nucleic acid molecule, small molecule, peptide, polypeptide, or antibody molecule can be modified. For example, the modification can be a chemical modification, e.g., conjugation to a marker, e.g., fluorescent marker or a radioactive marker. In other examples, the modification can include conjugation to a molecule that enhances the stability or half-life of the serotonin receptor activator (e.g., an Fc domain of an antibody or serum albumin, e.g., human serum albumin). The modification can also include conjugation to an antibody to target the agent to a particular cell or tissue. Additionally, the modification can be a chemical modification, packaging modification (e.g., packaging within a nanoparticle or microparticle), or targeting modification to prevent the agent from crossing the blood brain barrier.

Small Molecules

Numerous small molecule serotonin receptor activators useful in the methods of the invention are described herein (e.g., listed in Table 2) and additional small molecule serotonin receptor activators useful as therapies for inflammatory or autoimmune disease or condition can also be identified through screening based on their ability to activate or increase serotonin receptor function or signaling. Small molecules include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heterorganic and organometallic compounds) generally having a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds.

Serotonin receptor activators can be used to treat a disorder or condition described herein. A pharmaceutical composition containing the serotonin receptor activator can be formulated for treatment of an inflammatory or autoimmune disease or condition described herein. In some embodiments, a pharmaceutical composition that includes the serotonin receptor activator is formulated for local administration, e.g., to the affected site in a subject.

Antibodies

The serotonin receptor activator can be an antibody or antigen binding fragment thereof. For example, a serotonin receptor activator described herein is an antibody that activates or induces the activity and/or function of serotonin receptor through binding to a serotonin receptor to activate the serotonin receptor (e.g., agonize the receptor).

The making and use of therapeutic antibodies against a target antigen (e.g., against a serotonin receptor listed in Table 1, e.g., HTR1F, HTR2B, HTR2C, HTR3A, HTR6, or HTR7) is known in the art. See, for example, the references cited herein above, as well as Zhiqiang An (Editor), Therapeutic Monoclonal Antibodies: From Bench to Clinic. 1st Edition. Wiley 2009, and also Greenfield (Ed.), Antibodies: A Laboratory Manual. (Second edition) Cold Spring Harbor Laboratory Press 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

Viral Vectors

The serotonin receptor activator can be delivered by a viral vector (e.g., a viral vector expressing a neurotoxin, e.g., a neurotoxin listed in Table 11). A viral vector expressing a neurotoxin from Table 11 or neurotoxins DON or pertussis toxin can be administered to a cell or to a subject (e.g., a human subject or animal model) to modulate neurotransmission. Viral vectors can be directly administered (e.g., injected) to a site of inflammation to treat an inflammatory or autoimmune disease or condition.

Viral genomes provide a rich source of vectors that can be used for the efficient delivery of exogenous genes into a mammalian cell. Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus, replication deficient herpes virus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology (Third Edition) Lippincott-Raven, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the teachings of which are incorporated herein by reference.

Cell-Based Therapies

A serotonin receptor activator described herein can be administered to a cell in vitro (e.g., an immune cell), which can subsequently be administered to a subject (e.g., a human subject or animal model). The serotonin receptor activator can be administered to the cell to effect an immune response (e.g., deactivation, polarization, antigen presentation, tolerance, cytokine suppression, migration, senescence, or differentiation) as described herein. Once the immune response is elicited, the cell can be administered to a subject (e.g., injected) to treat an autoimmune or inflammatory disease or condition. The immune cell can be locally administered (e.g., injected into a spleen, lymph node, primary, secondary, or tertiary lymphoid organ, or a site of inflammation).

A serotonin receptor activator can also be administered to a cell in vitro (e.g., an immune cell) to alter gene expression in the cell. The serotonin receptor activator can increase the expression of one or more serotonin receptors in an immune cell. The serotonin receptor activator can be an exogenous gene encoded by a plasmid that is introduced into the cell using standard methods (e.g., calcium phosphate precipitation, electroporation, microinjection, infection, lipofection, impalefection, laserfection, or magnetofection). The serotonin receptor activator can be a viral vector (e.g., a viral vector expressing a serotonin receptor activator) that is introduced to the cell using standard transduction methods. The plasmid or vector can also contain a reporter construct (e.g., a fluorescent reporter) that can be used to confirm expression of the transgene by the immune cell has been contacted with a serotonin receptor activator to increase gene or protein expression, the cell can be administered to a subject (e.g., injected) to treat an autoimmune or inflammatory disease or condition. The immune cell can be locally administered (e.g., injected into a spleen, lymph node, primary, secondary, or tertiary lymphoid organ, barrier tissue, or a site of inflammation).

The cell can be administered to a subject immediately after being contacted with a serotonin receptor activator (e.g., within 5, 10, 15, 30, 45, or 60 minutes of being contacted with a serotonin receptor activator), or 6 hours, 12 hours, 24 hours, 2 days, 3, days, 4 days, 5, days, 6 days, 7 days or more after being contacted with a serotonin receptor activator. The method can include an additional step of evaluating the immune cell for an immune cell activity (e.g., activation, polarization, antigen presentation, cytokine production, migration, proliferation, or differentiation) or modulation of gene expression after contact with a serotonin receptor activator and before administration to a subject.

Blood Brain Barrier Permeability

In some embodiments, the serotonin receptor activators for use in the present invention are agents that are not capable of crossing, or that do not cross, the blood brain barrier (BBB) of a mammal, e.g., an experimental rodent (e.g., mouse or rat), dog, pig, non-human primate, or a human. The BBB is a highly selective semipermeable membrane barrier that separates the circulating blood from the brain extracellular fluid (e.g., cerebrospinal fluid) in the central nervous system (CNS). The BBB is made up of high-density endothelial cells, which are connected by tight junctions. These cells prevent most molecular compounds in the bloodstream (e.g., large molecules and hydrophilic molecules) from entering the brain. Water, some gases (e.g., oxygen and carbon dioxide), and lipid-soluble molecules (e.g., hydrophobic molecules, such as steroid hormones) can cross the BBB by passive diffusion. Molecules that are needed for neural function, such as glucose and amino acids, are actively transported across the BBB.

A number of approaches can be used to render an agent BBB impermeable. These methods include modifications to increase an agent's size, polarity, or flexibility or reduce its lipophilicity, targeting approaches to direct an agent to another part of the body and away from the brain, and packaging approaches to deliver an agent in a form that does not freely diffuse across the BBB. These approaches can be used to render a BBB permeable serotonin receptor activator impermeable, and they can also be used to improve the properties (e.g., cell-specific targeting) of a serotonin receptor activator that does not cross the BBB. The methods that can be used to render an agent BBB impermeable are discussed in greater detail herein below.

Formulation of BBB-Impermeable Agents for Enhanced Cell Targeting

One approach that can be used to render a serotonin receptor activator BBB impermeable is to conjugate the agent to a targeting moiety that directs it somewhere other than the brain. The targeting moiety can be an antibody for a receptor expressed by the target cell (e.g., N-Acetylgalactosamine for liver transport; DGCR2, GBF1, GPR44 or SerpinB10 for pancreas transport; Secretoglobin, family 1A, member 1 for lung transport). The targeting moiety can also be a ligand of any receptor or other molecular identifier expressed on the target cell in the periphery. These targeting moieties can direct the serotonin receptor activator of interest to its corresponding target cell, and can also prevent BBB crossing by directing the agent away from the BBB and increasing the size of the serotonin receptor activator via conjugation of the targeting moiety.

Serotonin receptor activators can also be rendered BBB impermeable through formulation in a particulate delivery system (e.g., a nanoparticle, liposome, or microparticle), such that the agent is not freely diffusible in blood and cannot cross the BBB. The particulate formulation used can be chosen based on the desired localization of the serotonin receptor activator (e.g., a lymph node, lymphoid organ, or site of inflammation), as particles of different sizes accumulate in different locations. For example, nanoparticles with a diameter of 45 nm or less enter the lymph node, while 100 nm nanoparticles exhibit poor lymph node trafficking. Some examples of the link between particle size and localization in vivo are described in Reddy et al., J Controlled Release 112:26 2006, and Reddy et al., Nature Biotechnology 25:1159 2007.

Serotonin receptor activators can be tested after the addition of a targeting moiety or after formulation in a particulate delivery system to determine whether or not they cross the BBB. Models for assessing BBB permeability include in vitro models (e.g., monolayer models, co-culture models, dynamic models, multi-fluidic models, isolated brain microvessels), in vivo models, and computational models as described in He et al., Stroke 45:2514 2014; Bickel, NeuroRx 2:15 2005; and Wang et al., Int J Pharm 288:349 2005. A serotonin receptor activator that exhibits BBB impermeability can be used in the methods described herein.

Modification of Existing Compounds to Render them BBB Impermeable

There are multiple parameters that have been empirically derived in the field of medicinal chemistry to predict whether a compound will cross the BBB. The most common numeric value for describing permeability across the BBB is the log BB, defined as the logarithmic ratio of the concentration of a compound in the brain and in the blood. Empirical rules of thumb have been developed to predict BBB permeability, including rules regarding molecular size, polar surface area, sum of oxygen and nitrogen atoms, lipophilicity (e.g., partition coefficient between apolar solvent and water), "lipoaffinity", molecular flexibility, and number of rotatable bonds (summarized in Muehlbacher et al., J Comput Aided Mol Des. 25: 1095 2011; and Geldenhuys et al., Ther Deliv. 6: 961 2015). Some preferred limits on various parameters for BBB permeability are listed in Table 1 of Ghose et al., ACS Chem Neurosci. 3: 50 2012, which is incorporated herein by reference. Based on the parameters shown in the table, one of skill in the art could modify an existing serotonin receptor activator to render it BBB impermeable.

One method of modifying a serotonin receptor activator to prevent BBB crossing is to add a molecular adduct that does not affect the target binding specificity, kinetics, or thermodynamics of the agent. Molecular adducts that can be used to render an agent BBB impermeable include polyethylene glycol (PEG), a carbohydrate monomer or polymer, a dendrimer, a polypeptide, a charged ion, a hydrophilic group, deuterium, and fluorine. Serotonin receptor activators can be tested after the addition of one or more molecular adducts or after any other properties are altered to determine whether or not they cross the BBB. Models for assessing BBB permeability include in vitro models (e.g., monolayer models, co-culture models, dynamic models, multi-fluidic models, isolated brain microvessels), in vivo models, and computational models as described in He et al., Stroke 45:2514 2014; Bickel, NeuroRx 2:15 2005; and Wang et al., Int J Pharm 288:349 2005. A serotonin receptor activator that exhibits BBB impermeability can be used in the methods described herein.

Screening for or Development of BBB Impermeable Agents

Another option for developing BBB impermeable agents is to find or develop new agents that do not cross the BBB. One method for finding new BBB impermeable agents is to screen for compounds that are BBB impermeable. Compound screening can be performed using in vitro models (e.g., monolayer models, co-culture models, dynamic models, multi-fluidic models, isolated brain microvessels), in vivo models, and computational models, as described in He et al., Stroke 45:2514 2014; Bickel, NeuroRx 2:15 2005; Wang et al., Int J Pharm 288:349 2005, and Czupalla et al., Methods Mol Biol 1135:415 2014. For example, the ability of a molecule to cross the blood brain barrier can be determined in vitro using a transwell BBB assay in which microvascular endothelial cells and pericytes are co-cultured separated by a thin macroporous membrane, see e.g., Naik et al., J Pharm Sci 101:1337 2012 and Hanada et al., Int J Mol Sci 15:1812 2014; or in vivo by tracking the brain uptake of the target molecule by histology or radio-detection. Compounds would be deemed appropriate for use as serotonin receptor activators in the methods described herein if they do not display BBB permeability in the aforementioned models.

Modulation of Immune Cells

The methods described herein can be used to modulate an immune response in a subject or cell by administering to a subject or cell a serotonin receptor activator in a dose (e.g., an effective amount) and for a time sufficient to modulate the immune response. These methods can be used to treat a subject in need of modulating an immune response, e.g., a subject with an inflammatory condition, an autoimmune disease or condition. One way to modulate an immune response is to modulate an immune cell activity. This modulation can occur in vivo (e.g., in a human subject or animal model) or in vitro (e.g., in acutely isolated or cultured cells, such as human cells from a patient, repository, or cell line, or rodent cells). The types of cells that can be modulated include T cells (e.g., peripheral T cells, cytotoxic T cells/CD8+ T cells, T helper cells/CD4+ T cells, memory T cells, regulatory T cells/Tregs, natural killer T cells/NKTs, mucosal associated invariant T cells, and gamma delta T cells), B cells (e.g., memory B cells, plasmablasts, plasma cells, follicular B cells/B-2 cells, marginal zone B cells, B-1 cells, regulatory B cells/Bregs), dendritic cells (e.g., myeloid DCs/conventional DCs, plasmacytoid DCs, or follicular DCs), granulocytes (e.g., eosinophils, mast cells, neutrophils, and basophils), monocytes, macrophages (e.g., peripheral macrophages or tissue resident macrophages), myeloid-derived suppressor cells (MDSCs), NK cells, innate lymphoid cells (ILC1, ILC2, or ILC3 cells), thymocytes, and megakaryocytes.

The immune cell activities that can be modulated by administering to a subject or contacting a cell with an effective amount of a serotonin receptor activator described herein include activation (e.g., macrophage, T cell, NK cell, ILC, B cell, dendritic cell, neutrophil, eosinophil, or basophil activation), phagocytosis (e.g., macrophage, neutrophil, monocyte, mast cell, B cell, eosinophil, or dendritic cell phagocytosis), antibody-dependent cellular phagocytosis (e.g., ADCP by monocytes, macrophages, neutrophils, or dendritic cells), antibody-dependent cellular cytotoxicity (e.g., ADCC by NK cells, ILCs, monocytes, macrophages, neutrophils, eosinophils, dendritic cells, or T cells), polarization (e.g., macrophage polarization toward an M1 or M2 phenotype or T cell polarization), proliferation (e.g., proliferation of B cells, T cells, monocytes, macrophages, dendritic cells, NK cells, ILCs, mast cells, neutrophils, eosinophils, or basophils), lymph node homing (e.g., lymph node homing of T cells, B cells, dendritic cells, or macrophages), lymph node egress (e.g., lymph node egress of T cells, B cells, dendritic cells, or macrophages), recruitment (e.g., recruitment of B cells, T cells, monocytes, macrophages, dendritic cells, NK cells, ILCs, mast cells, neutrophils, eosinophils, or basophils), migration (e.g., migration of B cells, T cells, monocytes, macrophages, dendritic cells, NK cells, ILCs, mast cells, neutrophils, eosinophils, or basophils), differentiation (e.g., regulatory T cell differentiation), immune cell cytokine production, antigen presentation (e.g., dendritic cell, macrophage, and B cell antigen presentation), maturation (e.g., dendritic cell maturation), and degranulation (e.g., mast cell, NK cell, ILC, cytotoxic T cell, neutrophil, eosinophil, or basophil degranulation). Innervation of lymph nodes or lymphoid organs, development of high endothelial venules (HEVs), and development of ectopic or tertiary lymphoid organs (TLOs) can also be modulated using the methods described herein. Modulation can increase or decrease these activities, depending on the serotonin receptor activator used to contact the cell or treat a subject.

In some embodiments, an effective amount of a serotonin receptor activator is an amount sufficient to modulate (e.g., increase or decrease) one or more (e.g., 2 or more, 3 or more, 4 or more) of the following immune cell activities in the subject or cell: T cell polarization; T cell activation; dendritic cell activation; neutrophil activation; eosinophil activation; basophil activation; T cell proliferation; B cell proliferation; T cell proliferation; monocyte proliferation; macrophage proliferation; dendritic cell proliferation; NK cell proliferation; ILC proliferation; mast cell proliferation; neutrophil proliferation; eosinophil proliferation; basophil proliferation; cytotoxic T cell activation; circulating monocytes; peripheral blood hematopoietic stem cells; macrophage polarization; macrophage phagocytosis; macrophage ADCP, neutrophil phagocytosis; monocyte phagocytosis; mast cell phagocytosis; B cell phagocytosis; eosinophil phagocytosis; dendritic cell phagocytosis; macrophage activation; antigen presentation (e.g., dendritic cell, macrophage, and B cell antigen presentation); antigen presenting cell migration (e.g., dendritic cell, macrophage, and B cell migration); lymph node immune cell homing and cell egress (e.g., lymph node homing and egress of T cells, B cells, dendritic cells, or macrophages); NK cell activation; NK cell ADCC, mast cell degranulation; NK cell degranulation; ILC activation; ILC ADCC, ILC degranulation; cytotoxic T cell degranulation; neutrophil degranulation; eosinophil degranulation; basophil degranulation; neutrophil recruitment; eosinophil recruitment; NKT cell activation; B cell activation; regulatory T cell differentiation; dendritic cell maturation; development of high endothelial venules (HEVs); development of ectopic or tertiary lymphoid organs (TLOs); or lymph node or secondary lymphoid organ innervation. In certain embodiments, the immune response (e.g., an immune cell activity listed herein) is decreased in the subject or cell at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the immune response is decreased in the subject or cell between 5-20%, between 5-50%, between 10-50%, between 20-80%, between 20-70%, between 50-200%, between 100%-500%.

After a serotonin receptor activator is administered to treat a patient or contact a cell, a readout can be used to assess the effect on immune cell activity. Immune cell activity can be assessed by measuring a cytokine or marker associated with a particular immune cell type, as listed in Table 4 (e.g., performing an assay listed in Table 4 for the cytokine or marker). In certain embodiments, the parameter is decreased in the subject at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the parameter is decreased in the subject between 5-20%, between 5-50%, between 10-50%, between 20-80%, between 20-70%, between 50-200%, between 100%-500%. A serotonin receptor activator can be administered at a dose (e.g., an effective amount) and for a time sufficient to modulate an immune cell activity described herein below.

After a serotonin receptor activator is administered to treat a patient or contact a cell, a readout can be used to assess the effect on immune cell migration. Immune cell migration can be assessed by measuring the number of immune cells in a location of interest (e.g., a spleen, lymph node, primary, secondary, or tertiary lymphoid organ, or a site of inflammation). Immune cell migration can also be assessed by measuring a chemokine, receptor, or marker associated with immune cell migration, as listed in Tables 5 and 6. In certain embodiments, the parameter is decreased in the subject at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the parameter is decreased in the subject between 5-20%, between 5-50%, between 10-50%, between 20-80%, between 20-70%, between 50-200%, between 100%-500%. A serotonin receptor activator can be administered at a dose (e.g., an effective amount) and for a time sufficient to modulate an immune cell migration as described herein below.

A serotonin receptor activator described herein can affect immune cell migration. Immune cell migration between peripheral tissues, the blood, and the lymphatic system as well as lymphoid organs is essential for the orchestration of productive innate and adaptive immune responses. Immune cell migration is largely regulated by trafficking molecules including integrins, immunoglobulin cell-adhesion molecules (IgSF CAMs), cadherins, selectins, and a family of small cytokines called chemokines (Table 5). Cell adhesion molecules and chemokines regulate immune cell migration by both inducing extravasation from the circulation into peripheral tissues and acting as guidance cues within peripheral tissues themselves. For extravasation to occur, chemokines must act in concert with multiple trafficking molecules including C-type lectins (L-, P-, and E-selectin), multiple integrins, and cell adhesion molecules (ICAM-1, VCAM-1 and MAdCAM-1) to enable a multi-step cascade of immune cell capturing, rolling, arrest, and transmigration via the blood endothelial barrier (Table 6). Some trafficking molecules are constitutively expressed and manage the migration of immune cells during homeostasis, while others are specifically upregulated by inflammatory processes such as infection and autoimmunity.

The expression of trafficking molecules important for extravasation is mainly regulated on specialized blood vessels called HEVs, which are the entry portals from the circulation into the periphery and are usually present in secondary lymphoid organs (SLOs) and chronically inflamed tissue. Chronically inflamed tissues often develop lymphoid-like structures called TLOs that contain structures resembling SLOs including HEVs, lymphoid stromal cells, and confined compartments of T and B lymphocytes. As they can act as major gateways for immune cell migration into peripheral tissues, TLOs have been shown to be important in the pathogenesis of autoimmune disorders.

Once within peripheral tissues, four modes of immune cell migration have been observed: 1) chemokinesis: migration driven by soluble chemokines, without concentration gradients to provide directional bias, 2) haptokinesis: migration along surfaces presenting immobilized ligands such as chemokines or integrins, without concentration gradients to provide directional bias, 3) chemotaxis: directional migration driven by concentration gradients of soluble chemokines, and 4) haptotaxis: directional migration along surfaces presenting gradients of immobilized ligands such as chemokines or integrins. The response of immune cells to trafficking molecules present on the endothelium depends on the composition, expression, and/or functional activity of their cognate receptors, which in turn depends on activation state and immune cell subtype.

Innate immune cells generally migrate toward inflammation-induced trafficking molecules in the periphery. In contrast, naïve T and B cells constantly re-circulate between the blood and secondary lymphoid organs to screen for their cognate antigen presented by activated dendritic cells (DCs) or fibroblastic reticular cells (FRCs), respectively. If activated by recognition of their cognate antigen and appropriate co-stimulation within SLOs, both cell types undergo a series of complex maturation steps, including differentiation and proliferation, ultimately leading to effector and memory immune cell phenotypes. To reach their peripheral target sites, certain effector and memory T and B cell subsets egress from SLOs to the blood circulation via efferent lymphatics. In order to do so, they migrate toward a Sphingosine-1-phosphate (S1P) gradient sensed using their Sphingosine-1-phosphate receptor 1 (S1P$_1$ or S1PR1). For successful egress into efferent lymphatics, immune cells need to overcome SLO retention signals through the CCR7/CCL21 axis or through CD69-mediated downregulation of S1P$_1$.

Finally, certain immune cell subsets, for example mature dendritic cells (DCs) and memory T cells, migrate from peripheral tissues into SLOs via afferent lymphatics. To exit from peripheral tissues and enter afferent lymphatics, immune cells again largely depend on the CCR7/CCL21 and S1P$_1$/S1P axis. Specifically, immune cells need to overcome retention signals delivered via the CCR7/CCL21 axis, and migrate toward an S1P gradient established by the lymphatic endothelial cells using S1P$_1$. The selective action of trafficking molecules on distinct immune cell subsets as well as the distinct spatial and temporal expression patterns of both the ligands and receptors are crucial for the fine-tuning of immune responses during homeostasis and disease.

Aberrant immune cell migration is observed in multiple immune-related pathologies. Immune cell adhesion deficiencies, caused by molecular defects in integrin expression, fucosylation of selectin ligands, or inside-out activation of integrins on leukocytes and platelets, lead to impaired immune cell migration into peripheral tissues. This results in leukocytosis and in increased susceptibility to recurrent bacterial and fungal infections, which can be difficult to treat and potentially life-threatening. Alternatively, exaggerated migration of specific immune cell subsets into specific peripheral tissues is associated with a multitude of pathologies. For example, excessive neutrophil accumulation in peripheral tissues contributes to the development of ischemia-reperfusion injury, such as that observed during acute myocardial infarction, stroke, shock and acute respiratory distress syndrome. Excessive Th1 inflammation characterized by tissue infiltration of interferon-gamma secreting effector T cells and activated macrophages is associated with atherosclerosis, allograft rejection, hepatitis, and multiple autoimmune diseases including multiple sclerosis, rheumatoid arthritis, psoriasis, Crohn's disease, type 1 diabetes and lupus erythematodes. Excessive Th2 inflammation characterized by tissue infiltration of IL-4, IL-5, and IL-13 secreting Th2 cells, eosinophils and mast cells is associated with asthma, food allergies and atopic dermatitis.

In some embodiments, a serotonin receptor activator described herein increases macrophage lymph node homing and/or improves organ function. In some embodiments, a serotonin receptor activator described herein decreases one or more of macrophage migration, macrophage proliferation, macrophage recruitment, macrophage lymph node egress, macrophage differentiation, macrophage activation, macrophage polarization, macrophage cytokine production, macrophage maturation, macrophage antigen presentation, macrophage serotonin receptor expression (e.g., expression of one or more serotonin receptors listed in Table 1, e.g., HTR1F, HTR2B, HTR2C, HTR3A, HTR6, and/or HTR7), macrophage ADCC, or macrophage ADCP. In some embodiments, the cytokine is a pro-inflammatory cytokine (e.g., IL-8). In some embodiments, a serotonin receptor activator described herein decreases inflammation, auto-antibody levels, or the rate or number of relapses or flare-ups.

In some embodiments, a serotonin receptor activator described herein increases T cell lymph node homing and/or improves organ function. In some embodiments, a serotonin receptor activator described herein decreases one or more of T cell migration, T cell proliferation, T cell recruitment, T cell lymph node egress, T cell differentiation, T cell activation, T cell polarization, T cell cytokine production, T cell maturation, T cell antigen presentation, T cell expression of one or more serotonin receptors (e.g., expression of one or more serotonin receptors listed in Table 1, e.g., HTR1F, HTR2B, HTR2C, HTR3A, HTR6, and/or HTR7), T cell ADCC, or T cell ADCP. In some embodiments, the cytokine is a pro-inflammatory cytokine (e.g., IL-8). In some embodiments, a serotonin receptor activator described herein decreases inflammation, auto-antibody levels, or the rate or number of relapses or flare-ups.

In some embodiments, a serotonin receptor activator described herein increases dendritic cell lymph node homing and/or improves organ function. In some embodiments, a serotonin receptor activator described herein decreases one or more of dendritic cell migration, dendritic cell proliferation, dendritic cell recruitment, dendritic cell lymph node egress, dendritic cell differentiation, dendritic cell activation, dendritic cell polarization, dendritic cell cytokine production, dendritic cell maturation, dendritic cell antigen presentation, dendritic cell expression of one or more serotonin receptors (e.g., expression of one or more serotonin receptors listed in Table 1, e.g., HTR1F, HTR2B, HTR2C, HTR3A, HTR6, and/or HTR7), dendritic cell ADCC, or dendritic cell ADCP. In some embodiments, the cytokine is a pro-inflammatory cytokine (e.g., IL-8). In some embodiments, a serotonin receptor activator described herein decreases inflammation, auto-antibody levels, or the rate or number of relapses or flare-ups.

In some embodiments, a serotonin receptor activator described herein increases improves organ function and/or increases neutrophil lymph node homing. In some embodiments, a serotonin receptor activator described herein decreases one or more of neutrophil migration, neutrophil proliferation, neutrophil recruitment, neutrophil differentiation, neutrophil activation, neutrophil maturation, neutrophil cytokine production, neutrophil antigen presentation, neutrophil lymph node egress, neutrophil expression of one or more serotonin receptors (e.g., expression of one or more serotonin receptors listed in Table 1, e.g., HTR1F, HTR2B, HTR2C, HTR3A, HTR6, and/or HTR7), neutrophil ADCC, or neutrophil ADCP. In some embodiments, the cytokine is a pro-inflammatory cytokine (e.g., IL8). In some embodiments, a serotonin receptor activator described herein decreases inflammation, auto-antibody levels, or the rate or number of relapses or flare-ups. In some embodiments, a serotonin receptor activator described herein decreases one or more of neutrophil migration, neutrophil activation, neutrophil recruitment, or neutrophil lymph node egress by decreasing IL-8 cytokine production by T cells, macrophages, or dendritic cells, or by decreasing activation or polarization of macrophages, T cells, or dendritic cells.

Immune Effects

A variety of in vitro and in vivo assays can be used to determine how a serotonin receptor activator affects an immune cell activity. The effect of a serotonin receptor activator on T cell polarization in a subject can be assessed by evaluation of cell surface markers on T cells obtained from the subject. A blood sample, lymph node biopsy, or tissue sample can be collected from a subject and T cells from the sample evaluated for one or more (e.g., 2, 3, or 4 or more) Th1-specific markers: T-bet, IL-12R, STAT4, or chemokine receptors CCR5, CXCR6, and CXCR3; or Th2-specific markers: CCR3, CXCR4, or IL-4Rα. T cell polarization can also be assessed using the same methods in an in vivo animal model. This assay can also be performed by adding a serotonin receptor activator to T cells in vitro (e.g., T cells obtained from a subject, animal model, repository, or commercial source) and measuring the aforementioned markers to evaluate T cell polarization. These markers can be assessed using flow cytometry, immunohistochemistry, in situ hybridization, and other assays that allow for measurement of cellular markers. Comparing results from before and after administration of a serotonin receptor activator can be used to determine its effect.

The effect of a serotonin receptor activator on T cell activation or inactivation in a subject can be assessed by evaluation of cellular markers on T cells obtained from the subject. A blood sample, lymph node biopsy, or tissue sample can be collected from a subject and T cells from the sample evaluated for one or more (e.g., 2, 3, 4 or more) activation markers: CD25, CD71, CD26, CD27, CD28, CD30, CD154, CD40L, CD134, CD69, CD62L or CD44. T cell activation or inactivation can also be assessed using the same methods in an in vivo animal model. This assay can also be performed by adding a serotonin receptor activator to T cells in vitro (e.g., T cells obtained from a subject, animal model, repository, or commercial source) and measuring the aforementioned markers to evaluate T cell activation or inactivation. Similar approaches can be used to assess the effect of a serotonin receptor activator on activation or inactivation of other immune cells, such as eosinophils (markers: CD35, CD11b, CD66, CD69 and CD81), dendritic cells (makers: IL-8, MHC class II, CD40, CD80, CD83, and CD86), basophils (CD63, CD13, CD4, and CD203c), ILCs (markers: CD69), and neutrophils (CD11 b, CD35, CD66b and CD63). These markers can be assessed using flow cytometry, immunohistochemistry, in situ hybridization, and other assays that allow for measurement of cellular markers. Comparing results from before and after administration of a serotonin receptor activator can be used to determine its effect.

The effect of a serotonin receptor activator on immune cell activation or inactivation can also be assessed through measurement of secreted cytokines and chemokines. An activated immune cell (e.g., T cell, B cell, macrophage, monocyte, dendritic cell, eosinophil, basophil, mast cell, NK cell, ILC, or neutrophil) can produce pro-inflammatory cytokines and chemokines (e.g., IL-1β, IL-5, IL-6, IL-8, IL-10, IL-12, IL-13, IL-18, TNFα, and IFN-γ). Activation or inactivation can be assessed by measuring cytokine levels in a blood sample, lymph node biopsy, or tissue sample from a human subject or animal model, with lower levels of pro-inflammatory cytokines following treatment with a serotonin receptor activator indicating decreased activation, and higher levels indicating decreased activation. Activation or inactivation can also be assessed in vitro by measuring cytokines secreted into the media by cultured cells. Cytokines can be measured using ELISA, western blot analysis, and other approaches for quantifying secreted proteins. Comparing results from before and after administration of a serotonin receptor activator can be used to determine its effect.

The effect of a serotonin receptor activator on T cell proliferation in a subject can be assessed by evaluation of markers of proliferation in T cells obtained from the subject. A blood sample, lymph node biopsy, or tissue sample can be collected from a subject and T cells from the sample evaluated for Ki67 marker expression. T cell proliferation can also be assessed using the same methods in an in vivo animal model. This assay can also be performed by adding a serotonin receptor activator to T cells in vitro (e.g., T cells obtained from a subject, animal model, repository, or commercial source) and measuring Ki67 to evaluate T cell proliferation. Assessing whether a serotonin receptor activator suppresses T cell proliferation can also be performed by in vivo (e.g., in a human subject or animal model) by collecting blood samples before and after serotonin receptor activator administration and comparing T cell numbers, and in vitro by quantifying T cell numbers before and after contacting T cells with a serotonin receptor activator. These approaches can also be used to measure the effect of a serotonin receptor activator on proliferation of any immune cell (e.g., B cells, T cells, macrophages, monocytes, dendritic cells, NK cells, ILCs, mast cells, eosinophils, basophils, and neutrophils). Ki67 can be assessed using flow cytometry, immunohistochemistry, in situ hybridization, and other assays that allow for measurement of nuclear markers. Comparing results from before and after administration of a serotonin receptor activator can be used to determine its effect.

The effect of a serotonin receptor activator on cytotoxic T cell activity in a subject can be assessed by evaluation of T cell granule markers in T cells obtained from the subject. A blood sample, lymph node biopsy, or tissue sample can be collected from a subject and T cells from the sample evaluated for granzyme or perforin expression. Cytotoxic T cell activity can also be assessed using the same methods in an in vivo animal model. This assay can also be performed by adding a serotonin receptor activator to cytotoxic T cells in vitro (e.g., cytotoxic T cells obtained from a subject, animal model, repository, or commercial source) and measuring the aforementioned markers to evaluate suppression of T cell proliferation. These markers can be detected in the media from cytotoxic T cell cultures. Techniques including ELISA, western blot analysis can be used to detect granzyme and perforin in conditioned media, flow cytometry, immunohistochemistry, in situ hybridization, and other assays can detect intracellular granzyme and perforin and their synthesis. Comparing results from before and after administration of a serotonin receptor activator can be used to determine its effect.

The effect of a serotonin receptor activator on circulating monocytes in a subject can be assessed by evaluation of cell surface markers on primary blood mononuclear cells obtained from the subject. A blood sample, lymph node biopsy, or tissue sample can be collected from a subject and monocytes from the sample evaluated for CD14 and/or CD16 expression. Circulating monocytes can also be assessed using the same methods in an in vivo animal model. This assay can be performed by taking a blood sample before treatment with a serotonin receptor activator and comparing it to a blood sample taken after treatment. CD14 and CD16 can be detected using flow cytometry, immunohistochemistry, western blot analysis, or any other technique that can measure cell surface protein levels. Comparing results from before and after administration of a serotonin receptor activator can be used to determine its effect. This assay can be used to detect the number of monocytes in the bloodstream or to determine suppression of monocytes adopting a pro-inflammatory (CD14+/CD16+) phenotype.

The effect of a serotonin receptor activator on peripheral blood hematopoietic stem cells in a subject can be assessed by evaluation of cell surface markers on primary blood mononuclear cells obtained from the subject. A blood sample, lymph node biopsy, or tissue sample can be collected from a subject and stem cells from the sample evaluated for one or more (2, 3 or 4 or more) specific markers: CD34, c-kit, Sca-1, or Thy1.1. Peripheral blood hematopoietic stem cells can also be assessed using the same methods in an in vivo animal model. This assay can be performed by taking a blood sample before treatment with a serotonin receptor activator and comparing it to a blood sample taken after treatment. The aforementioned markers can be detected using flow cytometry, immunohistochemistry, western blot analysis, or any other technique that can measure cell surface protein levels. Comparing results from before and after administration of a serotonin receptor activator can be used to determine its effect. This assay can be used to detect the number of stem cells mobilized into the bloodstream or to determine whether treatment induces differentiation into a particular hematopoietic lineage (e.g., decreases in CD34 and increases in GPA indicates differentiation into red blood cells, decrease in CD34 and increases in CD14 indicates differentiation into monocytes, decreases in CD11 b or CD68 indicates differentiation into macrophages, decreases in CD34 and increases in CD42b indicates differentiation into platelets, decreases in CD34 and increases in CD3 indicates differentiation into T cells, decreases in CD34 and increases in CD19 indicates differentiation into B cells, decreases in CD34 and increases in CD25 or CD69 indicates differentiation into activated T cells, decreases in CD34 and increases in CD1c, CD83, CD141, CD209, or MHC II indicates differentiation into dendritic cells, decreases in CD34 and increases in CD56 indicates differentiation into NK cells, decreases in CD34 and increases in CD15 indicates differentiation into neutrophils, decreases in CD34 and increases in 2D7 antigen, CD123, or CD203c indicates differentiation into basophils, and decreases in CD34 and increases in CD193, EMR1, or Siglec-8 indicates differentiation into eosinophils.

The effect of a serotonin receptor activator on macrophage polarization in a subject can be assessed by evaluation of cellular markers in macrophages cells obtained from the subject. A blood sample, lymph node biopsy, or tissue sample can be collected from a subject and macrophages from the sample evaluated for one of more (2, 3 or 4 or more) specific markers. Markers for M1 polarization include IL-12, TNF, IL-1β, IL-6, IL-23, MARCO, MHC-II, CD86, iNOS, CXCL9, and CXCL10. Markers for M2 polarized macrophages include IL-10, IL1-RA, TGFβ, MR, CD163, DC-SIGN, Dectin-1, HO-1, arginase (Arg-1), CCL17, CCL22 and CCL24. Macrophage polarization can also be assessed using the same methods in an in vivo animal model. This assay can also be performed on cultured macrophages obtained from a subject, an animal model, repository, or commercial source to determine how contacting a macrophage with a serotonin receptor activator affects polarization. The aforementioned markers can be evaluated by comparing measurements obtained before and after administration of a serotonin receptor activator to a subject, animal model, or cultured cell. Surface markers or intracellular proteins (e.g., MHC-11, CD86, iNOS, CD163, Dectin-1, HO-1, Arg-1, etc.) can be measured using flow cytometry, immunohistochemistry, in situ hybridization, or western blot analysis, and secreted proteins (e.g., IL-12, TNF, IL-1β, IL-10, TGFβ, IL1-RA, chemokines CXC8, CXC9, CCL17, CCL22, and CCL24, etc.) can be measured using the same methods or by ELISA or western blot analysis of culture media or blood samples. Comparing results from before and after administration of a serotonin receptor activator can be used to determine its effect.

The effect of a serotonin receptor activator on macrophage phagocytosis in a subject can be assessed by culturing macrophages obtained from the subject with fluorescent beads. A blood sample, lymph node biopsy, or tissue sample can be collected from a subject and macrophages from the sample evaluated for engulfment of fluorescent beads. This assay can also be performed on cultured macrophages obtained from an animal model, repository, or commercial source to determine how contacting a macrophage with a serotonin receptor activator affects phagocytosis. The same phagocytosis assay can be used to evaluate the effect of a serotonin receptor activator on phagocytosis in other immune cells (e.g., neutrophils, monocytes, mast cells, B cells, eosinophils, or dendritic cells). Comparing results from before and after administration of a serotonin receptor activator can be used to determine its effect on phagocytosis.

In some embodiments, phagocytosis is ADCP. ADCP can be assessed using similar methods to those described above by incubating immune cells (e.g., macrophages, neutrophils, monocytes, mast cells, B cells, eosinophils, or dendritic cells) isolated from a blood sample, lymph node biopsy, or tissue sample with fluorescent beads coated with IgG antibodies. In some embodiments, immune cells are incubated with a target cell line that has been pre-coated with antibodies to a surface antigen expressed by the target cell line. ADCP can be evaluated by measuring fluorescence inside the immune cell or quantifying the number of beads or cells engulfed. This assay can also be performed on cultured immune cells obtained from an animal model, repository, or commercial source to determine how contacting an immune cell with a serotonin receptor activator affects ADCP. The ability of an immune cell to perform ADCP can also be evaluated by assessing expression of certain Fc receptors (e.g., FcγRIIa, FcγRIIIa, and FcγRI). Fc receptor expression can be assessed using flow cytometry, immunohistochemistry, in situ hybridization, or other assays that allow for measurement of cell surface markers. Comparing phagocytosis or Fc receptor expression before and after administration of a serotonin receptor activator can be used to determine its effect on ACDP. In some embodiments, the serotonin receptor activator decreases ADCP of certain inflammatory inducing agents. In some embodiments, the serotonin receptor activator decreases macrophage ADCP of auto-antibody coated cells (e.g., in autoimmune diseases such as glomerular nephritis).

The effect of a serotonin receptor activator on macrophage activation in a subject can be assessed by evaluation of cell surface markers on macrophages cells obtained from the subject. A blood sample, lymph node biopsy, or tissue sample can be collected from a subject and macrophages from the sample evaluated for one or more (e.g., 1, 2, 3 or 4 or more) specific markers: F4/80, HLA molecules (e.g., MHC-II), CD80, CD68, CD11b, or CD86. Macrophage activation can also be assessed using the same methods in an in vivo animal model. This assay can also be performed by adding a serotonin receptor activator to macrophages in vitro (e.g., macrophages obtained from a subject, animal model, repository, or commercial source) and measuring the aforementioned markers to evaluate macrophage activation. These markers can be assessed using flow cytometry, immunohistochemistry, in situ hybridization, and other assays that allow for measurement of cell surface markers. As mentioned above, macrophage activation can also be evaluated based on cytokine production (e.g., pro-inflammatory cytokine production) as measured by ELISA and western blot analysis. Comparing results from before and after administration of a serotonin receptor activator can be used to determine its effect.

The effect of a serotonin receptor activator on antigen presentation in a subject can be assessed by evaluation of cell surface markers on antigen presenting cells (e.g., dendritic cells, macrophages, and B cells) obtained from the subject. A blood sample, lymph node biopsy, or tissue sample can be collected from a subject and antigen presenting cells (e.g., dendritic cells, macrophages, and B cells) from the sample evaluated for one or more (e.g., 2, 3 or 4 or more) specific markers: CD11c, CD11b, HLA molecules (e.g., MHC-II), CD40, B7, IL-2, CD80 or CD86. Antigen presentation can also be assessed using the same methods in an in vivo animal model. This assay can also be performed by adding a serotonin receptor activator to antigen presenting cells (e.g., dendritic cells) in vitro (e.g., antigen presenting cells obtained from a subject, animal model, repository, or commercial source) and measuring the aforementioned markers to evaluate antigen presentation. These markers can be assessed using flow cytometry, immunohistochemistry, in situ hybridization, and other assays that allow for measurement of cell surface markers. Comparing results from before and after administration of a serotonin receptor activator can be used to determine its effect.

The effect of a serotonin receptor activator on antigen presenting cell migration in a subject can be assessed by evaluation of cell surface markers on antigen presenting cells (e.g., dendritic cells, B cells, and macrophages) obtained from the subject. A blood sample, lymph node biopsy, or tissue sample can be collected from a subject and antigen presenting cells (e.g., dendritic cells, B cells, and macrophages) from the sample evaluated for CCR7 expression. Antigen presenting cell migration can also be assessed using the same methods in an in vivo animal model. This assay can also be performed by adding a serotonin receptor activator to antigen presenting cells (e.g., dendritic cells, B cells, and macrophages) in vitro (e.g., antigen presenting cells obtained from a subject, animal model, repository, or commercial source) and measuring CCR7 to evaluate antigen presenting cell migration. CCR7 can be assessed using flow cytometry, immunohistochemistry, in situ hybridization, and other assays that allow for measurement of cell surface markers. Comparing results from before and after administration of a serotonin receptor activator can be used to determine its effect.

The effect of a serotonin receptor activator on lymph node immune cell homing and cell egress in a subject can be assessed by evaluation of cell surface markers on T or B cells obtained from the subject. A blood sample, lymph node biopsy, or tissue sample can be collected from a subject and T or B cells from the sample evaluated for one or more specific markers: CCR7 or S1PR1. Lymph node immune cell homing and cell egress can also be assessed using the same methods in an in vivo animal model. This assay can also be performed by adding a serotonin receptor activator to T or B cells in vitro (e.g., T or B cells obtained from a subject, animal model, repository, or commercial source) and measuring the aforementioned markers to evaluate T or B cell lymph node homing. These markers can also be used to assess lymph node homing and cell egress of dendritic cells and macrophages. CCR7 and S1PR1 can be assessed using flow cytometry, immunohistochemistry, in situ hybridization, and other assays that allow for measurement of cell surface markers. If using an animal model, lymph nodes or sites of inflammation can be imaged in vivo (e.g., using a mouse that expresses fluorescently labeled T or B cells) or after biopsy to determine whether T or B cell numbers change as a result of administration of a serotonin receptor activator. Comparing results from before and after administration of a serotonin receptor activator can be used to determine its effect.

In some embodiments, a serotonin receptor activator increases homing or decreases egress of naïve T cells into or out of secondary lymphoid organs prior to antigen challenge (e.g., prior to administration of a vaccine) to generate a better antigen-specific response. In some embodiments, a serotonin receptor activator decreases homing or increases egress of inflammatory immune cells (e.g., neutrophils) into or out of peripheral tissues during injury to prevent conditions such as ischemia-reperfusion disorders. In some embodiments, a serotonin receptor activator decreases homing or increases egress of effector immune subsets into or out of peripheral tissues to avoid inflammation-induced tissue damage in autoimmune diseases.

The effect of a serotonin receptor activator on NK cell activation in a subject can be assessed by evaluation of cell surface markers on NK cells obtained from the subject. A blood sample, lymph node biopsy, or tissue sample can be collected from a subject and NK cells from the sample evaluated for one or more (e.g., 2, 3 or 4 or more) specific markers: CD117, NKp46, CD94, CD56, CD16, KIR, CD69, HLA-DR, CD38, KLRG1, and TIA-1. NK cell activation can also be assessed using the same methods in an in vivo animal model. This assay can also be performed by adding a serotonin receptor activator to NK cells in vitro (e.g., NK cells obtained from a subject, animal model, repository, or commercial source) and measuring the aforementioned markers to evaluate NK cell activation. The effect of a serotonin receptor activator can be determined by comparing results from before and after serotonin receptor activator administration.

In some embodiments, activated NK cells have decreased lytic function or cytotoxicity (e.g., capable of performing ADCC). The effect of a serotonin receptor activator on ADCC can be assessed by incubating immune cells capable of ADCC (e.g., NK cells, monocytes, macrophages, neutrophils, eosinophils, dendritic cells, or T cells) with a target cell line that has been pre-coated with antibodies to a surface antigen expressed by the target cell line. ADCC can be assessed by measuring the number of surviving target cells with a fluorescent viability stain or by measuring the secretion of cytolytic granules (e.g., perforin, granzymes, or other cytolytic proteins released from immune cells). Immune cells can be collected from a blood sample, lymph node biopsy, or tissue sample from a human subject or animal model treated with a serotonin receptor activator. This assay can also be performed by adding a serotonin receptor activator to immune cells in vitro (e.g., immune cells obtained from a subject, animal model, repository, or commercial source). The effect of a serotonin receptor activator on ADCC can be determined by comparing results from before and after serotonin receptor activator administration. In some embodiments, the serotonin receptor activator decreases NK cell ADCC of auto-antibody coated cells (e.g., to treat autoimmune disease).

The effect of a serotonin receptor activator on ILC activation in a subject can be assessed by evaluation of cell surface markers on ILCs obtained from the subject. A blood sample, lymph node biopsy, or tissue sample can be collected from a subject and ILCs from the sample evaluated for one or more (e.g., 2, 3 or 4 or more) specific markers: NKp46, CD69, T-bet, RORα, GATA3, and RORγt. ILC activation can also be assessed using the same methods in an in vivo animal model. This assay can also be performed by adding a serotonin receptor activator to ILCs in vitro (e.g., ILCs obtained from a subject, animal model, repository, or commercial source) and measuring the aforementioned markers to evaluate ILC activation. The effect of a serotonin receptor activator can be determined by comparing results from before and after serotonin receptor activator administration.

In some embodiments, activated ILCs have increased lytic function or are cytotoxic (e.g., capable of performing ADCC). The effect of a serotonin receptor activator on ADCC can be assessed by incubating immune cells capable of ADCC (e.g., ILCs, monocytes, macrophages, neutrophils, eosinophils, dendritic cells, or T cells) with a target cell line that has been pre-coated with antibodies to a surface antigen expressed by the target cell line. ADCC can be assessed by measuring the number of surviving target cells with a fluorescent viability stain or by measuring the secretion of cytolytic granules (e.g., perforin, granzymes, or other cytolytic proteins released from immune cells). Immune cells can be collected from a blood sample, lymph node biopsy, or tissue sample from a human subject or animal model treated with a serotonin receptor activator. This assay can also be performed by adding a serotonin receptor activator to immune cells in vitro (e.g., immune cells obtained from a subject, animal model, repository, or commercial source). The effect of a serotonin receptor activator on ADCC can be determined by comparing results from before and after serotonin receptor activator administration. In some embodiments, the serotonin receptor activator decreases ILC ADCC of auto-antibody coated cells (e.g., to treat autoimmune disease).

The effect of a serotonin receptor activator on mast cell degranulation in a subject can be assessed by evaluation of markers in mast cells obtained from the subject. A blood sample, lymph node biopsy, or tissue sample can be collected from a subject and mast cells from the sample evaluated for one or more (e.g., 1, 2, 3 or 4 or more) specific markers: IgE, histamine, IL-4, TNFα, CD300a, tryptase, or MMP9. Mast cell degranulation can also be assessed using the same methods in an in vivo animal model. This assay can also be performed by adding a serotonin receptor activator to mast cells in vitro (e.g., mast cells obtained from a subject, animal model, repository, or commercial source) and measuring the aforementioned markers to evaluate mast cell degranulation. Some of these markers (e.g., histamine, TNFα, and IL-4) can be detected by measuring levels in the mast cell culture medium after mast cells are contacted with a serotonin receptor activator. The effect of a serotonin receptor activator can be determined by comparing results from before and after serotonin receptor activator administration. This approach can also be used to evaluate the effect of a serotonin receptor activator on degranulation by other cells, such as neutrophils (markers: CD11b, CD13, CD18, CD45, CD15, CD66b IL-1β, IL-8, and IL-6), eosinophils (markers: major basic protein (MBP), eosinophil cationic protein (ECP), eosinophil peroxidase (EPX), eosinophil-derived neurotoxin (EDN)), basophils (markers: histamine, heparin, chondroitin, elastase, lysophospholipase, and LTD-4), NK cells (markers: LAMP-1, perforin, and granzymes), and cytotoxic T cells (markers: LAMP-1, perforin, and granzymes). Markers can be detected using flow cytometry, immunohistochemistry, ELISA, western blot analysis, or in situ hybridization.

The effect of a serotonin receptor activator on neutrophil recruitment in a subject can be assessed by evaluation of cell surface markers on neutrophils obtained from the subject. A blood sample, lymph node biopsy, or tissue sample can be collected from a subject and neutrophils from the sample evaluated for one or more (e.g., 1, 2, 3 or 4 or more) specific markers: CD11b, CD14, CD114, CD177, CD354, or CD66. To determine whether neutrophils are being recruited to a specific site (e.g., a site of inflammation), the same markers can be measured at the site of inflammation o. Neutrophil recruitment can also be assessed using the same methods in an in vivo animal model. This assay can also be performed by adding a serotonin receptor activator to neutrophils in vitro (e.g., neutrophils obtained from a subject, animal model, repository, or commercial source) and measuring the aforementioned markers to evaluate neutrophil recruitment. These markers can be assessed using flow cytometry, immunohistochemistry, in situ hybridization, and other assays that allow for measurement of cell surface markers. The effect of a serotonin receptor activator can be determined by comparing results from before and after serotonin receptor activator administration.

The effect of a serotonin receptor activator on eosinophil recruitment in a subject can be assessed by evaluation of cell surface markers on eosinophil obtained from the subject. A blood sample, lymph node biopsy, or tissue sample can be collected from a subject and eosinophils from the sample evaluated for one or more (e.g., 1, 2, 3 or 4 or more) specific markers: CD15, IL-3R, CD38, CD106, CD294 or CD85G. To determine whether eosinophils are being recruited to a specific site (e.g., a site of inflammation), the same markers can be measured at the site of inflammation. Eosinophil recruitment can also be assessed using the same methods in an in vivo animal model. This assay can also be performed by adding a serotonin receptor activator to eosinophils in vitro (e.g., eosinophils obtained from a subject, animal model, repository, or commercial source) and measuring the aforementioned markers to evaluate eosinophil recruitment. These markers can be assessed using flow cytometry, immunohistochemistry, in situ hybridization, and other assays that allow for measurement of cell surface markers. The effect of a serotonin receptor activator can be determined by comparing results from before and after serotonin receptor activator administration.

The effect of a serotonin receptor activator on NKT cell activation in a subject can be assessed by evaluation of cell surface markers on NKT cells obtained from the subject. A blood sample, lymph node biopsy, or tissue sample can be collected from a subject and NKT cells from the sample evaluated for one or more specific markers: CD272 or CD352. Activated NKT cells produce IFN-γ, IL-4, GM-CSF, IL-2, IL-13, IL-17, IL-21 and TNFα. NKT cell activation can also be assessed using the same methods in an in vivo animal model. This assay can also be performed by adding a serotonin receptor activator to NKT cells in vitro (e.g., NKT cells obtained from a subject, animal model, repository, or commercial source) and measuring the aforementioned markers to evaluate NKT cell activation. Cell surface markers CD272 and CD352 can be assessed using flow cytometry, immunohistochemistry, in situ hybridization, and other assays that allow for measurement of cell surface markers. The secreted proteins can be detected in blood samples or cell culture media using ELISA, western blot analysis, or other methods for detecting proteins in solution. The effect of a serotonin receptor activator can be determined by comparing results from before and after serotonin receptor activator administration.

The effects of a serotonin receptor activator on B cell activation in a subject can be assessed by evaluation of cell surface markers on B cells obtained from the subject. A blood sample, lymph node biopsy, or tissue sample can be collected from a subject and B cells from the sample evaluated for one or more (e.g., 2, 3 or 4 or more) specific markers: CD19, CD20, CD40, CD80, CD86, CD69, IgM, IgD, IgG, IgE, or IgA. B cell activation can also be assessed using the same methods in an in vivo animal model. This assay can also be performed by adding a serotonin receptor activator to B cells in vitro (e.g., B cells obtained from a subject, animal model, repository, or commercial source) and measuring the aforementioned markers to evaluate B cell activation. These markers can be assessed using flow cytometry, immunohistochemistry, in situ hybridization, and other assays that allow for measurement of cell surface markers. The effect of a serotonin receptor activator can be determined by comparing results from before and after serotonin receptor activator administration.

The effect of a serotonin receptor activator on regulatory T cell differentiation in a subject can be assessed by evaluation of markers in regulatory T cells obtained from the subject. A blood sample, lymph node biopsy, or tissue sample can be collected from a subject and regulatory T cells from the sample evaluated for one or more (e.g., 1, 2, 3, 4 or more) specific markers: CD4, CD25, or FoxP3. Regulatory T cell differentiation can also be assessed using the same methods in an in vivo animal model. This assay can also be performed by adding a serotonin receptor activator to regulatory T cells in vitro (e.g., regulatory T cells obtained from a subject, animal model, repository, or commercial source) and measuring the aforementioned markers to evaluate regulatory T cell differentiation. These markers can be assessed using flow cytometry, immunohistochemistry, in situ hybridization, and other assays that allow for measurement of cellular markers. The effect of a serotonin receptor activator can be determined by comparing results from before and after serotonin receptor activator administration.

The effect of a serotonin receptor activator on innervation of a lymph node or secondary lymphoid organ can be assessed by evaluation of neuronal markers in a lymph node or secondary lymphoid organ biopsy sample obtained from a human subject or animal model. A biopsy can be collected from the subject and evaluated for one or more (e.g., 1, 2, 3, 4, or 4 or more) neuronal markers selected from: Neurofilament, synapsin, synaptotagmin, or neuron specific enolase. Lymph node innervation can also be assessed using electrophysiological approaches (e.g., recording neuronal activity in a lymph node or secondary lymphoid organ in a human subject or animal model). The effect of a serotonin receptor activator can be determined by comparing results from before and after serotonin receptor activator administration.

The effect of a serotonin receptor activator on immune cell cytokine production can be assessed by evaluation of cellular markers in an immune cell sample obtained from a human subject or animal model. A blood sample, lymph node biopsy, or tissue sample can be collected for the subject and evaluated for one or more (e.g., 1, 2, 3, 4, or 4 or more) cytokine markers selected from: pro-inflammatory cytokines (e.g., IL-1β, IL-5, IL-6, IL-8, IL-10, IL-12, IL-13, IL-18, TNFα, IFNγ, GMCSF), pro-survival cytokines (e.g., IL-2, IL-4, IL-6, IL-7, and IL-15) and anti-inflammatory cytokines (e.g., IL-4, IL-10, IL-11, IL-13, IFNα, and TGFβ). Some cytokines can function as both pro- and anti-inflammatory cytokines depending on context or indication (e.g., IL-4 is often categorized as an anti-inflammatory cytokine, but plays a pro-inflammatory role in mounting an allergic or anti-parasitic immune response). Cytokines can be also detected in the culture media of immune cells contacted with a serotonin receptor activator. Cytokines can be detected using ELISA, western blot analysis, or other methods for detecting protein levels in solution. The effect of a serotonin receptor activator can be determined by comparing results from before and after serotonin receptor activator administration.

In some embodiments, a serotonin receptor activator decreases or prevents the development of TLOs to decrease local inflammation in autoimmune diseases. TLOs are highly similar to SLOs and exhibit T and B cell compartmentalization, APCs such as DCs and follicular DCs, stromal cells, and a highly organized vascular system of high endothelial venules. In some embodiments, a serotonin receptor activator decreases or prevents the development of HEVs within tertiary lymphoid organs to decrease local inflammation in autoimmune diseases. HEVs can be detected using the monoclonal antibody MECA-79.

In some embodiments, a serotonin receptor activator modulates dendritic cell maturation (e.g., activation). Dendritic cell maturation can be decreased to decrease their migration from peripheral tissues into secondary lymphoid organs to inhibit T cell activation in the draining lymph node (e.g., to improve outcomes in organ transplantation or to reduce the severity of or treat autoimmune diseases).

Table 4 lists additional markers and relevant assays that may be used to assess the level, function and/or activity of immune cells in the methods described herein.

TABLE 4

ASSESSMENT OF IMMUNE CELL PHENOTYPES

| IMMUNE CELL | ASSOCIATED CYTOKINES | MARKER | ASSAYS |
|---|---|---|---|
| Th1 helper | IFN-γ<br>IL-2<br>IL-12<br>IL-18<br>IL-27<br>TNFα<br>TNFβ/LTα | CD4<br>CD94<br>CD119 (IFNγ R1)<br>CD183 (CXCR3)<br>CD186 (CXCR6)<br>CD191 (CCR1)<br>CD195 (CCR5)<br>CD212 (IL-12Rβ1&2)<br>CD254 (RANKL)<br>CD278 (ICOS)<br>IL-18R<br>MRP1<br>NOTCH3<br>TCR<br>TIM3 | ELISPOT<br>In situ hybridization<br>Immunohistochemistry<br>Limiting dilution Analysis<br>Singlec-ell PCR<br>In vivo capture assay<br>ELISA<br>Flow cytometry |
| Th2 helper | IL-4<br>IL-2<br>IL-6<br>IL-33<br>IL-17E (I-L25)<br>IL-31<br>IL-3<br>IL-10<br>IL-13 | CD4<br>CD30<br>CD119 (IFNγ R1)<br>CD184 (CXCR4)<br>CD185 (CXCR5)<br>CD193 (CCR3)<br>CD194 (CCR4)<br>CD197 (CCR7)<br>CD278 (ICOS)<br>CD294 (CRTh2) | ELISPOT<br>In situ hybridization<br>Immunohistochemistry<br>Limiting dilution Analysis<br>Single-cell PCR<br>In vivo capture assay<br>ELISA<br>Flow cytometry |

TABLE 4-continued

ASSESSMENT OF IMMUNE CELL PHENOTYPES

| IMMUNE CELL | ASSOCIATED CYTOKINES | MARKER | ASSAYS |
|---|---|---|---|
| | | CDw198 (CCR8) | |
| | | IL-17RB | |
| | | IL-33Rα (ST2) | |
| | | NOTCH1 | |
| | | NOTCH2 | |
| | | TCR | |
| | | TIM1 | |
| Th17 helper | TGFβ1 | CD4 | ELISPOT |
| | IL-1β | CD27 | In situ hybridization |
| | IL-6 | CD62L | Immunohisto- |
| | IL-21 | CD127 (IL-7R) | chemistry |
| | IL-23 | | Limiting dilution |
| | IL-17A | CD161 | Analysis |
| | IL-17F | CD184 (CXCR4) | Single-cell PCR |
| | IL-22 | | In vivo capture assay |
| | IL-26 | CD194 (CCR4) | ELISA |
| | GM-CSF | CD196 (CCR6) | Flow cytometry |
| | MIP-3α | CD197 (CCR7) | |
| | TNFα | CD212b1 (IL-12Rβ1) | |
| | | CD213a1 (IL-13Rα1) | |
| | | CD278 (ICOS) | |
| | | IL-1R1 | |
| | | IL-21R | |
| | | IL-23R | |
| Treg | TGFβ1 | CD4 | ELISPOT |
| | IL-2 | CD25 | In situ hybridization |
| | IL-10 | CD39 | Immunohisto- |
| | IL-35 | CD73 | chemistry |
| | | CD45RO | Limiting dilution |
| | | CD121a (IL-1R1) | Analysis |
| | | | Single-cell PCR |
| | | CD121b (IL-1R2) | In vivo capture assay |
| | | CD127low | ELISA |
| | | CD134 (OX40) | Flow cytometry |
| | | CD137 (4-1BB) | |
| | | CD152 (CTLA-4) | |
| | | CD357 (GITR/AITR) | |
| | | Foxp3 | |
| | | FR4 (m) | |
| | | GARP (activated) | |
| | | Helios | |
| | | LAP/TGFβ (activated) | |
| | | TIGIT | |
| Dendritic cell | GM-CSF | CD1a | ELISPOT |
| | IFN-γ | CD8 | In situ hybridization |
| | IL-4 | CD11c | Immunohisto- |
| | GMCSF | CD80 | chemistry |
| | IFNα | CD83 | Limiting dilution |
| | IL-1α | CD85 (ILT) family | Analysis |
| | IL-1β | CD86 | Single-cell PCR |
| | IL-6 | CD141 (h) | In vivo capture assay |
| | IL-8 | CD169 | |
| | IL-10 | CD172 | ELISA |
| | IL-12 | CD184 (CXCR4) | Flow cytometry |
| | IL-15 | CD197 (CCR7) | |
| | IL-18 | CD205 | |
| | IL-23 | CD206 | |
| | IL-27 | CD207 | |
| | IP-10 | CD209 | |
| | M-CSF | CD215 (IL-15R) | |
| | RANTES (CCL5) | CD282 (TLR2) | |
| | TGFβ | CD284 (TLR4) | |
| | TNFα | CD286 (TLR6) | |
| | | Clec Family | |
| Macrophages/ Monocytes | FLT3 Ligand | CD11b | ELISPOT |
| | GM-CSF | CD14 (mono) | In situ hybridization |
| | M-CSF | CD16 | Immunohisto- |
| | CXCL9 | CD32 | chemistry |
| | CXCL10 | CD68 | Limiting dilution |
| | CXCL11 | CD85a (ILT5) | Analysis |
| | G-CSF | CD163 | Single-cell PCR |
| | GM-CSF | CD169 | In vivo capture assay |
| | IFNβ | CD195 (CCR5) | |
| | IL-1α | CD204 | ELISA |
| | IL-1β | CD206 | Flow cytometry |
| | IL-6 | CD282 (TLR2) | |
| | IL-8 | CD284 (TLR4) | |
| | IL-10 | CD286 (TLR6) | |
| | IL-12p40 & p70 | CD354 (Trem-1) | |
| | IL-18 | Clec Family | |
| | IL-23 | F4/80 (m) | |
| | IL-27 | HLADR | |
| | M-CSF | | |
| | MIP-2α (CXCL2) | | |
| | RANTES (CCL5) | | |
| | TNFα | | |
| Natural Killer Cell | IL-2 | CD16 | ELISPOT |
| | IL-12 | CD25 | In situ hybridization |
| | IL-15/IL-15R | CD49b | Immunohisto- |
| | IL-18 | CD56 (h) | chemistry |
| | Granzyme B | CD94 | Limiting dilution |
| | IL-17A | CD158 family (KIR) (h) | Analysis |
| | IL-22 | | Single-cell PCR |
| | MIP-1α (CCL3) | CD181 (CXCR1) | In vivo capture assay |
| | MIP-1β (CCL4) | CD183 (CXCR3) | |
| | Perforin | CD184 (CXCR4) | ELISA |
| | RANTES (CCL5) | CD186 (CXCR6) | Flow cytometry |
| | TNFα | CD192 (activated) | |
| | | CD195 (CCR5) | |
| | | CD197 (CCR7) | |
| | | CD212 (IL-12R) | |
| | | CD244 | |
| | | CD314 (NKG2D) | |
| | | CX3CR1 | |
| | | Eomes | |
| | | KLRG1 | |
| | | Ly49 family (m) | |
| | | NK1.1 | |
| | | NKG2A | |
| | | NKp30, NKp42 | |
| | | NKp44 (h) | |
| | | NKp46 | |
| | | T-bet | |
| Innate Lymphoid Cell 1 (ILC1) | IFN-γ | CD335 (MKp46) | ELISPOT |
| | TNF | CD336 (NKp44) | In situ hybridization |
| | | CD94 | Immunohisto- |
| | | CD56 (NCAM) | chemistry |
| | | CD103 | Limiting dilution |
| | | T-bet | Analysis |
| | | | Singel-cell PCR |
| | | | In vivo capture assay |
| | | | ELISA |
| | | | Flow cytometry |
| Innate Lymphoid Cell 2 (ILC2) | Areg | CD127 | ELISPOT |
| | IL-5 | CRTH2 | In situ hybridization |
| | IL-13 | ST2 (IL-33R) | Immunohisto- |
| | | RORα | chemistry |
| | | GATA3 | Limiting dilution |
| | | | Analysis |
| | | | Singel-cell PCR |
| | | | In vivo capture assay |
| | | | ELISA |
| | | | Flow cytometry |

TABLE 4-continued

ASSESSMENT OF IMMUNE CELL PHENOTYPES

| IMMUNE CELL | ASSOCIATED CYTOKINES | MARKER | ASSAYS |
|---|---|---|---|
| Innate Lymphoid Cell 3 (ILC3) | CCL3 LTs IL-22 IL-17 IFN-γ | CD127 CD117 (ckit) CD335 (NKp46) CD336 (NKp44) IL23R RORγt | ELISPOT In situ hybridization Immunohistochemistry Limiting dilution Analysis Single-cell PCR In vivo capture assay ELISA Flow cytometry |
| Activated B cell/ Plasma cells | Antibodies IgM IgG IgD IgE IgA | CD19 CD25 CD30 IgM CD19 IgG CD27 CD38 CD78 CD138 CD319 | Flow cytometry |

TABLE 5

EXAMPLES OF HUMAN CHEMOKINES

| Systematic name | Human gene | Alternate human names | Expression | Human receptor(s) and their expression | Known functions |
|---|---|---|---|---|---|
| C Family | | | | | |
| XCL1 | XCL1 | Lymphotactin, SCM-1 alpha, ATAC | activated CD8+ T cells and other MHCI restricted T cells | XCR1: cross-presenting drendritic cells | migration and activation of lymphocytes, NK cells |
| XCL2 | XCL2 | SCM-1 beta | expressed in activated T cells | XCR1: cross-presenting drendritic cells | migration and activation of lymphocytes, NK cells |
| CX3C Family | | | | | |
| CX3CL1 | CX3CL1 | Fractalkine, Neurotactin, ABCD-3 | brain, heart, lung, kidney, skeletal muscle and testis. Up-regulated in endothelial cells and microglia by inflammation | CX3CR1: lymphocytes, monocytes | migration and adhesion of lymphocytes and monocytes |
| CC Family | | | | | |
| CCL1 | CCL1 | I-309 | activated T cells | CCR8: natural killer cells, monocytes and lymphocytes DARC: erytrocytes, endothelial and epithelial cells | migration of monocytes, NK cells, immature B cells and DCs |
| CCL2 | CCL2 | MCP-1, MCAF, HC11 | monocytes, macrophages and dendritic cells, activated NK cells | CCR2: monocytes CCR4: lymphocytes CCR11: unkown D6: lymphocytes, lymphatic endothelial cells, macrophages DARC: erytrocytes, endothelial and epithelial cells | migration of monocytes and basophils |
| CCL3 | CCL3 | MIP-1 alpha, LD78 alpha, GOS19, Pat464 | T cells, B cells, and monocytes after antigen or mitogen stimulation | CCR1: lymphocytes, monocytes, airway smooth muscle cells CCR4: lymphocytes CCR5: T cells, macrophages, dendritic cells, eosinophils and microglia D6: lymphocytes, lymphatic endothelial cells, macrophages | adhesion of lymphocytes |
| CCL3L1 | CCL3L1 | LD78 beta | Unknown | CCR1: lymphocytes, monocytes, airway smooth muscle cells CCR3: eosinophils, | migration of lymphocytes and monocytes |

TABLE 5-continued

EXAMPLES OF HUMAN CHEMOKINES

| Systematic name | Human gene | Alternate human names | Expression | Human receptor(s) and their expression | Known functions |
|---|---|---|---|---|---|
| | | | | basophils, Th2 cells, CD34+ hematopoetic progenitors, keratinocytes, mast cells<br>CCR5: T cells, macrophages, dendritic cells, eosinophils and microglia<br>D6: lymphocytes, lymphatic endothelial cells, macrophages | |
| CCL3L3 | CCL3L3 | LD78 beta | Unknown | CCR1: lymphocytes, monocytes, airway smooth muscle cells<br>CCR3: eosinophils, basophils, Th2 cells, CD34+ hematopoetic progenitors, keratinocytes, mast cells<br>CCR5: T cells, macrophages, dendritic cells, eosinophils and microglia | migration of lymphocytes and monocytes |
| CCL4 | CCL4 | MIP-1 beta, AT744.1, ACT-2, G-26, HC21, H400, MAD-5, LAG-1 | macrophages, dendritic cells | CCR1: lymphocytes, monocytes, airway smooth muscle cells<br>CCR5: T cells, macrophages, dendritic cells, eosinophils and microglia<br>CCR8: natural killer cells, monocytes and lymphocytes<br>D6: lymphocytes, lymphatic endothelial cells, macrophages | migration and adhesion of lymphocytes, regulatory T cells, NK cells, monocyrtes |
| CCL4L1 | CCL4L1 | AT744.2 | macrophages, dendritic cells | CCR1: lymphocytes, monocytes, airway smooth muscle cells<br>CCR5: T cells, macrophages, dendritic cells, eosinophils and microglia | CCR1 and CCR5 expressing cells |
| CCL4L2 | CCL4L2 | | macrophages, dendritic cells | CCR1: lymphocytes, monocytes, airway smooth muscle cells<br>CCR5: T cells, macrophages, dendritic cells, eosinophils and microglia | CCR1 and CCR5 expressing cells |
| CCL5 | CCL5 | RANTES | T cells, macrophages, platelets, synovial fibroblasts, tubular epithelium, certain types of tumor cells | CCR1: lymphocytes, monocytes, airway smooth muscle cells<br>CCR3: eosinophils, basophils, Th2 cells, CD34+ hematopoetic progenitors, keratinocytes, mast cells<br>CCR4: lymphocytes<br>CCR5: T cells, macrophages, dendritic cells, eosinophils and microglia<br>D6: lymphocytes, lymphatic endothelial | migration of monocytes, memory T helper cells and eosinophils, causes the release of histamine from basophils and activates eosinophils |

TABLE 5-continued

EXAMPLES OF HUMAN CHEMOKINES

| Systematic name | Human gene | Alternate human names | Expression | Human receptor(s) and their expression | Known functions |
|---|---|---|---|---|---|
| CCL7 | CCL7 | MCP-3 | macrophages, certain types of tumor cells | cells, macrophages<br>DARC: erytrocytes, endothelial and epithelial cells<br>CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>D6: lymphocytes, lymphatic endothelial cells, macrophages<br>DARC: erytrocytes, endothelial and epithelial cells | migration of monocytes, activation of macrophages |
| CCL8 | CCL8 | MCP-2, HC14 | fibroblasts, endothelial cells | CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>CCR5: T cells, macrophages, dendritic cells, eosinophils and microglia<br>CCR11: unkown<br>D6: lymphocytes, lymphatic endothelial cells, macrophages<br>DARC: erytrocytes, endothelial and epithelial cells | migration of monocytes, lymphocytes, basophils and eosinophils |
| CCL11 | CCL11 | Eotaxin | lung epithelial cells, pleural mesothelial cells, bronchial airway epithelial cells, smooth muscle cells | CCR3: eosinophils, basophils, Th2 cells, CD34+ hematopoetic progenitors, keratinocytes, mast cells<br>CCR5: T cells, macrophages, dendritic cells, eosinophils and microglia<br>D6: lymphocytes, lymphatic endothelial cells, macrophages<br>DARC: erytrocytes, endothelial and epithelial cells | migration and activation of inflammatory leukocytes, particularly eosinophils |
| CCL12 | | | stromal cells in lung and secondary lymphoid organs | CCR2: monocytes | migration and activation of monocytes |
| CCL13 | CCL13 | MCP-4, CK beta 10, NCC-1 | synovial fibroblasts, chondrocytes | CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>CCR5: T cells, macrophages, | migration of eosinophils, monocytes and T lymphocytes |

TABLE 5-continued

EXAMPLES OF HUMAN CHEMOKINES

| Systematic name | Human gene | Alternate human names | Expression | Human receptor(s) and their expression | Known functions |
|---|---|---|---|---|---|
| | | | | dendritic cells, eosinophils and microglia<br>CCR11: unkown<br>D6: lymphocytes, lymphatic endothelial cells, macrophages<br>DARC: erytrocytes, endothelial and epithelial cells | |
| CCL14 | CCL14 | HCC-1, MCIF, CK beta 1, NCC-2 | spleen, bone marrow, liver, muscle and gut | CCR1: lymphocytes, monocytes, airway smooth muscle cells<br>CCR3: eosinophils, basophils, Th2 cells, CD34+ hematopoetic progenitors, keratinocytes, mast cells<br>CCR5: T cells, macrophages, dendritic cells, eosinophils and microglia<br>D6: lymphocytes, lymphatic endothelial cells, macrophages<br>DARC: erytrocytes, endothelial and epithelial cells | activation of monocytes |
| CCL15 | CCL15 | MIP-1 delta, LKN-1, HCC-2, MIP-5, NCC-3 | airway smooth muscle cells, lung leukocytes, alveolar macrophages, basophils | CCR1: lymphocytes, monocytes, airway smooth muscle cells<br>CCR3: eosinophils, basophils, Th2 cells, CD34+ hematopoetic progenitors, keratinocytes, mast cells | migration of monocytes and eosinophils, proliferation of CD34 myeloid progenitor cells |
| CCL16 | CCL16 | HCC-4, LEC, ILINCK, NCC-4, LMC, CK beta 12 | liver, thymus, and spleen | CCR1: lymphocytes, monocytes, airway smooth muscle cells<br>CCR2: monocytes<br>CCR5: T cells, macrophages, dendritic cells, eosinophils and microglia<br>CCR8: natural killer cells, monocytes and lymphocytes<br>DARC: erytrocytes, endothelial and epithelial cells<br>H4: bone marrow, eosinophils, T-cells, dendritic cells, monocytes, mast cells, neutrophil | migration of lymphocytes and monocytes |
| CCL17 | CCL17 | TARC, ABCD-2 | constitutively expressed in thymus, dendritic cells, keratinocytes | CCR4: lymphocytes<br>CCR8: natural killer cells, monocytes and lymphocytes<br>D6: lymphocytes, lymphatic endothelial cells, macrophages<br>DARC: erytrocytes, endothelial and epithelial cells | Migration and activation of T cells |
| CCL18 | CCL18 | PARC, DC-CK1, AMAC-1, CK beta 7, MIP-4 | dendritic cells, monocytes, and macrophages | CCR8: natural killer cells, monocytes and lymphocytes<br>PITPNM3: breast cancer cells | migration of naive and regulatory lymphocytes, dendritic cells |

TABLE 5-continued

EXAMPLES OF HUMAN CHEMOKINES

| Systematic name | Human gene | Alternate human names | Expression | Human receptor(s) and their expression | Known functions |
|---|---|---|---|---|---|
| CCL19 | CCL19 | MIP-3 beta, ELC, Exodus-3, CK beta 11 | fibroblastic reticular cells, dendritic cells | DARC: erytrocytes, endothelial and epithelial cells CCR7: lymphocytes (mainly naive and memory), mature dendritic cells CCR11: unkown CCRL2: neutrophils, monocytes | migration of naive and memory lymphocytes and mature dendritic cells |
| CCL20 | CCL20 | MIP-3 alpha, LARC, Exodus-1, ST38, CK beta 4 | epidermis (keratinocytes), lymphocytes | CCR6: immature dendritic cells and memory T cells | migration of lymphocytes, DCs and neutrophils |
| CCL21 | CCL21 | 6Ckine, Exodus-2, SLC, TCA-4, CK beta 9 | Stromal cells, lymphatic endothelial cells, fibroblastic reticular cells, dendritic cells | CCR7: lymphocytes (mainly naive and memory), mature dendritic cells CCR11: unkown | migration of lymphocytes homing to secondary lymphoid organs, induces integrin-mediated lymphocyte adhesion |
| CCL22 | CCL22 | MDC | Macrophages | CCR4: lymphocytes D6: lymphocytes, lymphatic endothelial cells, macrophages | migration of NK cells, chronically activated T cells, monocytes and DCs |
| CCL23 | CCL23 | MPIF-1, CK beta 8, CK beta 8-1, MIP-3 | Monocytes | CCR1: lymphocytes, monocytes FPRL-1: monocytes, mast cells | migration of monocytes, resting T cells and neutrophils |
| CCL24 | CCL24 | Eotaxin-2, MPIF-2, CK beta 6 | lung tissue | CCR3: eosinophils, basophils, Th2 cells, CD34+ hematopoetic progenitors, keratinocytes, mast cells | migration of basophils |
| CCL25 | CCL25 | TECK, CK beta 15 | thymic dendritic cells and mucosal epithelial cells | CCR9: T lymphocytes of small intestine | migration of dendritic cells, thymocytes and activated macrophages |
| CCL26 | CCL26 | Eotaxin-3, MIP-4 alpha, IMAC, TSC-1 | heart, lung and ovary and in endothelial cells stimulated with IL4 | CCR3: eosinophils, basophils, Th2 cells, CD34+ hematopoetic progenitors, keratinocytes, mast cells CX3CR1: lymphocytes, monocytes | migration of eosinophils and basophils |
| CCL27 | CCL27 | CTACK, ILC, PESKY, ESKINE | Keratinocytes | CCR10: melanocytes, plasma cells and skin-homing T cells | migration of memory T cells |
| CCL28 | CCL28 | MEC | columnar epithelial cells in the gut, lung, breast and the salivary glands | CCR3: eosinophils, basophils, Th2 T cells, CD34+ hematopoetic progenitors, keratinocytes, mast cells CCR10: melanocytes, plasma cells and skin-homing T cells | migration of lymphocytes and eosinophils |
| CXC Family | | | | | |
| CXCL1 | CXCL1 | GRO alpha, MGSA, GRO1, NAP-3 | mammary, fibroblasts, mammary epithelial cells, endothelial cells, activated, monocytes, | CXCR2 (IL8RB): neutrophils DARC: erytrocytes, endothelial and epithelial cells | migration of neutrophils |

TABLE 5-continued

EXAMPLES OF HUMAN CHEMOKINES

| Systematic name | Human gene | Alternate human names | Expression | Human receptor(s) and their expression | Known functions |
|---|---|---|---|---|---|
| CXCL2 | CXCL2 | GRO beta, MIP-2 alpha, GRO2 | macrophages and neutrophils monocytes, macrophages | CXCR2 (IL8RB): neutrophils DARC: erytrocytes, endothelial and epithelial cells | migration and activation of neutrophils, basophils, hematopoietic stem cells |
| CXCL3 | CXCL3 | GRO gamma, MIP-2 beta, GRO3 | smooth muscle cells, epithelial cells | CXCR2 (IL8RB): neutrophils DARC: erytrocytes, endothelial and epithelial cells | migration and activation of neutrophils |
| CXCL4 | PF4 | PF4 | activated platelets, megakaryocytes, leukocytes, endothelial cells | CXCR3 (CD183b): T cells, NK cells CXCR3-B: T cells, NK cells DARC: erytrocytes, endothelial and epithelial cells | migration of neutrophils and fibroblasts, inhibiting endothelial cell proliferation and chemotaxis |
| CXCL4L1 | PF4V1 | PF4V1 | smooth muscle cells, T cells, and platelets | CXCR3 (CD183b): T cells, NK cells CXCR3-B: T cells, NK cells | inhibiting endothelial cell proliferation and chemotaxis |
| CXCL5 | CXCL5 | ENA-78 | fibroblasts, epithelial cells, eosinophils | CXCR2 (IL8RB): neutrophils DARC: erytrocytes, endothelial and epithelial cells | migration and activation of neutrophils |
| CXCL6 | CXCL6 | GCP-2 | fibroblasts, epithelial cells | CXCR1 (IL8RA): neutrophils CXCR2 (IL8RB): neutrophils DARC: erytrocytes, endothelial and epithelial cells | migration of neutrophils |
| CXCL7 | PPBP | NAP-2, CTAPIII, beta-TG | activated platelets | CXCR1 (IL8RA): neutrophils CXCR2 (IL8RB): neutrophils | migration of neutrophils |
| CXCL8 | IL8 | IL-8, NAP-1, MDNCF, GCP-1 | macrophages, epithelial cells, airway smooth muscle cells, endothelial cells | CXCR1 (IL8RA): neutrophils CXCR2 (IL8RB): neutrophils DARC: erytrocytes, endothelial and epithelial cells | migration of neutrophils, basophils, and T-cells, and angiogenic factor |
| CXCL9 | CXCL9 | MIG, CRG-10 | monocytes, macrophages and endothelial cells | CXCR3 (CD183b): T cells, NK cells CXCR3-B: T cells, NK cells DARC: erytrocytes, endothelial and epithelial cells | migration of Th1 lymphocytes, angiogenic factor |
| CXCL10 | CXCL10 | IP-10 | neutrophils, hepatocytes, endothelial cells and keratinocytes | CXCR3 (CD183b): T cells, NK cells CXCR3-B: T cells, NK cells DARC: erytrocytes, endothelial and epithelial cells | migration of CD4+ T cells |
| CXCL11 | CXCL11 | I-TAC, beta-R1, H174, IP-9 | peripheral blood leukocytes, pancreas and liver astrocytes and at moderate levels in thymus, spleen and lung | CXCR3 (CD183b): T cells, NK cells CXCR7 (ACKR3): tumor cells and tumor-associated blood endothelium DARC: erytrocytes, endothelial and epithelial cells | migration of interleukin-activated T cells but not unstimulated T cells, neutrophils or monocytes. |
| CXCL12 | CXCL12 | SDF-1, PBSF | ubiquitously expressed in many tissues and cell types | CXCR4: brain, heart, lymphocytes, HSCs, blood endothelial cells and umbilical cord | migration of lymphocytes and hepatopoietic |

TABLE 5-continued

EXAMPLES OF HUMAN CHEMOKINES

| Systematic name | Human gene | Alternate human names | Expression | Human receptor(s) and their expression | Known functions |
|---|---|---|---|---|---|
| | | | | endothelial cell CXCR7 (ACKR3): tumor cells and tumor-associated blood endothelium | stem cells, angiogenic factor |
| CXCL13 | CXCL13 | BCA-1, BLC | follicles of the spleen, lymph nodes, and Peyer's patches | CXCR3 (CD183b): T cells, NK cells CXCR5: Burkitt's lymphoma, lymph node follicules, spleen DARC: erytrocytes, endothelial and epithelial cells | migration of B cells |
| CXCL14 | CXCL14 | BRAK, BMAC | Fibroblasts | unknown | migration of monocytes, NK cells, DCs |
| CXCL16 | CXCL16 | SR-PSOX | DCs | CXCR6: T cells | migration of several subsets of T cells and NKT cells |
| CXCL17 | CXCL17 | DMC, VCC-1 | Lung and tumor tissue | unknown | migration of DCs and monocytes |

TABLE 6

EXAMPLES OF HUMAN IMMUNE CELL TRAFFICKING MOLECULES

| Trafficking molecule | Trafficking molecule expressing or presenting cells | Leukocyte ligand | Function in the extravasation cascade |
|---|---|---|---|
| P-selectin | Blood endothelial cell | PSGL-1, L-selectin, CD44 | Tethering/Rolling during extravasation cascade |
| E-selectin | Blood endothelial cell | Glycoprotein, glycolipid, PSGL-1 | Tethering/Rolling during extravasation cascade |
| PNAd | Blood endothelial cell | L-selectin | Tethering/Rolling during extravasation cascade |
| MAdCAM | Blood endothelial cell | L-selectin, integrins | Tethering/Rolling, arrest during extravasation cascade |
| VCAM-1 | Blood endothelial cell | Integrins (e.g. VLA-4) | Tethering/Rolling, arrest during extravasation cascade |
| Chemokines | Blood endothelial cell | GPCRs | Integrin activation, allowing binding of cell adhesion molecules and arrest |
| ICAM-1 | Blood endothelial cell | Integrins (e.g. LFA-1, Mac-1) | Arrest during extravasation cascade |
| ICAM-2 | Blood endothelial cell | Integrins (e.g. LFA-1, Mac-1) | Arrest during extravasation cascade |
| PECAM1 (CD31) | Blood endothelial cell | Integrins (e.g. alpha v beta 3), PECAM1 | Transmigration |
| JAM-A/-B/-C | Blood endothelial cell | Integrins (e.g. LFA-1, Mac-1, VLA-4) | Transmigration |
| ESAM | Blood endothelial cell | unknown | Transmigration |
| CD99 | Blood endothelial cell | CD99 | Transmigration |
| CD99L2 | Blood endothelial cell | possibly CD99L | Transmigration |
| VE-cadherin | Blood endothelial cell | None | Transmigration |
| PVR | Blood endothelial cell | DNAM1 | Transmigration |
| S1P | Lymphatic endothelial cell | S1P receptor 1 (S1P1) | Entry into afferent and efferent lymphatics (in peripheral or SLOs respectively) |

Inflammatory and Autoimmune Conditions

The methods described herein can be used to treat an inflammatory or autoimmune condition or disease in a subject in need thereof by administering an effective amount of a serotonin receptor activator to the subject. The methods described herein can further include a step of identifying (e.g., diagnosing) a subject who has an inflammatory or autoimmune condition, e.g., an inflammatory or autoimmune condition described herein. The method can include administering locally to the subject a serotonin receptor activator described herein in a dose (e.g., effective amount) and for a time sufficient to treat the autoimmune or inflammatory condition or disease.

The methods described herein can be used to inhibit an immune response in a subject in need thereof, e.g., the subject has an autoimmune condition and is in need of inhibiting an immune response against self- or auto-antibodies (e.g., the subject has Graves' disease, systemic lupus erythematosus (SLE or lupus), type 1 diabetes, multiple sclerosis (MS), plaque psoriasis, rheumatoid arthritis (RA) or another autoimmune condition described herein). The methods described herein can also include a step of selecting a subject in need of inhibiting an immune response, e.g., selecting a subject who has or who has been identified to have an inflammatory or autoimmune condition.

Types of Inflammatory and Autoimmune Conditions

In the methods described herein, the condition may be selected from: acute disseminated encephalomyelitis (ADEM); acute necrotizing hemorrhagic leukoencephalitis; Addison's disease; adjuvant-induced arthritis; agammaglobulinemia; alopecia areata; amyloidosis; ankylosing spondylitis; anti-GBM/anti-TBM nephritis; antiphospholipid syndrome (APS); autoimmune angioedema; autoimmune aplastic anemia; autoimmune dysautonomia; autoimmune gastric atrophy; autoimmune hemolytic anemia; autoimmune hepatitis; autoimmune hyperlipidemia; autoimmune immunodeficiency; autoimmune inner ear disease (AIED); autoimmune myocarditis; autoimmune oophoritis; autoimmune pancreatitis; autoimmune retinopathy; autoimmune thrombocytopenic purpura (ATP); autoimmune thyroid disease; autoimmune urticarial; axonal & neuronal neuropathies; Balo disease; Behcet's disease; bullous pemphigoid; cardiomyopathy; Castleman disease; celiac disease; Chagas disease; chronic inflammatory demyelinating polyneuropathy (CIDP); chronic recurrent multifocal ostomyelitis (CRMO); Churg-Strauss syndrome; cicatricial pemphigoid/benign mucosal pemphigoid; Crohn's disease; Cogan syndrome; collagen-induced arthritis; cold agglutinin disease; congenital heart block; coxsackie myocarditis; CREST disease; essential mixed cryoglobulinemia; demyelinating neuropathies; dermatitis herpetiformis; dermatomyositis; Devic's disease (neuromyelitis optica); discoid lupus; Dressler's syndrome; endometriosis; eosinophilic esophagitis; eosinophilic fasciitis; erythema nodosum experimental allergic encephalomyelitis; experimental autoimmune encephalomyelitis; Evans syndrome; fibromyalgia; fibrosing alveolitis; giant cell arteritis (temporal arteritis); giant cell myocarditis; glomerulonephritis; Goodpasture's syndrome; granulomatosis with polyangiitis (GPA) (formerly called Wegener's granulomatosis); Graves' disease; Guillain-Barre syndrome; Hashimoto's encephalitis; Hashimoto's thyroiditis; hemolytic anemia; Henoch-Schonlein purpura; herpes gestationis; hypogammaglobulinemia; idiopathic thrombocytopenic purpura (ITP); IgA nephropathy; IgG4-related sclerosing disease; immunoregulatory lipoproteins; inclusion body myositis; interstitial cystitis; inflammatory bowel disease; juvenile arthritis; juvenile oligoarthritis; juvenile diabetes (type 1 diabetes); juvenile myositis; Kawasaki syndrome; Lambert-Eaton syndrome; leukocytoclastic vasculitis; lichen planus; lichen sclerosus; ligneous conjunctivitis; linear IgA disease (LAD); lupus (SLE); Lyme disease, chronic; Meniere's disease; microscopic polyangiitis; mixed connective tissue disease (MCTD); Mooren's ulcer; Mucha-Habermann disease; multiple sclerosis; myasthenia gravis; myositis; arcolepsy; neuromyelitis optica (Devic's); neutropenia; non-obese diabetes; ocular cicatricial pemphigoid; optic neuritis; palindromic rheumatism; PANDAS (pediatric autoimmune neuropsychiatric disorders associated with streptococcus); paraneoplastic cerebellar degeneration; paroxysmal nocturnal hemoglobinuria (PNH); Parry Romberg syndrome; Parsonnage-Turner syndrome; pars planitis (peripheral uveitis); pemphigus; pemphigus vulgaris; peripheral neuropathy; perivenous encephalomyelitis; pernicious anemia; POEMS syndrome; polyarteritis nodosa; type I, II, & III autoimmune polyglandular syndromes; polymyalgia rheumatic; polymyositis; postmyocardial infarction syndrome; postpericardiotomy syndrome; progesterone dermatitis; primary biliary cirrhosis; primary sclerosing cholangitis; psoriasis; plaque psoriasis; psoriatic arthritis; idiopathic pulmonary fibrosis; pyoderma gangrenosum; pure red cell aplasia; Raynauds phenomenon; reactive Arthritis; reflex sympathetic dystrophy; Reiter's syndrome; relapsing polychondritis; restless legs syndrome; retroperitoneal fibrosis; rheumatic fever; rheumatoid arthritis; sarcoidosis; Schmidt syndrome; scleritis; scleroderma; sclerosing cholangitis; sclerosing sialadenitis; Sjogren's syndrome; sperm & testicular autoimmunity; stiff person syndrome; subacute bacterial endocarditis (SBE); Susac's syndrome; sympathetic ophthalmia; systemic lupus erythematosus (SLE); systemic sclerosis; Takayasu's arteritis; temporal arteritis/giant cell arteritis; thrombocytopenic purpura (TTP); Tolosa-Hunt syndrome; transverse myelitis; type 1 diabetes; ulcerative colitis; undifferentiated connective tissue disease (UCTD); uveitis; vasculitis; vesiculobullous dermatosis; vitiligo; Wegener's granulomatosis (now termed granulomatosis with polyangiitis (GPA).

In some embodiments, the inflammatory or autoimmune disease or condition is an IL-8-associated autoimmune disease or condition in which anti-IL-8 therapies have been tested (e.g., anti-IL-8 antibodies) or are in clinical development, in which agents used to treat the disease or condition have been found to reduce IL-8, or in which IL-8 has been found to be elevated. IL-8-associated autoimmune diseases or conditions in which anti-IL-8 therapies have been tested or are in clinical development, or in which agents used to treat the disease or condition have been found to reduce IL-8 include collagen-induced arthritis, coxsackie myocarditis, glomerulonephritis, pemphigus vulgaris, psoriasis, rheumatoid arthritis, uveitis, scleroderma, and dermatitis. Inflammatory or autoimmune diseases or conditions that are associated with elevated levels of IL-8 include alopecia areata, amyloidosis, ankylosing spondylitis, antiphospholipid syndrome, autoimmune aplastic anemia, autoimmune hepatitis, autoimmune immunodeficiency, autoimmune pancreatitis, autoimmune thyroid disease, autoimmune urticarial, axonal & neuronal neuropathies, Behcet's disease, bullous pemphigoid, cardiomyopathy, celiac disease, chronic inflammatory demyelinating polyneuropathy, Crohn's disease, chronic recurrent multifocal osteomyelitis, Churg-Strauss syndrome, cicatricial pemphigoid/benign mucosal pemphigoid, CREST disease, demyelinating neuropathies, dermatitis herpetiformis, dermatomyositis, Devic's disease, endometriosis, eosinophilic esophagitis, fibromyalgia, fibrosing alveolitis, giant cell arteritis (temporal arteritis), granulomatosis with polyangiitis, Graves' disease, Guillain-Barre syndrome, hemolytic anemia, Henoch-Schonlein purpura, hypogammaglobulinemia, IgA nephropathy, inclusion body myositis, inflammatory bowel disease, juvenile arthritis, Juvenile diabetes (Type 1 diabetes), juvenile myositis, Kawasaki syndrome, leukocytoclastic vasculitis, lichen planus, lupus (SLE), Lyme disease, chronic, Mooren's ulcer, multiple sclerosis, myasthenia gravis, myositis, narcolepsy, neutropenia, ocular cicatricial pemphigoid, optic neuritis, PANDAS, pars planitis, pemphigus, peripheral neuropathy, perivenous encephalomyelitis, POEMS syndrome, polyarteritis nodosa, polymyalgia rheumatic, polymyositis, primary biliary cirrhosis, primary sclerosing cholangitis, psoriatic arthritis, idiopathic pulmonary fibrosis, pyoderma gangrenosum, relapsing polychondritis, rheumatic fever, sarcoidosis, Sjogren's syndrome, sperm & testicular autoimmunity, subacute bacterial endocarditis, systemic sclerosis, Takayasu's arteritis, transverse myelitis, ulcerative colitis, vasculitis, vesiculobullous dermatosis, and vitiligo.

Serotonin receptor activators described herein can be administered in combination with a second therapeutic agent for treatment of an inflammatory or autoimmune disease or condition. Additional therapeutic agents include, 6-mercaptopurine, 6-thioguanine, abatacept, adalimumab, alemtuzumab (Lemtrada), aminosalicylates (5-aminoalicylic acid, sulfasalazine, mesalamine, balsalazide, olsalazine), antibiotics, anti-histamines, Anti-TNFα (infliximab, adalimumab, certolizumab pegol, natalizumab) Ustekinumab), azathioprine, belimumab, beta interferon, calcineurin inhibitors, certolizumab, corticosteroids (prednisone, methylprednisolone), cromolyn, cyclosporin A, cyclosporine, dimethyl fumarate (tecfidera), etanercept, fingolimod (Gilenya), fumaric acid esters, glatiramer acetate (Copaxone), golimumab, hydroxyurea, IFNγ, IL-11, infliximab, leflunomide, leukotriene receptor antagonist, long-acting beta2 agonist, methotrexate, mitoxantrone, mycophenolate mofetil, natalizumab (tysabri), NSAIDs, ocrelizumab, pimecrolimus, probiotics (VSL #3), retinoids, rituximab, salicylic acid, short-acting beta2 agonist, sulfasalazine, tacrolimus, teriflunomide (Aubagio), theophylline, tocilizumab, ustekinumab (anti-IL12/IL23), and vedolizumab (Anti alpha3 beta7 integrin).

Neuromodulatory Combination Therapies

Neurotransmission Modulators

In some embodiments, the serotonin receptor activator is administered in combination with a neurotransmission modulator (e.g., an agent that increases or decreases neurotransmission). A neurotransmission modulator can be used to modulate neural activity in a lymph node or site of inflammation that is innervated by nerves or to modulate immune cells that express neurotransmitter receptors. For example, in some embodiments, the neurotransmission modulator is a neurotransmitter or neurotransmitter receptor listed in Table 7 or 8, or an agonist or antagonist listed in Tables 9A-9J for a corresponding neurotransmitter pathway member. In some embodiments, the neurotransmission modulator is a neurotransmission modulator listed in Table 10. Neurotransmission modulators that increase neurotransmission include neurotransmitters and neurotransmitter receptors listed in Tables 7 and 8 and analogs thereof, and neurotransmitter agonists (e.g., small molecules that agonize a neurotransmitter receptor listed in Table 7). Exemplary agonists are listed in Tables 9A-9J. In some embodiments, neurotransmission is increased via administration, local delivery, or stabilization of neurotransmitters (e.g., ligands listed in Tables 7 or 8). Neurotransmission modulators that increase neurotransmission also include agents that increase neurotransmitter synthesis or release (e.g., agents that increase the activity of a biosynthetic protein encoded by a gene in Table 7 via stabilization, overexpression, or upregulation, or agents that increase the activity of a synaptic or vesicular protein via stabilization, overexpression, or upregulation), prevent neurotransmitter reuptake or degradation (e.g., agents that block or antagonize transporters that remove neurotransmitter from the synaptic cleft), increase neurotransmitter receptor activity (e.g., agents that increase the activity of a signaling protein encoded by a gene in Table 7 via stabilization, overexpression, agonism, or upregulation, or agents that upregulate, agonize, or stabilize a neurotransmitter receptor listed in Table 7), increase neurotransmitter receptor synthesis or membrane insertion, decrease neurotransmitter degradation, and regulate neurotransmitter receptor conformation (e.g., agents that bind to a receptor and keep it in an "open" or "primed" conformation). In some embodiments, the neurotransmitter receptor is a channel, the activity of which can be increased by agonizing, opening, stabilizing, or overexpressing the channel.

Neurotransmission modulators can increase neurotransmission by 10%, 20%, 30%, 40%, 50%, 60%, 70%, 80%, 90%, 95%, 98% or more. Exemplary neurotransmission modulators are listed in Table 10. Neurotransmission modulators that decrease neurotransmission include neurotransmitter antagonists (e.g., small molecules that antagonize a neurotransmitter receptor listed in Table 7). Exemplary antagonists are listed in Tables 9A-9J. Neurotransmission modulators that decrease neurotransmission also include agents that decrease neurotransmitter synthesis or release (e.g., agents that decrease the activity of a biosynthetic protein encoded by a gene in Table 7 via inhibition or downregulation, or agents that decrease the activity of a synaptic or vesicular protein via blocking, disrupting, downregulating, or antagonizing the protein), increase neurotransmitter reuptake or degradation (e.g., agents that agonize, open, or stabilize transporters that remove neurotransmitter from the synaptic cleft), decrease neurotransmitter receptor activity (e.g., agents that decrease the activity of a signaling protein encoded by a gene in Table 7 or via blocking or antagonizing the protein, or agents that block, antagonize, or downregulate a neurotransmitter receptor listed in Table 7), decrease neurotransmitter receptor synthesis or membrane insertion, increase neurotransmitter degradation, regulate neurotransmitter receptor conformation (e.g., agents that bind to a receptor and keep it in a "closed" or "inactive" conformation), and disrupt the pre- or postsynaptic machinery (e.g., agents that block or disrupt a structural protein, or agents that block, disrupt, downregulate, or antagonize a synaptic or vesicular protein). In some embodiments, the neurotransmitter receptor is a channel (e.g., a ligand or voltage gated ion channel), the activity of which can be decreased by blockade, antagonism, or inverse agonism of the channel. Neurotransmission modulators that decrease neurotransmission further include agents that sequester, block, antagonize, or degrade a neurotransmitter listed in Tables 7 or 8. Neurotransmission modulators that decrease or block neurotransmission include antibodies that bind to or block the function of neurotransmitters, neurotransmitter receptor antagonists, and toxins that disrupt synaptic release. Neurotransmission modulators can decrease neurotransmission by 10%, 20%, 30%, 40%, 50%, 60%, 70%, 80%, 90%, 95%, 98% or more. Neurotransmission modulator can be administered in any of the modalities described herein (e.g., antibody, small molecule, nucleic acid, polypeptide, or viral vector).

TABLE 7

NEUROTRANSMITTER GENES & PATHWAYS

| Gene | Pathway | Type | Accession Number | Entrez Gene ID |
|---|---|---|---|---|
| ABAT | Neurotransmitter | Biosynthesis | P80404 | 18 |
| ACHE | Neurotransmitter | Biosynthesis | P22303 | 43 |
| ADORA2A | Neurotransmitter | Receptor | P29274 | 135 |
| ADORA2B | Neurotransmitter | Receptor | P29275 | 136 |
| Adra1a | Adrenergic/ Neurotransmitter | Receptor | P35348 | 148 |
| Adra1b | Adrenergic/ Neurotransmitter | Receptor | P35368 | 147 |
| Adra1d | Adrenergic/ Neurotransmitter | Receptor | P25100 | 146 |

TABLE 7-continued

NEUROTRANSMITTER GENES & PATHWAYS

| Gene | Pathway | Type | Accession Number | Entrez Gene ID |
|---|---|---|---|---|
| Adra2a | Adrenergic/Neurotransmitter | Receptor | P08913 | 150 |
| Adra2b | Adrenergic/Neurotransmitter | Receptor | P18089 | 151 |
| Adra2c | Adrenergic/Neurotransmitter | Receptor | P18825 | 152 |
| Adrb1 | Adrenergic/Neurotransmitter | Receptor | P08588 | 153 |
| Adrb2 | Adrenergic/Neurotransmitter | Receptor | P07550 | 154 |
| Adrb3 | Adrenergic/Neurotransmitter | Receptor | P13945 | 155 |
| Adrbk1 | Adrenergic | Kinase | P25098 | 156 |
| Adrbk2 | Adrenergic | Kinase | P35626 | 157 |
| BACE1 | Neurotransmitter | Biosynthesis | P56817 | 23621 |
| BCHE | Neurotransmitter | Biosynthesis | P06276 | 590 |
| BRS3 | Neuromodulator | Receptor | P32247 | P32247 |
| C6orf89 | Neuromodulator | Receptor | Q6UWU4 | 221477 |
| CHAT | Neurotransmitter | Biosynthesis | P28329 | 1103 |
| CHRFAM7A | Neurotransmitter | Receptor | Q494W8 | 89832 |
| Chrm1 | Cholinergic/Neurotransmitter | Receptor | P11229 | 1128 |
| Chrm2 | Cholinergic/Neurotransmitter | Receptor | P08172 | 1129 |
| Chrm3 | Cholinergic/Neurotransmitter | Receptor | P20309 | 1131 |
| Chrm4 | Cholinergic/Neurotransmitter | Receptor | P08173 | 1132 |
| Chrm5 | Cholinergic/Neurotransmitter | Receptor | P08912 | 1133 |
| Chrna1 | Cholinergic/Neurotransmitter | Receptor | P02708 | 1134 |
| Chrna10 | Cholinergic/Neurotransmitter | Receptor | Q9GZZ6 | 57053 |
| Chrna2 | Cholinergic/Neurotransmitter | Receptor | Q15822 | 1135 |
| Chrna3 | Cholinergic/Neurotransmitter | Receptor | P32297 | 1136 |
| Chrna4 | Cholinergic/Neurotransmitter | Receptor | P43681 | 1137 |
| Chrna5 | Cholinergic/Neurotransmitter | Receptor | P30532 | 1138 |
| Chrna6 | Cholinergic/Neurotransmitter | Receptor | Q15825 | 8973 |
| Chrna7 | Cholinergic/Neurotransmitter | Receptor | P36544 | 1139 |
| Chrna9 | Cholinergic/Neurotransmitter | Receptor | Q9UGM1 | 55584 |
| Chrnb1 | Cholinergic/Neurotransmitter | Receptor | P11230 | 1140 |
| Chrnb2 | Cholinergic/Neurotransmitter | Receptor | P17787 | 1141 |
| Chrnb3 | Cholinergic/Neurotransmitter | Receptor | Q05901 | 1142 |
| Chrnb4 | Cholinergic/Neurotransmitter | Receptor | P30926 | 1143 |
| Chrnd | Cholinergic/Neurotransmitter | Receptor | Q07001 | 1144 |
| Chrne | Cholinergic/Neurotransmitter | Receptor | Q04844 | 1145 |
| Chrng | Cholinergic/Neurotransmitter | Receptor | P07510 | 1146 |
| CNR1 | Cannabinoid/Neurotransmitter | Receptor | P21554 | 1268 |
| CNR2 | Cannabinoid/Neurotransmitter | Receptor | P34972 | 1269 |
| CNRIP1 | Neurotransmitter | Receptor | Q96F85 | 25927 |
| COMT | Neurotransmitter | Biosynthesis | P21964 | 1312 |
| CPA4 | Neurotransmitter | Biosynthesis | Q9UI42 | 51200 |
| CPE | Neuropeptide/Neurotransmitter | Biosynthesis | P16870 | 1363 |
| CREM | Neurotransmitter | Signaling | Q03060 | 1390 |
| DAGLA | Neurotransmitter (Cannabinoid) | Biosynthesis | Q9Y4D2 | 747 |
| DAGLB | Neurotransmitter (Cannabinoid) | Biosynthesis | Q8NCG7 | 221955 |
| DBH | Neurotransmitter | Biosynthesis | P09172 | 1621 |
| DDC | Neurotransmitter | Biosynthesis | P20711 | 1644 |
| DGKI | Neurotransmitter | Biosynthesis | O75912 | 9162 |
| DOPO | Dopaminergic | Receptor | P09172 | 1621 |
| DPP4 | Neurotransmitter | Biosynthesis | P27487 | 1803 |
| Drd1 | Dopaminergic/Neurotransmitter | Receptor | P21728 | 1812 |
| Drd2 | Dopaminergic/Neurotransmitter | Receptor | P14416 | 1813 |
| Drd3 | Dopaminergic/Neurotransmitter | Receptor | P35462 | 1814 |
| Drd4 | Dopaminergic/Neurotransmitter | Receptor | P21917 | 1815 |
| Drd5 | Dopaminergic/Neurotransmitter | Receptor | P21918 | 1816 |
| ECEL1 | Neurotransmitter | Biosynthesis | O95672 | 9427 |
| FAAH | Neurotransmitter | Biosynthesis | O00519 | 2166 |
| FNTA | Neurotransmitter | Signaling | P49354 | 2339 |
| GABARAP | Neurotransmitter | Receptor | O95166 | 11337 |
| GABARAPL1 | Amine Neuromodulator | Receptor | Q9H0R8 | 23710 |
| GABARAPL2 | Amine Neuromodulator | Receptor | P60520 | 11345 |
| GABBR1 | Neurotransmitter | Receptor | Q9UBS5 | 2550 |
| GABBR2 | Amine Neuromodulator | Receptor | O75899 | 9568 |
| GABRA1 | Neurotransmitter | Receptor | P14867 | 2554 |
| GABRA2 | Neurotransmitter | Receptor | P47869 | 2555 |
| GABRA3 | Neurotransmitter | Receptor | P34903 | 2556 |
| GABRA4 | Neurotransmitter | Receptor | P48169 | 2557 |
| GABRA5 | Neurotransmitter | Receptor | P31644 | 2558 |
| GABRA6 | Neurotransmitter | Receptor | Q16445 | 2559 |
| GABRB1 | Neurotransmitter | Receptor | P18505 | 2560 |
| GABRB2 | Neurotransmitter | Receptor | P47870 | 2561 |
| GABRB3 | Neurotransmitter | Receptor | P28472 | 2562 |
| GABRD | Neurotransmitter | Receptor | O14764 | 2563 |
| GABRE | Neurotransmitter | Receptor | P78334 | 2564 |
| GABRG1 | Neurotransmitter | Receptor | Q8N1C3 | 2565 |
| GABRG2 | Neurotransmitter | Receptor | P18507 | 2566 |
| GABRG3 | Neurotransmitter | Receptor | Q99928 | 2567 |
| GABRP | Neurotransmitter | Receptor | O00591 | 2568 |
| GABRQ | Neurotransmitter | Receptor | Q9UN88 | 55879 |
| GABRR1 | Neurotransmitter | Receptor | P24046 | 2569 |
| GABRR2 | Neurotransmitter | Receptor | P28476 | 2570 |
| GABRR3 | Neurotransmitter | Receptor | A8MPY1 | 200959 |
| GAD1 | Neurotransmitter | Biosynthesis | Q99259 | 2571 |
| GAD2 | Neurotransmitter | Biosynthesis | Q05329 | 2572 |
| GCHFR | Neurotransmitter | Biosynthesis | P30047 | 2644 |
| GLRA1 | Neurotransmitter | Receptor | P23415 | 2741 |
| GLRA2 | Neurotransmitter | Receptor | P23416 | 2742 |
| GLRA3 | Neurotransmitter | Receptor | O75311 | 8001 |
| GLRA4 | Neurotransmitter | Receptor | Q5JXX5 | 441509 |
| GLRB | Neurotransmitter | Receptor | P48167 | 2743 |
| GLS | Neurotransmitter | Biosynthesis | O94925 | 2744 |
| GLS2 | Neurotransmitter | Biosynthesis | Q9UI32 | 27165 |
| GluA1 (GluR1) | Amine Neuromodulator | Receptor | P42261 | 2890 |
| GluK1 (GluR5) | Amine Neuromodulator | Receptor | P39086 | 2897 |
| GLUL | Neurotransmitter | Biosynthesis | P15104 | 2752 |
| GluN1(NR1) | Amine Neuromodulator | Receptor | Q05586 | 2902 |
| GNMT | Neurotransmitter | Biosynthesis | Q14749 | 27232 |
| GPER1 | Neurotransmitter | Receptor | Q99527 | 2852 |
| GPR1 | Neurotransmitter | Receptor | P46091 | 2825 |
| GPR139 | Neurotransmitter | Receptor | Q6DWJ6 | 124274 |
| GPR143 | Neurotransmitter | Receptor | P51810 | 4935 |
| GPR149 | Neurotransmitter | Receptor | Q86SP6 | 344758 |
| GPR18 | Neurotransmitter | Receptor | Q14330 | 2841 |
| GPR21 | Neurotransmitter | Receptor | Q99679 | 2844 |
| GPR26 | Neurotransmitter | Receptor | Q8NDV2 | 2849 |
| GPR3 | Neurotransmitter | Receptor | P46089 | 2827 |
| GPR35 | Neurotransmitter | Receptor | Q9H097 | 2859 |

TABLE 7-continued

NEUROTRANSMITTER GENES & PATHWAYS

| Gene | Pathway | Type | Accession Number | Entrez Gene ID |
|---|---|---|---|---|
| GPR52 | Neurotransmitter | Receptor | Q9Y2T5 | 9293 |
| GPR55 | Neurotransmitter | Receptor | Q9Y2T6 | 9290 |
| GPR78 | Neurotransmitter | Receptor | Q96P69 | 27201 |
| GPR83 | Neurotransmitter | Receptor | Q9NYM4 | 10888 |
| GPR84 | Neurotransmitter | Receptor | Q9NQS5 | 53831 |
| GPRASP1 | Neurotransmitter | Receptor | Q5JY77 | 9737 |
| GPR50 | Amine Neuromodulator | Receptor | Q13585 | 9248 |
| GRIA1 | Neurotransmitter | Receptor | P42261 | 2890 |
| GRIA2 | Neurotransmitter | Receptor | P42262 | 2891 |
| GRIA3 | Neurotransmitter | Receptor | P42263 | 2892 |
| GRIA4 | Neurotransmitter | Receptor | P48058 | 2893 |
| GRID1 | Neurotransmitter | Receptor | Q9ULKO | 2894 |
| GRI D2 | Neurotransmitter | Receptor | Q43424 | 2895 |
| GRIK1 | Neurotransmitter | Receptor | P39086 | 2897 |
| GRIK2 | Neurotransmitter | Receptor | Q13002 | 2898 |
| GRIK3 | Neurotransmitter | Receptor | Q13003 | 2899 |
| GRIK4 | Neurotransmitter | Receptor | Q16099 | 2900 |
| GRIK5 | Neurotransmitter | Receptor | Q16478 | 2901 |
| GRIN1 | Neurotransmitter | Receptor | Q05586 | 2902 |
| GRIN2A | Neurotransmitter | Receptor | Q12879 | 2903 |
| GRIN2B | Neurotransmitter | Receptor | Q13224 | 2904 |
| GRIN2C | Neurotransmitter | Receptor | Q14957 | 2905 |
| GRIN2D | Neurotransmitter | Receptor | O15399 | 2906 |
| GRIN3A | Neurotransmitter | Receptor | Q8TCU5 | 116443 |
| GRIN3B | Neurotransmitter | Receptor | O60391 | 116444 |
| GRK2 | Neurotransmitter | Receptor | P25098 | 156 |
| GRK3 | Neurotransmitter | Receptor | P35626 | 157 |
| GRM1 | Neurotransmitter | Receptor | Q13255 | 2911 |
| GRM2 | Neurotransmitter | Receptor | Q14416 | 2912 |
| GRM3 | Neurotransmitter | Receptor | Q14832 | 2913 |
| GRM4 | Neurotransmitter | Receptor | Q14833 | 2914 |
| GRM5 | Neurotransmitter | Receptor | P41594 | 2915 |
| GRM6 | Neurotransmitter | Receptor | Q15303 | 2916 |
| GRM7 | Neurotransmitter | Receptor | Q14831 | 2917 |
| GRM8 | Neurotransmitter | Receptor | O00222 | 2918 |
| HNMT | Neurotransmitter | Biosynthesis | P50135 | 3176 |
| HOMER1 | Neurotransmitter | Receptor | Q86YM7 | 9456 |
| HRH1 | Neurotransmitter | Receptor | P35367 | 3269 |
| HRH2 | Neurotransmitter | Receptor | P25021 | 3274 |
| HRH3 | Neurotransmitter | Receptor | Q9Y5N1 | 11255 |
| HRH4 | Neurotransmitter | Receptor | Q9H3N8 | 59340 |
| ITPR1 | Neurotransmitter | Signaling | Q14643 | 3708 |
| ITPR2 | Neurotransmitter | Signaling | Q14571 | 3709 |
| ITPR3 | Neurotransmitter | Signaling | Q14573 | 3710 |
| LYNX1 | Neurotransmitter | Receptor | Q9BZG9 | 66004 |
| MAOA | Neurotransmitter | Biosynthesis | P21397 | 4128 |
| MAOB | Neurotransmitter | Biosynthesis | P27338 | 4129 |
| NAM PT | Neurotransmitter | Biosynthesis | P43490 | 10135 |
| NISCH | Neurotransmitter | Receptor | Q9Y2I1 | 11188 |
| NOS1 | Neurotransmitter | Biosynthesis | P29475 | 4842 |
| NPTN | Neurotransmitter | Receptor | Q9Y639 | 27020 |
| P2RX1 | Neurotransmitter | Receptor | P51575 | 5023 |
| P2RX2 | Neurotransmitter | Receptor | Q9UBL9 | 22953 |
| P2RX3 | Neurotransmitter | Receptor | P56373 | 5024 |
| P2RX4 | Neurotransmitter | Receptor | Q99571 | 5025 |
| P2RX5 | Neurotransmitter | Receptor | Q93086 | 5026 |
| P2RX6 | Neurotransmitter | Receptor | O15547 | 9127 |
| P2RX7 | Neurotransmitter | Receptor | Q99572 | 5027 |
| P2RY11 | Neurotransmitter | Receptor | Q96G91 | 5032 |
| PAH | Neurotransmitter | Biosynthesis | P00439 | 5053 |
| PC | Neurotransmitter | Biosynthesis | P11498 | 5091 |
| PDE1B | Neurotransmitter | Signaling | Q01064 | 5153 |
| PDE4A | Neurotransmitter | Signaling | P27815 | 5141 |
| PDE4D | Neurotransmitter | Signaling | Q08499 | 5144 |
| PHOX2A | Neurotransmitter | Biosynthesis | O14813 | 401 |
| PHOX2B | Neurotransmitter | Biosynthesis | Q099453 | 8929 |
| PIK3CA | Neurotransmitter | Signaling | P42336 | 5290 |
| PIK3CB | Neurotransmitter | Signaling | P42338 | 5291 |
| PIK3CG | Neurotransmitter | Signaling | P48736 | 5294 |
| PLCB1 | Neurotransmitter | Signaling | Q9N066 | 23236 |
| PLCB2 | Neurotransmitter | Signaling | Q00722 | 5330 |
| PLCB3 | Neurotransmitter | Signaling | Q01970 | 5331 |
| PLCB4 | Neurotransmitter | Signaling | Q15147 | 5332 |
| PLCD1 | Neurotransmitter | Signaling | P51178 | 5333 |
| PLCE1 | Neurotransmitter | Signaling | Q9P212 | 51196 |
| PLCG1 | Neurotransmitter | Signaling | P19174 | 5335 |
| PLCL1 | Neurotransmitter | Signaling | Q15111 | 5334 |
| PLCL2 | Neurotransmitter | Signaling | Q9UPRO | 23228 |
| PPP1CB | Neurotransmitter | Signaling | P62140 | 5500 |
| PPP1CC | Neurotransmitter | Signaling | P36873 | 5501 |
| PRIMA1 | Neurotransmitter | Biosynthesis | Q86XR5 | 145270 |
| PRKACG | Neurotransmitter | Signaling | P22612 | 5568 |
| PRKAR2B | Neurotransmitter | Signaling | P31323 | 5577 |
| PRKCG | Neurotransmitter | Signaling | P05129 | 5582 |
| PRKX | Neurotransmitter | Signaling | P51817 | 5613 |
| RIC3 | Neurotransmitter | Receptor | Q7Z5B4 | 79608 |
| SHANK3 | Neurotransmitter | Signaling | Q9BYBO | 85358 |
| SLC6A1 | Amine Neuromodulator | Transferase | P30531 | 6529 |
| SLC6A13 | Amine Neuromodulator | Transferase | Q9N5D5 | 6540 |
| Slc6a4 | Serotonin | Transporter | P31645 | 6532 |
| SNX13 | Neurotransmitter | Signaling | Q9Y5W8 | 23161 |
| TAAR1 | Amine Neuromodulator | Receptor | Q96RJ0 | 134864 |
| TAAR2 | Amine Neuromodulator | Receptor | Q9P1 P5 | 9287 |
| TAAR5 | Neurotransmitter | Receptor | O14804 | 9038 |
| TH | Neurotransmitter | Biosynthesis | P07101 | 7054 |
| TPH1 | Neurotransmitter | Biosynthesis | P17752 | 7166 |
| TPH2 | Neurotransmitter | Biosynthesis | Q8IWU9 | 121278 |
| TRHDE | Neurotransmitter | Biosynthesis | Q9UKU6 | 29953 |

TABLE 8

NEUROTRANSMITTERS

| Ligand | Pathway | Type |
|---|---|---|
| 2-Arachidonoylglycerol | Endocannabinoid | Ligand |
| 2-Arachidonyl glyceryl ether | Endocannabinoid | Ligand |
| 3-methoxytyramine | Amines | Ligand |
| Acetylcholine | Amino Acids | Ligand |
| Adenosine | Purine | Ligand |
| Adenosine triphosphate | Purine | Ligand |
| Agmatine | Amino Acids | Ligand |
| Anandamide | Endocannabinoid | Ligand |
| Aspartate | Amino Acids | Ligand |
| Carbon monoxide | Gas | Ligand |
| D-serine | Amino Acids | Ligand |
| Dopamine | Monoamines | Ligand |
| Dynorphin | Opioids | Ligand |
| Endorphin | Opioids | Ligand |
| Enkephalin | Opioids | Ligand |
| Epinephrine | Monoamines | Ligand |
| Gamma-aminobutyric acid | Amino Acids | Ligand |
| Glutamate | Amino Acids | Ligand |
| Glycine | Amino Acids | Ligand |
| Histamine | Monoamines | Ligand |
| N-Acetylaspartylglutamate | Neuropeptides | Ligand |
| N-Arachidonoyl dopamine | Endocannabinoid | Ligand |
| N-methylphenethylamine | Amines | Ligand |
| N-methyltryptamine | Amines | Ligand |
| Nitric oxide | Gas | Ligand |
| Norepinephrine | Monoamines | Ligand |
| Octopamine | Amines | Ligand |
| Phenethylamine | Amines | Ligand |
| Serotonin | Monoamines | Ligand |
| Synephrine | Amines | Ligand |
| Tryptamine | Amines | Ligand |
| Tyramine | Amines | Ligand |
| Virodhamine | Endocannabinoid | Ligand |

TABLE 9A

AGONISTS AND ANTAGONIST AGENTS

| Gene | Agonist | Antagonist |
|---|---|---|
| Adrb2 Accession Number: P07550 | NCX 950 Bitolterol Isoetarine Norepinephrine Phenylpropanolamine Dipivefrin Epinephrine Orciprenaline Dobutamine Ritodrine Terbutaline Salmeterol Formoterol Salbutamol Isoprenaline Arbutamine Arformoterol Fenoterol Pirbuterol Ephedra Procaterol Clenbuterol Bambuterol Indacaterol Droxidopa Olodaterol Vilanterol Pseudoephedrine Cabergoline Mirtazepine | Alprenolol Carvedilol Desipramine Nadolol Levobunolol Metipranolol Bevantolol Oxprenolol Nebivolol Asenapine Bupranolol Penbutolol Celiprolol Pindolol Acebutolol Bopindolol |
| Adra1d Accession Number: P25100 | Midodrine Norepinephrine Clonidine Oxymetazoline Pergolide Bromocriptine Droxidopa Xylometazoline Ergotamine Cirazoline Cabergoline Methoxamine Epinephrine | Dapiprazole Amitriptyline Alfuzosin Promazine Prazosin Imipramine Nortriptyline Doxazosin Nicardipine Dronedarone Tamsulosin Propiomazine Phenoxybenzamine Carvedilol Doxepin Terazosin Quetiapine Methotrimeprazine Silodosin |
| Adrb1 Accession Number: P08588 | Isoetarine Norepinephrine Phenylpropanolamine Epinephrine Dobutamine Salbutamol Isoprenaline Arbutamine Fenoterol Pirbuterol Ephedra Clenbuterol Droxidopa Pseudoephedrine Carteolol Cabergoline Mirtazepine Loxapine Vortioxetine Desipramine | Esmolol Betaxolol Metoprolol Atenolol Timolol Sotalol Propranolol Labetalol Bisoprolol Alprenolol Amiodarone Carvedilol Nadolol Levobunolol Metipranolol Bevantolol Practolol Oxprenolol Celiprolol Nebivolol Asenapine Bupranolol Penbutolol Pindolol Acebutolol Bopindolol Carteol |

TABLE 9A-continued

AGONISTS AND ANTAGONIST AGENTS

| Gene | Agonist | Antagonist |
|---|---|---|
| Adrb3 Accession Number: P13945 | SR 58611 Norepinephrine Epinephrine Isoprenaline Arbutamine Fenoterol Ephedra Clenbuterol Droxidopa Mirabegron | Bopindolol Propranolol Bupranolol |
| Adrbk1 Accession Number: P25098 | ATP Carbachol Dopamine Isoproterenol Morphine DAMGO histamine Acetylcholine Etorphine NMDA Dopamine | Alprenolol Heparin |
| Adrbk2 Accession Number: P26819 | Isoproterenol DAMGO ATP | Propranolol |
| Chrm3 Accession Number: P20309 | cgmp ATP Cevimeline arecoline oxotremorine-M NNC 11-1314 xanomeline oxotremorine pentylthio-TZTP arecaidine propargyl ester NNC 11-1607 furmethide NNC 11-1585 Acetylcholine methylfurmethide Bethanechol Carbachol Succinylcholine ALKS 27 itopride methacholine Meperidine Cinnarizine Trimipramine | MT3 Hexocyclium Himbacine Biperiden lithocholylcholine AFDX384 4-DAMP hexahydrodifenidol VU0255035 N-methyl scopolamine Darifenacin Thiethylperazine methoctramine silahexocyclium Strychnine MT7 Heparin Olanzapine Pirenzepine Clidinium Ipratropium Propantheline Dicyclomine Darifenacin Tiotropium Atropine Scopolamine Amitriptyline Doxepin Lidocaine Nortriptyline Tropicamide Metixene Homatropine Methylbromide Solifenacin Glycopyrrolate Propiomazine Diphemanil Methylsulfate Promethazine Diphenidol Pancuronium Ziprasidone Quetiapine Imipramine Clozapine Cyproheptadine Aripiprazole Nicardipine Amoxapine |

TABLE 9A-continued

AGONISTS AND ANTAGONIST AGENTS

| Gene | Agonist | Antagonist |
|---|---|---|
| | | Loxapine |
| | | Promazine |
| | | Oxyphencyclimine |
| | | Anisotropine |
| | | Methylbromide |
| | | Tridihexethyl |
| | | Chlorpromazine |
| | | Ketamine |
| | | Cyclosporin A |
| | | Paroxetine |
| | | Benzquinamide |
| | | Tolterodine |
| | | Oxybutynin |
| | | Alcuronium |
| | | WIN 62,577 |
| | | Tramadol |
| | | Chlorprothixene |
| | | Aclidinium |
| | | Methotrimeprazine |
| | | Umeclidinium |
| | | Cryptenamine |
| | | Mepenzolate |
| | | Maprotiline |
| | | Brompheniramine |
| | | Isopropamide |
| | | Trihexyphenidyl |
| | | Ipratropium bromide |
| | | Hyoscyamine |
| | | Procyclidine |
| | | Pipecuronium |
| | | Fesoterodine |
| | | Disopyramide |
| | | Desipramine |
| | | Mivacuriurn |
| Chrna3 Accession Number: P32297 | Nicotine Varenicline Acetylcholine Ethanol Cytisine Levamisole Galantamine | A-867744 NS1738 Hexamethonium Mecamylamine Dextromethorphan Pentolinium Levomethadyl Acetate Bupropion |
| Chrna6 Accession Number: Q15825 | Nicotine Cytisine Varenicline Galantamine | Hexamethonium Mecamylamine |
| Chrna9 Accession Number: Q9UGM1 | Nicotine Galantamine Ethanol ATG003 Lobeline RPI-78M | Hexamethonium Mecamylamine Tetraethylammonium Muscarine Strychnine |
| Chrnb1 Accession Number: P11230 | Galantamine | |
| Chrnb4 Accession Number: P30926 | Nicotine Varenicline PNU-120596 Ethanol Galantamine | Atropine Oxybutynin Pentolinium Dextromethorphan |
| Chrng Accession Number: P07510 | Galantamine | |
| Adcyap1 Accession Number: P18509 | Nicotine CGMP Apomorphine Suramin Nifedipine ATP Dihydrotestosterone Maxadilan Dexamethasone Acetylcholine | Atropine PPADS Onapristone Muscarine Haloperidol Astressin Melatonin Scopolamine Tetrodotoxin Apamin |

TABLE 9A-continued

AGONISTS AND ANTAGONIST AGENTS

| Gene | Agonist | Antagonist |
|---|---|---|
| | Histamine | Hexamethonium |
| | Carbachol | Indomethacin |
| | NMDA | Propranolol |
| | Dopamine | Bumetanide |
| | Isoproterenol | Progesterone |
| | Salbutamol | Charybdotoxin |
| | Morphine | Prazosin |
| | Clonidine | |
| | Nimodipine | |
| | 2,6-Diamino-Hexanoic Acid Amide | |
| CYSLTR1 Accession Number: Q9Y271 | Salbutamol Dexamethasone Arachidonic acid Histamine | Montelukast Zafirlukast Cinalukast Pranlukast Nedocromil Theophylline Indomethacin Zileuton Iralukast Pobilukast Sulukast Verlukast |
| LTB4R Accession Number: Q15722 | LTB ATP Dexamethasone cholesterol 20-hydroxy-LTB< 12R-HETE arachidonic acid | U75302 CP105696 CP-195543 Etalocib SC-41930 LY255283 Zafirlukast ONO-4057 RO5101576 BILL 260 |
| PENK Accession Number: P01210 | Dopamine kainate NMDA DAMGO Morphine | Naltrexone Naloxone Progesterone |
| Htr2c Accession Number: P28335 | Apomorphine Bifeprunox Tramadol AL-37350A 5-MeO-DMT BW723086 CGS-12066 DOI 5-CT YM348 LSD xanomeline WAY-163909 Dopamine LY344864 VER-3323 TFMPP 8-OH-DPAT MK-212 NMDA org 12962 5-MeOT RU 24969 Acetylcholine QUINPIROLE quipazine tryptamine Ro 60-0175 Oxymetazoline Ergotamine Cabergoline Lorcaserin Pergolide Methylergonovine Renzapride Pramipexole GR-127935 BRL-15572 ipsapirone | Melatonin SB 224289 LY334362 FR260010 Sulpiride Thiethylperazine cyamemazine Mesulergine SB 221284 Zotepine Metergoline methiothepin Spiperone SB 215505 Tiospirone SB 228357 Pizotifen SB 206553 SB 204741 SDZ SER-082 Ritanserin SB 242084 S33084 Roxindole RS-127445 Terguride EGIS-7625 SB 243213 RS-102221 Olanzapine Aripiprazole Agomelatine Ziprasidone Quetiapine Sarpogrelate Perphenazine Thioridazine Sertindole Loxapine |

TABLE 9A-continued

AGONISTS AND ANTAGONIST AGENTS

| Gene | Agonist | Antagonist |
|---|---|---|
| | SB 216641 | Methysergide |
| | SL65.0155 | Risperidone |
| | S 16924 | Asenapine |
| | Bromocriptine | Mianserin |
| | Lisuride | Clozapine |
| | Tegaserod | Trifluoperazine |
| | Epicept NP-1 | Trazodone |
| | dapoxetine | Doxepin |
| | Dexfenfluramine | Nortriptyline |
| | 3,4-Methylenedioxymethamphetamine | Chlorprothixene |
| | Ropinirole | Minaprine |
| | Maprotiline | Propiomazine |
| | Desipramine | Mirtazapine |
| | | Amoxapine |
| | | Yohimbine |
| | | Cyproheptadine |
| | | Imipramine |
| | | Amitriptyline |
| | | Promazine |
| | | Chlorpromazine |
| | | Ketamine |
| | | Propranolol |
| | | Fluoxetine |
| | | Ketanserin |
| | | Mesulergine |
| | | AC-90179 |
| | | Ergoloid mesylate 2 |
| | | Methotrimeprazine |
| | | Paliperidone |
| | | Clomipramine |
| | | Trimipramine |
| | | Captodiame |
| | | Nefazodone |
| GABA Receptor Accession Numbers (Q9UBS5, O95166, O75899, P28472, P18507, P47870, P47869, O14764) | Bamaluzole | bicuculline |
| | GABA | Metrazol |
| | Gabamide | Flumazenil |
| | GABOB | Thiothixene |
| | Gaboxadol | Bupropion |
| | Ibotenic acid | Caffeine |
| | Isoguvacine | |
| | Isonipecotic acid | |
| | Muscimol | |
| | Phenibut | |
| | Picamilon | |
| | Progabide | |
| | Quisqualamine | |
| | SL 75102 | |
| | Thiomuscimol | |
| | Alcohols (e.g., ethanol, isopropanol) | |
| | Avermectins (e.g., ivermectin) | |
| | Barbiturates (e.g., phenobarbital) | |
| | Benzodiazepines | |
| | Bromides (e.g., potassium bromide | |
| | Carbamates (e.g., meprobamate, carisoprodol) | |
| | Chloralose | |
| | Chlormezanone | |
| | Clomethiazole | |
| | Dihydroergolines (e.g., ergoloid (dihydroergotoxine)) | |
| | Etazepine | |
| | Etifoxine | |
| | Imidazoles (e.g., etomidate) | |
| | Kavalactones (found in kava) | |
| | Loreclezole | |
| | Neuroactive steroids (e.g., allopregnanolone, ganaxolone) | |
| | Nonbenzodiazepines (e.g., zaleplon, zolpidem, zopiclone, eszopiclone) | |
| | Petrichloral | |
| | Phenols (e.g., propofol) | |
| | Piperidinediones (e.g., glutethimide, methyprylon) | |
| | Propanidid | |
| | Pyrazolopyridines (e.g., etazolate) | |
| | Quinazolinones (e.g., methaqualone) | |
| | Skullcap constituents | |
| | Stiripentol | |
| | Sulfonylalkanes (e.g., sulfonmethane, tetronal, trional) | |
| | Valerian constituents (e.g., valeric acid, valerenic acid) | |
| | Volatiles/gases (e.g., chloral hydrate, chloroform, diethyl ether, sevoflurane) | |
| Glutamate Receptor Accession Number: (P42261, P39086, P39086, Q13585, P42261, P42262, P42263, P48058, P39086, Q13002, Q13003, Q13003, Q16478, Q12879, Q14957, Q13224, Q14957, O15399, Q8T0U5, O60391) | 3,5-dihydroxyphenylglycine | APICA |
| | eglumegad | EGLU |
| | Biphenylindanone A | LY-341,495 |
| | DCG-IV | |
| | L-AP4 | |
| CNR1/ CNR2 Accession Number: (P21554, P34972) | N-Arachidonoylethanolamine | SR 141716A |
| | 2-Arachidonoyl-glycerol | LY-320135 |
| | 2-Arachidonoyl-glycerylether | AM251 |
| | N-Arachidonoyl-dopamine | AM281 |
| | O-Arachidonoyl-ethanolamine | SR 144528 |
| | N-Arachidonoylethanolamine | AM630 |
| | 2-Arachidonoyl-glycerol | |
| | 2-Arachidonoyl-glycerylether | |
| | N-Arachidonoyl-dopamine | |
| | O-Arachidonoyl-ethanolamine | |
| | Δ-9-THC | |
| | CP-55,940 | |
| | R(+)-WIN 55,212-2 | |
| | HU-210 | |
| | Levonantradol | |
| | Nabilone | |
| | Methanandamide | |
| | ACEA | |
| | O-1812 | |
| | Δ9-THC | |
| | CP-55,940 | |
| | R(+)-WIN 55,212-2 | |
| | HU-210 | |
| | Levonantradol | |
| | Nabilone | |
| | Methanandamide | |
| | JWH-015 | |
| | JWH-133 | |

TABLE 9B

ADRENERGIC AGONISTS AND ANTAGONISTS

| Receptor | Agonist | Antagonist |
|---|---|---|
| Non-selective | adrenaline (epinephrine), noradrenaline (norepinephrine), isoprenaline (isoproterenol), dopamine, caffeine, nicotine, tyramine, methylphenidate, ephedrine and pseudophedrine. | carvedilol, arotinolol, and labetalol |
| α1 selective (ADRA1A, ADRA1B, ADRA1D) | phenylephrine, methoxamine, midodrine, cirazoline, xylometazoline, metaraminol chloroehtylclonidine, oxymetazoline trozodone, amitryptyline, silodosin, clomipramine, doxepin, trimipramine, typical and atypical antipsychotics, and antihistamines, such as hyroxyzine | acepromazine, alfuzosin, doxazosin, labetalol, phenoxybenzamine, KW3902, phentolamine, prazosin, tamsulosin, terazosin, tolazoline, |
| α2 selective (ADRA2A, ADRA2B, ADRA2C) | α-methyl dopa, clonidine, brimonidine, agmatine, dexmedetomidine, medetomidine, romifidine chloroethylclonidine, detomidine, lofexidine, xylazine, tizanidine, guanfacine, and amitraz | phentolamine, phenoxybenzamine, yohimbine, idazoxan, atipamezole, mirtazapine, tolazoline, trazodone, and typical and atypical antipsychotics |
| β1 selective (ADRB1) | Dobutamine | metroprolol, atenolol, acebutolol, bisoprolol, betaxolol, levobetaxolol, esmolol, celiprolol, carteolol, landiolol, oxprenolol, propanolol, practolol, penbutolol, timolol, labetalol, nebivolol, levobunolol, nadolol, pindolol, sotalol, metipranolol, tertatolol, vortioxene |
| β2 selective (ADRB2) | salbutamol, albuterol, bitolterol mesylate, levabuterol, ritodrine, metaproterenol, terbutaline, salmeterol, formoterol, and pirbuterol | butaxamine, acebutolol, timolol, propanolol, levobunolol, carteolol, labetalol, pindolol, oxprenolol, nadolol, metipranolol, penbutolol, tertatolol, sotalol |
| β3 selective (ADRB3) | L-796568, amibegron, solabegron, mirabegron | SR 59230A, arotinolol |

TABLE 9C

DOPAMINE AGONISTS AND ANTAGONISTS

| Receptor | Agonist | Antagonist |
|---|---|---|
| Non-selective | pramipexole, ropinirole, rotigotine, apomorphine, propyl-norapomorphine, bromocriptine, cabergoline, ciladopa, dihydrexidine, dinapsoline, doxamthrine, epicriptine, lisuride, pergolide, piribedil, quinagolide, roxindole, dopamine | haloperidol, paliperidone, clozapine, risperidone, olanzapine, quetiapine, ziprasidone, metoclopramide, droperidol, domperidone, amoxapine, clomipramine, trimipramine, choline, melatonin, acepromazine, amisulpride, asenapine, azaperone, benperidol, bromopride, butaclamol, chlorpromazine, clebopride, chlorprothixene, clopenthixol, clocapramine, eticlopride, flupenthixol, fluphenazine, fluspirilene, hydroxyzine, itopride, iodobenzamide, levomepromazine, levosulpiride, loxapine, mesoridazine, metopimazine, mosapramine, nafadotride, nemonapride, penfluridol, perazine, perphenazine, pimozide, prochlorperazine, promazine, pipotiazine, raclopride, remoxipride, spiperone, spiroxatrine, stepholidine, sulpiride, sultopride, tetrahydropalmatine, thiethylperazine, thioridazine, thiothixene, tiapride, trifluoperazine, trifluperidol, triflupromazine, thioproperazine, taractan, zotepine, zuclopenthixol, ziprasidone, ANP-010, NGD-94-4 |
| D1 (DRD1) | Fenoldopam, A-86929, dihydrexidine, dinapsoline, dinoxyline, doxanthrine, SKF-81297, SKF-82958, SKF-38393, G-BR-APB, dopexamine | SCH-23,390, SKF-83,959, Ecopipam, Clebopride, Flupenthixol, Zuclopenthixol, Taractan, PSYRX-101, LuAF-35700, GLC-756, ADX10061, Zicronapine |
| D2 (DRD2) | Cabergoline, pergolide, quinelorane, sumanirole, talipexole, piribedil, quinpirole, quinelorane, dinoxyline, dopexamine | Chloroethylnorapomorphine, desmethoxyfallypride, domperidone, eticlopride, fallypride, hydroxyzine, itopride, L-741,626, SV 293, yohimbine, raclopride, sulpiride, paliperidone, penfluridol, quetiapine, lurasidone, risperidone, olanzapine, blonanserin, perphenazine, metoclopramide, trifluoperazine, clebopride, levosulpiride, flupentixol, haloperidol, thioridazine, alizapride, amisulpride, asenapine, bromopride, bromperidol, clozapine, fluphenazine, perphanazine, loxapine, nemonapride, pericyazine, pipamperone, prochlorperazine, thioproperazine, thiethylperazine, tiapride, ziprasidone, zuclopenthixol, taractan, fluanisone, melperone, molindone, remoxipride, sultopride, ALKS 3831, APD-403, ONC201, pridopidine, DSP-1200, NG-101, TAK-906, ADN-1184, ADN-2013, AG-0098, DDD-016, IRL-626, KP303, ONC-206, PF-4363467, PGW-5, CG-209, ABT-925, AC90222, ACP-005, ADN-2157, CB030006, CLR-136, Egis-11150, Iloperidone, JNJ-37822681, DLP-115, AZ-001, S-33138, SLV-314, Y-931, YKP1358, YK-P1447, APD405, CP-903397, ocaperidone, zicronapine, TPN-902 |
| D3 (DRD3) | Piribedil, quinpirole, captodiame, compound R, R-16, FAUC 54, FAUC 73, PD-128,907, PF-219,061, PF-592,379, CJ-1037, FAUC 460, FAUC 346, cariprazine | Domperidone, FAUC 365, nafadotride, raclopride, PNU-99,194, SB-277011-A, sulpiride, risperidone, YQA14, U99194, SR 21502, levosulpiride, amisulpride, nemonapride, ziprasidone, taractan, sultopride, APD-403, F17464, ONC201, NG-101, TAK-906, ONC-206, PF-4363467, ABT-127, ABT-614, GSK-598809, GSK-618334, S-14297, S-33138, YKP1358, YK-P1447 |
| D4 (DRD4) | WAY-100635, A-412,997, ABT-724, ABT-670, FAUC 316, PD-168, 077, CP-226,269 | A-381393, FAUC 213, L-745,870, L-570,667, ML-398, fananserin, clozapine, PNB-05, SPI-376, SPI-392, Lu-35-138, NGD-94-1 |
| D5 (DRD5) | Dihydrexidine, rotigotine, | SCH 23390 |

TABLE 9C-continued

DOPAMINE AGONISTS AND ANTAGONISTS

| Receptor | Agonist | Antagonist |
|---|---|---|
| Partial | SKF-83,959, fenoldopam, aplindore, brexpiprazole, aripiprazole, CY-208,243, pardoprunox, phencyclidine, and salvinorin A | |

TABLE 9D

GABA AGONISTS AND ANTAGONISTS

| Receptor | Agonist | Antagonist |
|---|---|---|
| GABAA | barbiturates (e.g., allobarbital, amobarbital, aprobarbital, alphenal, barbital, brallobarbital, phenobarbital, secobarbital, thiopental), bamaluzole, GABA, GABOB, gaboxadol, ibotenic acid, isoguvacine, isonipecotic acid, muscimol, phenibut, picamilon, progabide, quisqualamine, SL 75102, thiomuscimol, positive allosteric modulators (PAMs) (e.g., alcohols, such as ethanol and isopropanol; avermectins, such as ivermectin; benzodiazepines, such as diazepam, alprazolam, chlordiazepoxide, clonazepam, flunitrazepam, lorazepam, midazolam, oxazepam, prazepam, brotizolam, triazolam, estazolam, lormetazepam, nitrazepam, temazepam, flurazepam, clorazepate halazepam, prazepam, nimetazapem, adinazolam, and climazolam; bromides, such as potassium bromide; carbamates, such as meprobamate and carisoprodol; chloralose; chlormezanone; chlomethiazole; dihydroergolines, such as ergoloid; etazepine; etifoxine; imidazoles, such as etomidate; imidazopyridines, such as alpidem and necopdiem; kavalactones; loreclezole; neuroactive steroids, such as allogregnanolone, pregnanolone, dihydrodeoxycorticosterone, tetrahydrodeoxycortisosterone, androstenol, androsterone, etiocholanolone, 3α-androstanediol, 5α, 5β, or 3α-dihydroprogesterone, and ganaxolone; nonbenzodiazepines, such as zalepon, zolpidem, zopiclone, and eszopiclone); petrichloral; phenols, such as propofol; piperidinediones, such as glutethimide and methyprylon; propanidid; pyrazolopyridines, such as etazolate; pyrazolopyrimidines, such as divaplon and fasiplon; cyclopyrrolones, sush as pagoclone and suproclone; ß-cabolines, such as abecarnil and geodecarnil; quinazolinones, such as methaqualone; Scutellaria constituents; stiripentol; sulfonylalkanes, such as sulfonomethane, teronal, and trional; Valerian constituents, such as valeric acid and valerenic acid; and gases, such as chloral hydrate, chloroform, homotaurine, diethyl ether, and sevoflurane. | bicuculline, gabazine, hydrastine, pitrazepin, sinomenine, tutin, thiocolchicoside, metrazol, securinine, gabazine |
| GABAB | 1,4-butanediol, baclofen, GABA, Gabamide, GABOB, gamma-butyrolactone, gamma-hydroxybutyric acid, gamma-hyrdoxyvaleric acid, gamma-valerolactone, isovaline, lesogaberan, phenibut, picamilon, progabide, homotaurine, SL-75102, tolgabide | CGP-35348, homotaurine, phaclofen, saclofen, and SCH-50911 |
| GABAA-ρ | CACA, CAMP, GABA, GABOB, N4-chloroacetylcytosine arabinoside, picamilon, progabide, tolgabide, and neuroactive steroids, such as allopregnanolone, THDOC, and alphaxol one | gabazine, gaboxadol, isonipecotic acid, SKF-97,541, and (1,2,5,6-Tetrahydropyridin-4-yl)methylphosphinic acid |

TABLE 7E

MUSCARINC AGONISTS AND ANTAGONISTS

| Receptor | Agonist | Antagonist |
|---|---|---|
| Chrm1 | AF102B, AF150(S), AF267B, acetylcholine, carbachol, cevimeline, muscarine, oxotremorine, pilocarpine, vedaclidine, 77-LH-28-1, CDD-0097, McN-A-343, L689,660, and xanomeline | atropine, dicycloverine, hyoscyamine, ipratropium, mamba toxin muscarinic toxin 7 (MT7), olanzapine, oxybutynin, pirenzepine, telenzepine, and tolterodine |
| Chrm2 | acetylcholine, methacholine, iper-8-naph, berbine, and (2S,2'R,3'S,5'R)-1-methyl-2-(2-methyl-1,3-oxathiolan-5-yl)pyrrolidine 3-sulfoxide methyl iodide | atropine, dicycloverine, hyoscyamine, otenzepad, AQRA-741, AFDX-384, thorazine, diphenhydramine, dimenhydrinate, ipratropium, oxybutynin, pirenzepine, methoctramine, tripitramine, gallamine, and tolterodine |
| Chrm3 | acetylcholine, bethanechol, carbachol, L689, 660, oxotremorine, pilocarpine, aceclidine, arecoline, and cevimeline | atropine, dicycloverine, hyoscyamine, alcidium bromide, 4-DAMP, darifenacin, DAU-5884, HL-031,120, ipratropium, J-104,129, oxybutynin, tiotropium, zamifenacin, and tolterodine |
| Chrm4 | acetylcholine, carbachol, and oxotremorine), and Chrm5 agonists (e.g., acetylcholine, milameline, sabcomeline | AFDX-384, dicycloverine, himbacine, mamba toxin 3, PD-102,807, PD-0298029, and tropicamide |
| Chrm5 | acetylcholine, milameline, sabcomeline | VU-0488130, xanomeline |
| Non-selective | | scopolamine, hydroxyzine, doxylamine, dicyclomine, flavoxate, cyclopentolate, atropine methonitrate, trihexyphenidyl/benzhexol, solifenacin, benzatropine, mebeverine, and procyclidine |

TABLE 9F

NICOTINIC AGONISTS AND ANTAGONISTS

| Receptor | Agonist | Antagonist |
|---|---|---|
| Chrna receptors | choline, acetylcholine, carbachol, methacholine, nicotine, varenicline tartrate, galantamine hydrobromide, suxamethonium chloride (succinylcholine chloride), epibatidine, iobeline, decamethonium, isopronicline/TC-1734/AZD3480 (TC-1734), AZD1446 (TC-6683), TC-5619, TC-5214, MEM 3454 (RG3487), ABT-894, ABT-560, EVP-6124, EVP-4473, PNU-282987, AR-R17779, SSR 189711, JN403, ABBF, PHA-543613, SEN12333, GTS-21/DMXB-A, AZD0328, A-582941, ABT-418, 5-iodo-A-85380, SIB-1765F, ABT-089, and ABT-594 | turbocurarine, bupropion, mecamylamine, 18-methozycoronaridine, hexamethonium, trimethaphan, atraciurium, doxacurium, mivacurium, pancuronium, vecuronium, succinylcholine, dextromethorphan, neramexane, dextrophan, and 3-methoxymorphinan |

TABLE 9G

GLUATAMATE RECEPTOR AGONISTS AND ANTAGONISTS

| Receptor | Agonist | Antagonist |
|---|---|---|
| Ionotropic (GRIA-14, GRIK1-5, and GRIN1-3B) | AMPA, glutamic acid, ibotenic acid, kainic acid, NMDA, quisqualic acid | AP5, AP7, CPPene, selfotel, HU-211, Huperzine A, gabapentin, remacemide, amantadine, atomoxetine, AZD6765, agmatine, chloroform, dextrallorphan, dextromethorphan, dextrorphan, diphenidine, dizocilpine (MK-801), ethanol, eticyclidine, gacyclidine, ibogaine, ifenprodil, ketamine, kynurenic acid, memantine, magnesium, methoxetamine, nitromemantine, nitrous oxide, PD-137889, perampanel, phencyclidine, rolicyclidine, tenocyclidine, methoxydine, tiletamine, neramexane, eliprodil, etoxadrol, dexoxadrol, WMS-2539, NEFA, delucemine, 8A-PDHQ, aptiganel, rhynchophylline |
| Metabotropic (GRM1-8) | L-AP4, ACPD, L-QA, CHPG, LY-379,268, LY-354,740, ACPT, VU 0155041 | AIDA, fenobam, MPEP, LY-367,385, EGLU, CPPG, MAP4, MSOP, LY-341,495 |
| Glycine antagonists | | rapastinel, NRX-1074, 7-chlorokynurenic acid, 4-chlorokynurenine, 5,7-dichlorokynurenic acid, kynurenic acid, TK-40, 1-aminocyclopropanecarboxylic acid (ACPC), L-phenylalanine, and xenon |

TABLE 9H

HISTAMINE AGONISTS AND ANTAGONISTS

| Receptor | Agonist | Antagonist |
|---|---|---|
| Non-selective | histamine dihydrochloride, HTMT dimaleate, 2-pyridylethlyamine dihydrochloride | |
| $H_1$ | | acrivastine, azelastine, astemizole, bilastine, bromodiphenhydramine, brompheniramine, buclizine, carbinoxamine, cetirizine, cetirizine dihydrochloride, clemastine fumarate, clemizole hydrochloride, chlorodiphenhydramine, chlorphenamine, chlorpromazine, clemastine, cyclizine, cyproheptadine, dexbrompheniramine, dexchlorpheniramine, dimenhydrinate, dimethindene maleate, dimetindene, diphenhydramine, diphenhydramine hydrochloride, doxepin hydrochloride, doxylamine, ebastine, embramine, fexofenadine, fexofenadine hydrochloride, hydroxyzine, ketotifen fumarate, loratadine, meclizine, meclizine dihydrochloride, mepyramine maleate, mirtazapine, olopatadine, olopatadine hydrochloride, orphenadrine, phenindamine, pheniramine, phenyltoloxamine, promethazine, quetiapine, rupatadine, terfenadine, tripelennamine, zotepine, trans-triprolidine hydrochloride, and triprolidine |
| $H_1$ inverse agonists | | cetirizine, levocetirizine, desloratadine, and pyrilamine |
| $H_2$ | betazole, impromidine, dimaprit dihydrochloride, and amthamine dihyrdobromide | aminopotentidine, cimetidine, famotidine, ICI 162,846, lafutidine, nizatidine, ranitidine, ranitidine hyrdochloride, roxatidine, zolantadine dimaleate, and toitidine |
| $H_3$ | imetit dihydropbromide, immepip dihyrdrobromide, immethridine dihydrobromide, α-Methylhistamine dihydrobromide, N-methylhistamine dihydrochloride, proxyfan oxalate, and betahistine | clobenpropit, clobenpropit dihydrobromide, A 3314440 dihyrdochloride, BF 2649 hydrochloride, carcinine ditrifluoroacetate, ABT-239, ciprofaxin, conessine, GT 2016, A-349,821, impentamine dihydrobromide, iodophenpropit dihydrobromide, JNJ 10181457 dihydrochloride, JNJ 5207852 dihydrochloride, ROS 234 dioxalate, SEN 12333, VUF 5681 dihydrobromide, and thioperamide |
| $H_4$ | imetit dihydropbromide, immepip dihyrdrobromide, 4-methylhistamine dihydrochloride, clobenpropit dihydrobromide, VUF 10460, and VUF 8430 dihydrobromide | thioperamide, JNJ 7777120, A 943931 dihydrochloride, A 987306, JNJ 10191 584 maleate, and VUF-6002 |

TABLE 9I

CANNABINOID AGONISTS AND ANTAGONISTS

| Receptor | Agonist | Antagonist |
|---|---|---|
| Cannabinoid receptor (non-selective) | Anandamide, N-Arachidonoyl dopamine, 2-Arachidonoylglycerol (2-AG), 2-Arachidonyl glyceryl ether, Δ-9-Tetrahydrocannabinol, EGCG, Yangonin, | |

TABLE 9I-continued

CANNABINOID AGONISTS AND ANTAGONISTS

| Receptor | Agonist | Antagonist |
|---|---|---|
| | AM-1221, AM-1235, AM-2232, UR-144, JWH-007, JWH-015, JWH-018, ACEA, ACPA, arvanil, CP 47497, DEA, leelamine, methanandamide, NADA, noladin ether, oleamide, CB 65, GP-1a, GP-2a, GW 405833, HU 308, JWH-133, L-759,633, L-759,656, LEI 101, MDA 19, and SER 601 | |
| $CB_1$ receptor | ACEA, ACPA, RVD-Hpα, (R)-(+)-methanandamide | rimonabant, cannabidiol, $\Delta^9$-tetrahydrocannabivarin (THCV), taranabant, otenabant, surinabant, rosonabant, SLV-319, AVE1625, V24343, AM 251, AM 281, AM 6545, hemopressin, LY 320135, MJ 15, CP 945598, NIDA 41020, PF 514273, SLV 319, SR 1141716A, and TC-C 14G |
| $CB_2$ receptor | CB 65, GP 1a, GP 2a, GW 405833, HU 308, JWH 133, L-759,656, L-759,633, SER 601, LEI 101 | cannabidiol, $\Delta^9$-tetrahydrocannabivarin (THCV), AM 630, COR 170, JTE 907, and SR 144528 |

TABLE 9J

PURINERGIC RECEPTOR AGONISTS AND ANTAGONISTS

| Receptor | Agonist | Antagonist |
|---|---|---|
| ADORA1 (P1 adenosine receptor) | Adenosine, N6-Cyclopentyladenosine, N6-3-methoxyl-4-hydroxybenzyl adenine riboside (B2), CCPA, tecadenoson, selodenoson, Certain Benzodiazepines and Barbiturates, 2'-MeCCPA, GR 79236, and SDZ WAG 994 | Caffeine, theophylline, 8-Cyclopentyl-1,3-dimethylxanthine (CPX), 8-Cyclopentyl-1,3-dipropylxanthine (DPCPX), 8-Phenyl-1,3-dipropylxanthine, bamifylline, BG-9719, BG09928, FK-453, FK838, rolofylline, N-0861, and PSB 36 |
| ADORA2A (P1 adenosine receptor) | Adenosine, N6-3-methoxyl-4-hydroxybenzyl adenine riboside (B2), YT-146, DPMA, UK-423,097, limonene, NECA, CV-3146, binodenoson, ATL-146e, CGS-21680, and Regadenoson | Caffeine, theophylline, istradefylline, SCH-58261, SCH-442,416, ATL-444, MSX-3, preladenant, SCH-412,348, VER-6623, VER-6947, VER-7835, vipadenant, and ZM-241,385 |
| ADORA2B (P1 adenosine receptor) | Adenosine, 5'-N-ethyl-carboxamidoadenosine, BAY 60-6583, LUF-5835, NECA, (S)-PHPNECA, and LUF-5845 | Caffeine, theophylline, CVT-6883, ATL-801, compound 38, MRS-1706, MRS-1754, OSIP-339,391, PSB-603, PSB-0788, and PSB-1115 |
| ADORA3 (P1 adenosine receptor) | Adenosine, 2-(1-Hexynyl)-N-methyladenosine, CF-101 (IB-MECA), CF-102, 2-C1-1B-MECA, CP-532,903, inosine, LUF-6000, and MRS-3558 | Caffeine, theophylline, MRS-1191, MRS-1220, MRS-1334, MRS-1523, MRS-3777, MRE3008F20, MRE3005F20, OT-7999, SSR161421, KF-26777, PSB-10, PSB-11, and VUF-5574 |
| P2Y receptor | ATP, ADP, UTP, UDP, UDP-glucose, 2-methylthioladenosine 5' diphosphate (2-MeSADP), lysophosphatidic acid, PSB 1114, PSB 0474, NF 546, MRS 2365, MRS 2690, MRS 2693, MRS 2768, MRS 2905, MRS 2957, MRS 4062, and denufosol ($P2Y_2$ agonist) | clopidogrel, elinogrel, prasugrel, ticlopidine, ticagrelor, AR-C 118925XX, AR-C 66096, AR-C 69931, AZD 1283, MRS 2179, MRS 2211, MRS 2279, MRS 2500, MRS 2578, NF 157, NF 340, PPADS, PPTN hydrochloride, PSD 0739, SAR 216471, and suramin |
| P2X receptor | ATP | A 438079, A 740003, A 804598, A 839977, AZ 10606120, AZ 11645373, 5-BDBD, BX 430, Evans Blue, JNJ 47965567, KN-62, NF 023, NF 110, NF 157, NF 279, NF 449, PPADS, iso-PPADS, PPNDS, Ro 0437626, Ro 51, RO-3, TC-P 262, suramin, TNP-ATP, and $P2X_7$ antagonists NF279, calmidazolium, and KN-62 |

TABLE 10

| Type | Modulators |
|---|---|
| Norepinephrine reuptake inhibitors (increase adrenergic neurotransmission) | amedalin, atomoxetine, CP-39,332, daledalin, edivoxetine, esreboxetine, lortalamine, nisoxetine, reboxetine, talopram, talsupram, tandamine, viloxazine, bupropion, ciclazindol, manifaxine, maprotiline, radafaxine, tapentadol, teniloxazine, protriptyline, nortriptyline, and desipramine |
| Norepineprhine-dopamine reuptake inhibitors (increase adrenergic and dopamine neurotransmission) | amineptine, bupropion, desoxypipradrol, dexmethylphenidate, difemetorex, diphenylprolinol, ethylphenidate, fencamfamine, fencamine, lefetamine, methylenedioxypyrovalerone, methylphenidate, nomifensine, O-2172, oxolinic acid, pipradrol, prolintane, pyrovalerone, tametraline, and WY-46824 |
| Serotonin-norepinephrine-dopamine reuptake inhibitors (SNDRIs) and serotonin-norepinephrine reuptake inhibitors (SNRIs) (increase adrengergic, dopamine, and serotonin neurotransmission) | mazindol, nefazodone, sibutramine, venlafaxine, esketamine, duloxetine, ketamine, phencyclidine, tripelennamine, mepiprazole, amitifadine, AN788, ansofaxine, centanafadine, atomoxetine, desvenlafaxine, milnacipran, levomilnacipran, dasotraline, Lu AA34893, Lu AA37096, NS-2360, tedatioxetine, tesofensine, bicifadine, BMS- |

TABLE 10-continued

| Type | Modulators |
|---|---|
| | 866,949, brasofensine, diclofensine, DOV-216,303, EXP-561, liafensine, NS-2359, RG-7166, SEP-227,162, SEP-228,425, SEP-228,432, naphyrone, 3,3-Diphenylcyclobutanamine, 3,4-Dichlorotametraline, D-161, desmethylsertraline, DMNPC, DOV-102,677, fezolamine, GSK1360707F, indatraline, JNJ-7925476, JZ-IV-10, JZAD-IV-22, LR-5182, methylnaphthidate, MI-4, PRC200-SS, PRC050, PR0025, SKF-83,959, TP1, phenyltropanes (e.g., WF-23, dichloropane, and RTI-55), Ginkgo biloba extract, St John's Wort, hyperforin, adhyperforin, and uliginosin B |
| Dopamine reuptake inhibitors (increase dopamine neurotransmission) | Dopamine reuptake inhbiitors (e.g., altropane, amfonelic acid, amineptine, BTCP, 3O-PEP, DBL-583, difluoropine, GBR-12783, GBR-12935, GBR-13069, GBR-13098, GYKI-52895, lometopane, methylphenidate, ethylphenidate, modafinil, armodafinil, RTI-229, vanoxerine, adrafinil, benztropine, bupropion, fluorenol, medifoxamine, metaphit, rimcazole, venlafaxine, Chaenomeles speciosa, and oroxylin A), dopamine releasing agents (e.g., p-Tyramine), dextroamphetamine, lisdexamfetamine, dexmethylphenidate, and cathinone |
| Dopamine prodrugs (increase dopamine neurotransmission) | Levopoda, docarpamine |
| GABA reuptake inhibitors (increase GABA neurotransmission) | CL-996, deramciclane, gabaculine, guvacine, nipecotic acid, NNC-711, NNC 05-2090, SKF-89976A, SNAP-5114, tiagabine, and hyperforin |
| GABA analogs (increase GABA neurotransmission) | gabapentin, butyric acid, valproic acid, valpromide, valnoctamide, 3-hydroxybutanal, GHB, sodium, oxybate, aceburic acid, GBL, GHBAL, GHV, GVL, GHC, GCL, HOCPCA, UMB68, pregabalin, tolibut, phaclofen, sacolfen, arecaidine, gaboxadol, isonipecotic acid, 3-Methyl-GABA, AABA, BABA, DAVA, GAVA, Glutamic acid, hopantenic acid, piracetam, and vigabatrin |
| GABA prodrugs (increase GABA neurotransmission) | L-Glutamine, N-Isonicotinoyl-GABA, picamilon, progabide, tolgabide |
| Acetylcholinesterase inhibitors (increase nicotinic and muscarinic neurotransmission) | carbamates, physostigmine, neostigmine, pyridostigmine, ambenonium, demecarium, rivastigmine, phenanthrene derivatives, galantamine, caffeine, rosmarinic acid, alpha-pinene, piperidines, donepezil, tacrine, edrophonium, Huperzine A, ladostigil, ungeremine, lactucopicrin, dyflos, echothiophate, parathion, and quasi-irreversible acetylcholinesterase inhibitors |
| Serotonin reuptake inhibitors (increase serotonin neurotransmission) | alaproclate, cericlamine, citalopram, dapoxetine, escitalopram, femoxetine, fluoxetine, fluvoxamine, ifoxetine, indalpine, omiloxetine, panuramine, paroxetine, pirandamine, RTI-353, sertraline, zimelidine, desmethylcitalopram, didesmethylcitalopram, seproxetine ((S)-norfluoxetine), desvenlafaxine, cianopramine, litoxetine, lubazodone, SB-649,915, trazodone, vilazodone, vortioxetine, dextromethorphan, dextropropoxyphene, dimenhydrinate, diphenhydramine, mepyramine (pyrilamine), mifepristone, delucemine, mesembrenone, mesembrine, roxindole, duloxetine, levomilnacipran, milnacipran, dapoxetine, sibutramine, chlorpheniramine, dextropmethorphan, and methadone |
| Serotonin releasing agents (increase serotonin neurotransmission) | chlorphentermine, cloforex, dexfenfluramine, etolorex, fenfluramine, flucetorex, indeloxazine, levofenfluramine, tramadol, carbamazepine, amiflamine (FLA-336), viqualine (PK-5078), 2-Methyl-3,4-methylenedioxyamphetamine (2-Methyl-MDA), 3-Methoxy-4-methylamphetamine (MMA), 3-Methyl-4,5-methylenedioxyamphetamine (5-Methyl-MDA), 3,4-Ethylenedioxy-N-methylamphetamine (EDMA), 4-Methoxyamphetamine (PMA), 4-Methoxy-N-ethylamphetamine (PMEA), 4-Methoxy-N-methylamphetamine (PMMA), 4-Methylthioamphetamine (4-MTA), 5-(2-Aminopropyl)-2,3-dihydrobenzofuran (5-APDB), 5-Indanyl-2-aminopropane (IAP), 5-Methoxy-6-methylaminoindane (MMAI), 5-Trifluoromethyl-2- |

TABLE 10-continued

| Type | Modulators |
|---|---|
| | aminoindane (TAI), 5,6-Methylenedioxy-2-aminoindane (MDAI), 5,6-Methylenedioxy-N-methyl-2-aminoindane (MDMAI), 6-Chloro-2-aminotetralin (6-CAT), 6-Tetralinyl-2-aminopropane (TAP), 6,7-Methylenedioxy-2-aminotetralin (MDAT), 6,7-Methylenedioxy-N-methyl-2-aminotetralin (MDMAT), N-Ethyl-5-trifluoromethyl-2-aminoindane (ETAI), N-Methyl-5-indanyl-2-aminopropane, aminorex, MDMA, MDEA, MDA, MBDB, and tryptamines, such as DMT, aMT, 5MeO-NMT, NMT, NETP, Dimethyl-Serotonin, 5MeO-NET, αET and αMT |
| Excitatory amino acid reuptake inhibitors (increase Glutamate receptor neurotransmission) | didydrokanic acid, WAY-213,613, L-trans-2,4-PDC, amphetamine, and L-Theanine |
| Glycine reuptake inhibitors (increase Glutamate receptor neurotransmission) | bitopertin, Org 24598, Org 25935, ALX-5407, sacrosine, Org 25543, and N-arachidonylglycerine |
| Histidine decarboxylase inhibitors (decrease histamine neurotransmission) | Tritoqualine, catechin |
| Endocannabinoid enhancers (increase cannabinoid neurotransmission) | AM404, fatty acid amide hydrolase inhibitors (e.g., AM374, ARN2508, BIA 10-2472, BMS-469908, CAY-10402, JNJ-245, JNJ-1661010, JNJ-28833155, JNJ-40413269, JNJ-42119779, JNJ-42165279, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597, URB694, URB937, VER-156084, and V-158866 |
| Monoacylglycerol lipase inhibitors (increase cannabinoid neurotransmission) | N-arachidonoyl maleimide, JZL184 |
| Endocannabinoid transporter inhibitors (increase cannabinoid neurotransmission) | SB-FI-26 |
| Endocannabinoid reuptake inhibitors (increase cannabinoid neurotransmission) | AM404, AM1172, LY-2183240, O-2093, OMDM-2, UCM-707, VDM-11, guineensine, ETI-T-24_B_I, WOBE437, and RX-055 |
| Adenosine uptake inhibitors (increase purinergic neurotransmission) | cilostazol, dilazep, and dipyramidole |
| Nucleoside transporter inhibitors (increase purinergic neurotransmission) | 8MDP, Decynium 22, 5-iodotubercidin, NBMPR, and TC-T 6000 |

In some embodiments, the neurotransmission activator is a neurotoxin listed in Table 11, or a functional fragment or variant thereof. Neurotoxins include, without limitation, convulsants, nerve agents, parasympathomimetics, and uranyl compounds. Neurotoxins may be bacterial in origin, or fungal in origin, or plant in origin, or derived from a venom or other natural product. Neurotoxins may be synthetic or engineered molecules, derived de novo or from a natural product. Suitable neurotoxins include but are not limited to botulinum toxin and conotoxin. Exemplary neurotoxins are listed in Table 11.

TABLE 11

NEUROTOXINS 2,4,5-Trihydroxyamphetamine
2,4,5-Trihydroxymethamphetamine
3,4-Dichloroamphetamine
5,7-Dihydroxytryptamine
5-Iodowillardiine
Ablomin
Aconitine
Aconitum
Aconitum anthora
AETX
Agelenin
Agitoxin
Aldrin
Alpha-Methyldopamine
Alpha-neurotoxin
Altitoxin
Anatoxin-a
Androctonus australis hector insect toxin
Anisatin
Anthopleurin
Antillatoxin
Anuroctoxin
Apamin
Arum italicum
Arum maculatum
Babycurus toxin 1
Batrachotoxin
BDS-1
Bestoxin
Beta-Methylamino-L-alanine
BgK
Birtoxin
BmKAEP
BmTx3
BotIT2
BotIT6
Botulinum toxin
Brevetoxin
Bukatoxin
Butantoxin
Calcicludine
Calciseptine
Calitoxin
Caramboxin
Carbon disulfide
CgNa toxin
Charybdotoxin
Cholera toxin
Cicutoxin
Ciguatoxin

TABLE 11-continued

NEUROTOXINS

Cll1
Clostridium botulinum
Clostridium difficile toxin A
Conantokins
Conhydrine
Coniine
Conotoxin
Contryphan
Cssll
CSTX
Curare
Cyanide poisoning
Cylindrospermopsin
Cypermethrin
Delta atracotoxin
Dendrotoxin
Dieldrin
Diisopropyl fluorophosphates
Dimethylmercury
Discrepin
Domoic acid
Dortoxin
DSP-4
Ergtoxin
Falcarinol
Fenpropathrin
Gabaculine
Ginkgotoxin
Grammotoxin
Grayanotoxin
Hainantoxin
Halcurin
Hefutoxin
Helothermine
Heteroscodratoxin-1
Histrionicotoxin
Homoquinolinic acid
Hongotoxin
Huwentoxin
Ibotenic acid
Ikitoxin
Inhibitor cystine knot
Jingzhaotoxin
Kainic acid
Kaliseptine
Kappa-bungarotoxin
Kodaikanal mercury poisoning
Kurtoxin
Latrotoxin
Lq2
Maitotoxin
Margatoxin
Maurotoxin
Mercury (element)
Methanol
Methiocarb
MPP+
MPTP
Nemertelline
Neosaxitoxin
Nicotine
N-Methylconiine
Oenanthotoxin
Oxalyldiaminopropionic acid
Oxidopamine
Oxotoxin
Pahutoxin
Palytoxin
Pandinotoxin
Para-Bromoamphetamine
Para-Chloroamphetamine
Para-Chloromethamphetamine
Para-Iodoamphetamine
Penitrem A
Phaiodotoxin
Phenol
Phoneutria nigriventer toxin-3
Phrixotoxin

TABLE 11-continued

NEUROTOXINS

Polyacrylamide
Poneratoxin
Psalmotoxin
Pumiliotoxin
Quinolinic acid
Raventoxin
Resiniferatoxin
Samandarin
Saxitoxin
Scyllatoxin
Sea anemone neurotoxin
Slotoxin
SNX-482
Stichodactyla toxin
Taicatoxin
Taipoxin
Tamapin
Tertiapin
Tetanospasmin
Tetraethylammonium
Tetramethylenedisulfotetramine
Tetrodotoxin
Tityustoxin
Tricresyl phosphate
TsIV
Vanillotoxin
Veratridine Antibodies Neurotransmission modulators also include antibodies that bind to neurotransmitters or neurotransmitter receptors listed in Tables 7 and 8 and decrease neurotransmission. These antibodies include blocking and neutralizing antibodies. Antibodies to neurotransmitters or neurotransmitter receptors listed in Tables 7 and 8 can be generated by those of skill in the art using well established and routine methods.

Neuronal Growth Factor Modulators

In some embodiments, the serotonin receptor inhibitor is administered with a neuronal growth factor modulator (e.g., an agent that decreases or increases neurogenic/axonogenic signals, e.g., a neuronal growth factor or neuronal growth factor mimic, or an agonist or antagonist of a neuronal growth factor or neuronal growth factor receptor). For example, the neuronal growth factor modulator is a neuronal growth factor listed in Table 12, e.g., a neuronal growth factor having the sequence referenced by accession number or Entrez Gene ID in Table 12, or an analog thereof, e.g., a sequence having at least 75%, 80%, 85%, 90%, 90%, 98%, 99% identity to the sequence referenced by accession number or Entrez Gene ID in Table 12. Neuronal growth factor modulators also include agonists and antagonists of neuronal growth factors and neuronal growth factor receptors listed in Table 12. A neuronal growth factor modulator may increase or decrease neurogenesis, neuronal growth, neuronal differentiation, neurite outgrowth, synapse formation, synaptic maturation, synaptic refinement, or synaptic stabilization. Neuronal growth factor modulators regulate tissue innervation (e.g., innervation of a lymph node) and the formation of synaptic connections between two or more neurons and between neurons and non-neural cells (e.g., between neurons and immune cells). A neuronal growth factor modulator may block one or more of these processes (e.g., through the use of antibodies that block neuronal growth factors or their receptors) or promote one or more of these processes (e.g., through the use of neuronal growth factors or analogs thereof). Neuronal growth factor modulators can increase or decrease one of the above-mentioned processes by 10%, 20%, 30%, 40%, 50%, 60%, 70%, 80%, 90%, 95%, 98%, 200%, 500% or more.

In some embodiments, the neuronal growth factor modulator is one that increases neurogenic/axonogenic signals, e.g., the method includes administering to the subject or contacting a cell with a neuronal growth factor modulator in an amount and for a time sufficient to increase neurogenesis or axonogenesis. For example, the neuronal growth factor modulator that leads to an increase in neurogenesis or axonogenesis is a neurotrophic factor. Relevant neurotrophic factors include NGF, BDNF, ProNGF, Sortilin, TGFβ and TGFβ family ligands and receptors (e.g., TGFβR1, TGFβR2, TGFβ1, TGFβ2 TGFβ4), GFRα family ligands and receptors (e.g., GFRα1, GFRα2, GFRα3, GFRα4, GDNF), CNTF, LIF, neurturin, artemin, persephin, neurotrophin, chemokines, cytokines, and others listed in Table 12. Receptors for these factors may also be targeted, as well as downstream signaling pathways including Jak-Stat inducers, and cell cycle and MAPK signaling pathways. In some embodiments, the neuronal growth factor modulator increases neurogenesis, axonogenesis or any of the processes mentioned above by administering, locally delivering, or stabilizing a neuronal growth factor listed in Table 12, or by upregulating, agonizing, or stabilizing a neuronal growth factor receptor listed in Table 12. In some embodiments, the neuronal growth factor modulator increases neurogenesis, axonogenesis or any of the processes mentioned above by stabilizing, agonizing, overexpressing, or upregulating a signaling protein encoded by a gene that is downstream of a neuronal growth factor. In some embodiments, the neuronal growth factor modulator increases neurogenesis, axonogenesis or any of the processes mentioned above by stabilizing, overexpressing, or upregulating a synaptic or structural protein. Neurogenesis, axonogenesis, neuronal growth, neuronal differentiation, neurite outgrowth, synapse formation, synaptic maturation, synaptic refinement, or synaptic stabilization can be increased in the subject at least 1%, 2%, 5%, 10%, 15%, 20%, 25%, 30%, 35%, 40%, 50%, 60%, 70%, 80% or more, compared to before the administration. Neurogenesis, axonogenesis, neuronal growth, neuronal differentiation, neurite outgrowth, synapse formation, synaptic maturation, synaptic refinement, or synaptic stabilization can be increased in the subject between 5-20%, between 5-50%, between 10-50%, between 20-80%, between 20-70%.

In some embodiments, the neuronal growth factor modulator decreases neurogenic/axonogenic signals, e.g., the method includes administering to the subject or contacting a cell with a neuronal growth factor modulator in an amount and for a time sufficient to decrease neurogenesis, axonogenesis, or innervation. For example, the neuronal growth factor modulator that leads to a decrease in neurogenesis or axonogenesis is a blocking or neutralizing antibody against a neurotrophic factor. Relevant neurotrophic factors include NGF, BDNF, ProNGF, Sortilin, TGFβ and TGFβ family ligands and receptors (e.g., TGFβR1, TGFβR2, TGFβ1, TGFβ2 TGFβ4), GFRα family ligands and receptors (e.g., GFRα1, GFRα2, GFRα3, GFRα4, GDNF), CNTF, LIF, neurturin, artemin, persephin, neurotrophin, chemokines, cytokines, and others listed in Table 12. Receptors for these factors can also be targeted, as well as downstream signaling pathways including Jak-Stat inducers, and cell cycle and MAPK signaling pathways. In some embodiments, the neuronal growth factor modulator decreases neurogenesis, axonogenesis or any of the processes mentioned above by sequestering, blocking, antagonizing, degrading, or downregulating a neuronal growth factor or a neuronal growth factor receptor listed in Table 12. In some embodiments, the neuronal growth factor modulator decreases neurogenesis, axonogenesis or any of the processes mentioned above by blocking or antagonizing a signaling protein that is downstream of a neuronal growth factor. In some embodiments, the neuronal growth factor modulator decreases neurogenesis, axonogenesis or any of the processes mentioned above by blocking, disrupting, or antagonizing a synaptic or structural protein. Neurogenesis, axonogenesis, neuronal growth, neuronal differentiation, neurite outgrowth, synapse formation, synaptic maturation, synaptic refinement, synaptic stabilization, or tissue innervation can be decreased in the subject at least 1%, 2%, 5%, 10%, 15%, 20%, 25%, 30%, 35%, 40%, 50%, 60%, 70%, 80% or more, compared to before the administration. Neurogenesis, axonogenesis, neuronal growth, neuronal differentiation, neurite outgrowth, synapse formation, synaptic maturation, synaptic refinement, synaptic stabilization, or tissue innervation can be decreased in the subject between 5-20%, between 5-50%, between 10-50%, between 20-80%, between 20-70%. Neuronal growth factor blockers can be administered in any of the modalities described herein (e.g., antibody, small molecule, nucleic acid, polypeptide, or viral vector).

In some embodiments, the neuronal growth factor modulator decreases the number of nerves in an affected tissue (e.g., a lymph node or site of inflammation). For example, the neuronal growth factor blocker is administered in an amount and for a time sufficient to decrease neurogenesis/axonogenesis.

Neuronal growth factor blockers include antibodies that bind to neuronal growth factors or neuronal growth factor receptors and decrease their signaling (e.g., blocking antibodies). Exemplary neuronal growth factor blocking antibodies are listed below in Table 13. Antibodies to neuronal growth factors listed in Table 12 can also be generated by those of skill in the art using well established and routine methods.

TABLE 12

NEURONAL GROWTH FACTORS

| Gene | Type | Accession Number | Entrez Gene ID |
|---|---|---|---|
| ARTN | Ligand | Q5T4W7 | 9048 |
| BDNF | Ligand | P23560 | 627 |
| BDNF-AS | Ligand | | 497258 |
| BEX1 | Signaling | Q9HBH7 | 55859 |
| BEX3 | Signaling | Q00994 | 27018 |
| CD34 | Receptor | P28906 | 947 |
| CDNF | Ligand | Q49AH0 | 441549 |
| CNTF | Ligand | P26441 | 1270 |
| CNTFR | Receptor | P26992 | 1271 |
| CRLF1 | Receptor | O75462 | 9244 |
| CSPG5 | Ligand | O95196 | 10675 |
| DCLK1 | Signaling | O15075 | 9201 |
| DISC1 | Signaling | Q9NRI5 | 27185 |
| DNAJC5 | Signaling | Q9H3Z4 | 80331 |
| DPYSL2 | Signaling | Q16555 | 1808 |
| DVL1 | Signaling | Q14640 | 1855 |
| EFNA5 | Ligand | P52803 | 1946 |
| EGR3 | Signaling | Q06889 | 1960 |
| ENO2 | Signaling | P09104 | 2026 |
| EphA1 | Receptor | P21709 | 2041 |
| EphA10 | Receptor | Q5JZY3 | 284656 |
| EphA2 | Receptor | P29317 | 1969 |
| EphA3 | Receptor | P29320 | 2042 |
| EphA4 | Receptor | P29317 | 2043 |
| EphA5 | Receptor | P54756 | 2044 |
| EphA6 | Receptor | Q9UF33 | 285220 |
| EphA7 | Receptor | Q15375 | 2045 |
| EphA8 | Receptor | P29322 | 2046 |
| EphB1 | Receptor | P54762 | 2047 |
| EphB2 | Receptor | P29323 | 2048 |

TABLE 12-continued

NEURONAL GROWTH FACTORS

| Gene | Type | Accession Number | Entrez Gene ID |
|---|---|---|---|
| EphB3 | Receptor | P54753 | 2049 |
| EphB4 | Receptor | P54760 | 2050 |
| EphB6 | Receptor | O15197 | 2051 |
| ETBR2 | Receptor | O60883 | 9283 |
| FSTL4 | Receptor | Q6MZW2 | 23105 |
| GDNF | Ligand | P39905 | 2668 |
| GFRA1 | Receptor | P56159 | 2674 |
| GFRA2 | Receptor | O00451 | 2675 |
| GFRA3 | Receptor | O60609 | 2676 |
| GFRA4 | Receptor | Q9GZZ7 | 64096 |
| GPR37 | Receptor | O15354 | 2861 |
| GPRIN1 | Signaling | Q7Z2K8 | 114787 |
| GPRIN2 | Signaling | O60269 | 9721 |
| GPRIN3 | Signaling | Q6ZVF9 | 285513 |
| GRB2 | Signaling | P62993 | 2885 |
| GZF1 | Signaling | Q9H116 | 64412 |
| IFNA1 | Ligand | P01562 | 3439 |
| IGF1 | Ligand | P05019 | 3479 |
| IGF2 | Ligand | P01344 | 3481 |
| IL11RA | Receptor | Q14626 | 3590 |
| IL1B | Ligand | P01584 | 3553 |
| IL3 | Ligand | P08700 | 3562 |
| IL4 | Ligand | P05112 | 3565 |
| IL6 | Ligand | P05231 | 3569 |
| IL6R | Receptor | P08887 | 3570 |
| IL6ST | Signaling | P40189 | 3572 |
| INS | Ligand | P01308 | 3630 |
| L1CAM | Signaling | P32004 | 3897 |
| LIF | Ligand | P15018 | 3976 |
| LIFR | Receptor | P42702 | 3977 |
| MAGED1 | Signaling | Q9Y5V3 | 9500 |
| MANF | Ligand | P55145 | 7873 |
| NDNF | Ligand | Q8TB73 | 79625 |
| NENF | Ligand | Q9UMX5 | 29937 |
| NENFP1 | Ligand | | 106480294 |
| NENFP2 | Ligand | | 100129880 |
| NENFP3 | Ligand | | 106481703 |
| NGF | Ligand | P01138 | 4803 |
| NGFR | Receptor | P08138 | 4804 |
| NRG1 | Ligand | Q02297 | 3084 |
| NRP1 | Receptor | O14786 | 8829 |
| NRTN | Ligand | Q99748 | 902 |
| NTF3 | Ligand | P20783 | 4908 |
| NTF4 | Ligand | P34130 | 4909 |
| NTRK1 | Receptor | P04629 | 4914 |
| NTRK2 | Receptor | Q16620 | 4915 |
| NTRK3 | Receptor | Q16288 | 4916 |
| PDPK1 | Signaling | O15530 | 5170 |
| PEDF | Ligand | P36955 | 5176 |
| PLEKHH3 | Signaling | Q7Z736 | 79990 |
| PSAP | Ligand | P07602 | 5660 |
| PSEN1 | Signaling | P49768 | 5663 |
| PSPN | Ligand | O70300 | 5623 |
| PTN | Ligand | P21246 | 5764 |
| RELN | Ligand | P78509 | 5649 |
| RET | Signaling | P07949 | 5979 |
| ROR1 | Receptor | Q01973 | 4919 |
| ROR2 | Receptor | Q01974 | 4920 |
| RPS6KA3 | Signaling | P51812 | 6197 |
| SDC3 | Receptor | O75056 | 9672 |
| SEMA3E | Ligand | O15041 | 9723 |
| SERPINE2 | Ligand | P07093 | 5270 |
| SERPINF1 | Ligand | P36955 | 5176 |
| SHC1 | Signaling | P51812 | 6464 |
| SNTG1 | Biosynthesis | P07602 | 54212 |
| SORCS1 | Receptor | O75056 | 114815 |
| SORCS2 | Receptor | O15041 | 57537 |
| SORCS3 | Receptor | P07093 | 22986 |
| SORT1 | Receptor | Q99523 | 6272 |
| SULF1 | Signaling | Q8IWU6 | 23213 |
| SULF2 | Signaling | Q8IWU5 | 55959 |
| TGFB1 | Ligand | P01137 | 7040 |
| TGFB2 | Ligand | P61812 | 7042 |
| TGFB3 | Ligand | P10600 | 7043 |
| TMEM158 | Receptor | Q8WZ71 | 25907 |
| TNF | Ligand | P01375 | 7124 |
| TPM3 | Receptor | P06753 | 7170 |
| VEGFA | Ligand | P15692 | 7422 |
| VEGFB | Ligand | P49765 | 7423 |
| VGF | Ligand | O15240 | 7425 |
| XCR1 | Receptor | P46094 | 2829 |
| ZN274 | Signaling | Q96G06 | 10782 |

TABLE 13

NEURONAL GROWTH FACTOR ANTIBODIES

| Neuronal Growth Factor | Antibody | Company |
|---|---|---|
| BDNF | 38B8 (agonist antibody) | Pfizer |
| BDNF | 29D7 (agonist antibody) | Pfizer |
| EphA3 | KB004 | KaloBios Pharmaceuticals, Inc. |
| IFNA1 | Faralimomab | Creative Biolabs |
| IFNA1 | Sifalimumab (MEDI-545) | MedImmune |
| IFNA1 | Rontalizumab | Genentech |
| IGF | Figitumumab (CP-751,871) - an IGR-1R MAb | Pfizer |
| IGF | SCH717454 (Robatumamab, inhibits IGF initiated phosphorylation) | Merck |
| IGF | Cixutumumab (IGF-1R antibody) | Eli Lilly |
| IGF | Teprotumumab (IGF-1R blocking antibody) | Genmab/Roche |
| IGF-2 | Dusigitumab | MedImmune/AstraZeneca |
| IGF-2 | DX-2647 | Dyax/Shire |
| IGF | Xentuzumab | Boehringer Ingelheim/Eli Lilly |
| IGF | Dalotuzumab (IGFR1 blocking antibody) | Merck & Co. |
| IGF | Figitumumab (IGFR1 blocking antibody) | Pfizer |
| IGF | Ganitumab (IGFR1 blocking antibody) | Amgen |
| IGF | Robatumumab (IGFR1 blocking antibody) | Roche/Schering-Plough |
| IL1B | Canakinumab | Novartis |
| IL1B | APX002 | Apexigen |
| IL1B | Gevokizumab | XOMA |
| IL4 | Pascolizumab | GlaxoSmithKline |
| IL4 | Dupilumab | Regeneraon/Sanofi |
| IL6 | Siltuximab | Janssen Biotech, Inc. |
| IL6 | Olokizumab | UCB/R-Pharm |
| IL6 | Elsilimomab | Orphan Pharma International |
| IL6 | Sirukumab | Centocor |
| IL6 | Clazakizumab | Bristol Myers Squib/Alder Biopharmaceuticals |
| IL6 | Gerilimzumab (ARGX-109) | arGEN-X/RuiYi |
| IL6 | FE301 | Ferring Pharmaceuticals |
| IL6 | FM101 | Femta Pharmaceuticals |
| IL-6R | Sarilumab (directed against IL6R) | Regeneron/Sanofi |
| IL-6R | Tocilizumab | Hoffmann-La Roche/Chugai |
| IL-6R | Sapelizumab | Chugai |
| IL-6R | Vobarilizumab | Ablynx |
| L1CAM | AB417 | Creative biolabs |
| L1CAM | L1-9.3 | Creative biolabs |
| L1CAM | L1-14.10 | Biolegend |
| NGF | Tanezumab | Pfizer |
| NGF | Fulranumab (JNJ-42160443), | Amgen |
| NGF | MNAC13 (anti-TrkA, the NGF receptor) | Creative Biolabs |
| NGF | mAb 911 | Rinat/Pfizer |
| NGF | Fasinumab | Regeneron/Teva |

TABLE 13-continued

NEURONAL GROWTH FACTOR ANTIBODIES

| Neuronal Growth Factor | Antibody | Company |
|---|---|---|
| NRG1 | 538.24 | Hoffman-La Roche |
| NRP1 | Vesencumab | Genentech/Roche |
| ROR1 | Cirmtuzumab | Oncternal Therapeutics |
| SAP | G5K2398852 | GlaxoSmithKline |
| TGFβ | Fresolimumab (pan-TGFβ antibody) | Genzyme/Aventis |
| TGFβ | IMC-TR1 (LY3022859) (MAb against TGFβRII) | Eli Lilly |
| TGFβ | T6M1 (anti-TGFβ1 MAb) | Eli Lilly |
| TGFβ2 | Lerdelimumab (CAT-152) | Genzyme |
| TGFβ1 | Metelimumab | Genzyme |
| TGFβ1 | LY2382770 | Eli Lilly |
| TGFβ | PF-03446962 (MAb against TGFβRI) | Pfizer |
| TNF | Infliximab | Janssen Biotech, Inc. |
| TNF | Adalimumab | AbbVie Inc. |
| TNF | Certolizumab pegol | UCB |
| TNF | Golimumab | Janssen Biotech, Inc. |
| TNF | Afelimomab | |
| TNF | Placulumab | Teva Pharmaceutical Industries, Inc. |
| TNF | Nerelimomab | Chiron/Celltech |
| TNF | Ozoralizumab | Pfizer/Ablynx |
| VEGFA | Bevacizumab | Genentech |
| VEGFA | Ranibizumab | Genentech |
| VEGF | Alacizumab pegol (anti-VEGFR2) | UCB |
| VEGFA | Brolucizumab | Novartis |
| VEGF | Icrucumab (anti-VEGFR1) | Eli Lilly |
| VEGF | Ramucirumab (anti-VEGFR2) | Eli Lilly |

Neuronal growth factor modulators also include agents that agonize or antagonize neuronal growth factors and neuronal growth factor receptors. For example, neuronal growth factor modulators include TNF inhibitors (e.g., etanercept, thalidomide, lenalidomide, pomalidomide, pentoxifylline, bupropion, and DOI), TGFβ1 inhibitors, (e.g., disitertide (P144)), TGFβ2 inhibitors (e.g., trabedersen (AP12009)). Exemplary neuronal growth factor agonists and antagonists are listed in Table 14.

TABLE 14

NEURONAL GROWTH FACTOR AGONISTS AND ANTAGONISTS

| | Agonist | Antagonist |
|---|---|---|
| TrkA | NGF, amitriptyline, and gambogic amide, gambogic acid | ALE-0540 |
| TrkB | BDNF, NT3, NT4, 3,7-Dihydroxyflavone, 3,7,8, 2'-Tetrahydroxyflavone, 4'-Dimethylamino-7,8-dihydroxyflavone, 7,3'-Dihydroxyflavone, 7,8-Dihydroxyflavone, 7,8,2'-Trihydroxyflavone, 7,8,3'-Trihydroxyflavone, Amitriptyline, Deoxygedunin, Diosmetin, HIOC, LM22A-4, N-Acetylserotonin, Norwogonin (5,7,8-THF), R7, LM22A4, and TDP6 | ANA-12, cyclotraxin B, and gossypetin |
| Pan-Trk receptor | | entrectinib (RXDX-101), AG 879, GNF 5837, GW 441756, and PF 06273340 |
| GFRα1R | GDNF and XIB4035 | |
| VEGF receptor | | AEE 788, AG 879, AP 24534, axitinib, DMH4, GSK 1363089, Ki 8751, RAF 265, SU 4312, SU 5402, SU 5416, SU 6668, sunitinib, toceranib, vatalanib, XL 184, ZM 306416, and ZM 323881 |
| TGFβRI | | galunisertib (LY2157299), TEW-7197, SB-431542, A 83-01, D 4476, GW 788388, LY 364947, R 268712, RepSox, SB 505124, SB 525334, and SD 208 |

In any of the combination therapy approaches described herein, the first and second therapeutic agent (e.g., a serotonin receptor activator described herein and the additional therapeutic agent) are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Diagnosis and Prognosis of Serotonin Receptor-Associated Inflammatory or Autoimmune Diseases or Conditions The methods described herein include methods of diagnosing or identifying patients with a serotonin receptor-associated inflammatory or autoimmune disease or condition. Subjects who can be diagnosed or identified as having a serotonin receptor-associated inflammatory or autoimmune disease or condition are subjects who have an inflammatory or autoimmune disease or condition (e.g., subjects identified as having an inflammatory or autoimmune disease or condition), or subjects suspected of having an inflammatory or autoimmune disease or condition. Subjects can be diagnosed or identified as having a serotonin receptor-associated inflammatory or autoimmune disease or condition based on screening of patient samples (e.g., immune cells collected from a subject, e.g., macrophages). Serotonin receptor expression (e.g., expression of one or more serotonin receptors listed in Table 1, e.g., HTR1F, HTR2B, HTR2C, HTR3A, HTR6, and/or HTR7) can be assessed in a sample of immune cells isolated from a subject using standard techniques known in the art, such as immunohistochemistry, western blot analysis, quantitative RT-PCR, RNA sequencing, fluorescent in situ hybridization, cDNA microarray, and droplet digital PCR. Serotonin receptor expression can be assessed by comparing measurements obtained from immune cells collected from a subject having or suspected of having an inflammatory or autoimmune disease or condition to measurements of serotonin receptor expression obtained from a reference sample (e.g., immune cells of the same type collected from a subject that does not have an inflammatory or autoimmune disease or condition or a cell that does not express serotonin receptor, e.g., a HEK cell). Reference samples can be obtained from healthy subjects (e.g., subjects without an inflammatory or autoimmune disease or condition), or they can be obtained from databases in which average measurements of serotonin receptor expression are cataloged for immune cells from healthy subjects (e.g., subjects without an inflammatory or autoimmune disease or condition).

Subjects are diagnosed or identified as having a serotonin receptor-associated inflammatory or autoimmune disease or condition if serotonin receptor expression (e.g., expression of one or more serotonin receptors listed in Table 1, e.g., HTR1F, HTR2B, HTR2C, HTR3A, HTR6, and/or HTR7) is decreased in the sample of immune cells from the subject compared to the reference sample. A decrease of serotonin receptor expression of 1.1-fold or more (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) in the sample isolated from the subject compared to the reference indicates that the subject has a serotonin receptor-associated inflammatory or autoimmune disease or condition. Subjects can also be diagnosed or identified as having a serotonin receptor-associated inflammatory or autoimmune disease or condition (e.g., an inflammatory or autoimmune disease or condition in which serotonin receptor is functional in immune cells) by contacting an immune cell isolated from the subject with a serotonin receptor antagonist and evaluating pro-inflammatory cytokine production (e.g., IL-8 secretion). An increase in pro-inflammatory cytokine production by 10% or more (e.g., 10%, 15%, 20%, 25%, 30%, 40%, 50%, 60%, 70%, 80%, 90%, 99%, or more) indicates that the immune cell expresses a functional serotonin receptor (e.g., the subject has a serotonin receptor-associated inflammatory or autoimmune disease or condition). Serotonin receptors can also be evaluated in vivo using radioligand labeling with PET/SPECT radioligands, such as those described in Paterson et al., Med Res Rev. 33:54, 2013. Subjects diagnosed or identified as having a serotonin receptor-associated inflammatory or autoimmune disease or condition can be treated with the methods and compositions described herein (e.g., serotonin receptor activators). Subjects with an autoimmune or inflammatory disease or condition can also be treated with the methods and compositions described herein if an immune cell from the subject (e.g., a macrophage) is found to express one or more serotonin receptors (e.g., expression of one or more serotonin receptors listed in Table 1, e.g., HTR1F, HTR2B, HTR2C, HTR3A, HTR6, and/or HTR7).

The methods described herein also include methods of predicting patient response (e.g., the response of an inflammatory or autoimmune disease or condition in a subject) to serotonin receptor activators in order to determine whether serotonin receptor activators can be used for treatment of an inflammatory or autoimmune disease or condition. In some embodiments, a sample (e.g., an immune cell or tissue sample) is isolated from a subject and contacted with one or more serotonin receptor activators or serotonin receptor-specific activators (e.g., samples are cultured and contacted with one or more activators in vitro). The response of the sample (e.g., immune cell or tissue sample) to the one or more serotonin receptor activators or serotonin receptor-specific activators is evaluated to predict response to treatment. Responses that are evaluated include immune cell migration, proliferation, recruitment, lymph node homing, lymph node egress, differentiation, activation, polarization, cytokine production, degranulation, maturation, ADCC, ADCP, antigen presentation, or immune cell serotonin receptor expression (e.g., expression of one or more serotonin receptors listed in Table 1, e.g., HTR1F, HTR2B, HTR2C, HTR3A, HTR6, and/or HTR7). A decrease of at least 5% or more (e.g., 5%, 10%, 15%, 20%, 25%, 30%, 40%, 50%, 60%, 70%, 80%, 90%, 99%, or more) in migration, proliferation, recruitment, lymph node egress, differentiation, activation, polarization, cytokine production (e.g., IL-8 production), degranulation, maturation, ADCC, ADCP, antigen presentation, or markers of inflammation in treated cells compared to untreated or control-treated cells, or an increase of at least 5% or more (e.g., 5%, 10%, 15%, 20%, 25%, 30%, 40%, 50%, 60%, 70%, 80%, 90%, 99%, or more) in lymph node homing or serotonin receptor expression in treated cells compared to untreated or control-treated cells indicates that the inflammatory or autoimmune disease or condition would respond to treatment with a serotonin receptor activator.

The methods used above to diagnose or identify a subject with a serotonin receptor-associated inflammatory or autoimmune disease or condition can also be used to predict patient response (e.g., the response of an inflammatory or autoimmune disease or condition in a subject) to treatment with a serotonin receptor activator. If the expression of one or more serotonin receptors (e.g., expression of one or more serotonin receptors listed in Table 1, e.g., HTR1F, HTR2B, HTR2C, HTR3A, HTR6, and/or HTR7) is decreased in an immune cell sample compared to a reference (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more lower in the inflammatory or autoimmune disease or condition sample compared to the reference), the subject can be predicted to respond to treatment with a serotonin receptor activator. Subjects predicted to respond to treatment with a serotonin receptor activator or serotonin receptor-specific activator can be treated using the methods and compositions described herein (e.g., serotonin receptor activators).

Methods of Treatment

Administration

An effective amount of a serotonin receptor activator described herein for treatment of inflammatory or autoimmune disease or condition can be administered to a subject by standard methods. For example, the agent can be administered by any of a number of different routes including, e.g., intravenous, intradermal, subcutaneous, percutaneous injection, oral, transdermal (topical), or transmucosal. The serotonin receptor activator can be administered orally or administered by injection, e.g., intramuscularly, or intravenously. The most suitable route for administration in any given case will depend on the particular agent administered, the patient, the particular disease or condition being treated, pharmaceutical formulation methods, administration methods (e.g., administration time and administration route), the patient's age, body weight, sex, severity of the diseases being treated, the patient's diet, and the patient's excretion rate. The agent can be encapsulated or injected, e.g., in a viscous form, for delivery to a chosen site, e.g., a lymph node or site of inflammation. The agent can be provided in a matrix capable of delivering the agent to the chosen site. Matrices can provide slow release of the agent and provide proper presentation and appropriate environment for cellular infiltration. Matrices can be formed of materials presently in use for other implanted medical applications. The choice of matrix material is based on any one or more of: biocompatibility, biodegradability, mechanical properties, and cosmetic appearance and interface properties. One example is a collagen matrix.

The agent (e.g., serotonin receptor activator, e.g., polypeptide, small molecule, nucleic acid, or antibody) can be incorporated into pharmaceutical compositions suitable for administration to a subject, e.g., a human. Such compositions typically include the agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a serotonin receptor activator described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers. These can be prepared according to methods known to those skilled in the art.

Nucleic acid molecule agents described herein can be administered directly (e.g., therapeutic mRNAs) or inserted into vectors used as gene therapy vectors. Gene therapy vectors can be delivered to a subject by, for example, intravenous injection, local administration (see U.S. Pat. No. 5,328,470) or by stereotactic injection (see, e.g., Chen et al., PNAS 91:3054 1994). The pharmaceutical preparation of the gene therapy vector can include the gene therapy vector in an acceptable diluent, or can include a slow release matrix in which the gene delivery vehicle is embedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of formulating pharmaceutical agents are known in the art, e.g., Niazi, Handbook of Pharmaceutical Manufacturing Formulations (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., Drug Delivery: Principles and Applications (Second Edition), Wiley 2016; formulation and delivery of peptide and protein agent is described, e.g., in Banga, Therapeutic Peptides and Proteins: Formulation, Processing, and Delivery Systems (Third Edition), CRC Press 2015.

Local Administration

The serotonin receptor activators described herein can be administered locally, e.g., to the site of inflammatory or autoimmune disease or condition in the subject. Examples of local administration include epicutaneous, inhalational, intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect. As an example, for the treatment of an inflammatory or autoimmune disease or condition described herein, the serotonin receptor activator may be administered locally (e.g., to or near a lymph node or lymphoid organ, a barrier tissue, a wound, gut, skin, airway, or spleen) in a compound-impregnated substrate such as a wafer, microcassette, or resorbable sponge placed in direct contact with the affected tissue. Alternatively, the serotonin receptor activator is infused into the brain or cerebrospinal fluid using standard methods. As another example, for a cardiac inflammatory or autoimmune disease or condition, the serotonin receptor activator may be delivered locally, for example, to the cardiac tissue (e.g., myocardium, pericardium, or endocardium) by direct intracoronary injection through the chest wall or using standard percutaneous catheter based methods. As yet another example, a pulmonary inflammatory or autoimmune disease or condition described herein (e.g., asthma) may be treated, for example, by administering the serotonin receptor activator locally by inhalation, e.g., in the form of an aerosol spray from a pressured container or dispenser which contains a suitable propellant, e.g., a gas such as carbon dioxide or a nebulizer. A serotonin receptor activator for use in the methods described herein can be administered to a lymph node. In certain embodiments, the agent is administered to a mucous membrane of the subject.

Combination Therapy

The serotonin receptor activators described herein may be administered in combination with one or more additional therapies (e.g., 1, 2, 3 or more additional therapeutic agents). The two or more agents can be administered at the same time (e.g., administration of all agents occurs within 15 minutes, 10 minutes, 5 minutes, 2 minutes or less). The agents can also be administered simultaneously via co-formulation. The two or more agents can also be administered sequentially, such that the action of the two or more agents overlaps and their combined effect is such that the reduction in a symptom, or other parameter related to the disorder is greater than what would be observed with one agent or treatment delivered alone or in the absence of the other. The effect of the two or more treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, local routes, and direct absorption through mucous membrane tissues. The therapeutic agents can be administered by the same route or by different routes. For example, a first therapeutic agent of the combination may be administered by intravenous injection while a second therapeutic agent of the combination can be administered locally in a compound-impregnated microcassette. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

For use in treating inflammatory and autoimmune related diseases or conditions, the second agent may be a disease-modifying anti-rheumatic drug (DMARD), a biologic response modifier (a type of DMARD), a corticosteroid, a nonsteroidal anti-inflammatory medication (NSAID). In some embodiments, the second agent is prednisone, prednisolone, methylprednisolone, methotrexate, hydroxycholorquine, sulfasalazine, leflunomide, cyclophosphamide, azathioprine, or a biologic such as tofacitinib, adalimumab, abatacept, anakinra, kineret, certolizumab, etanercept, golimumab, infliximab, rituximab or tocilizumab. For example, if the disease is RA, the second agent may be one or more of: prednisone, prednisolone and methylprednisolone, methotrexate, hydroxycholorquine, sulfasalazine, leflunomide, cyclophosphamide and azathioprine, tofacitinib, adalimumab, abatacept, anakinra, kineret, certolizumab, etanercept, golimumab, infliximab, rituximab or tocilizumab. In some embodiments, the second agent is 6-mercaptopurine, 6-thioguanine, abatacept, adalimumab, alemtuzumab (Lemtrada), aminosalicylates (5-aminoalicylic acid, sulfasalazine, mesalamine, balsalazide, olsalazine), antibiotics, anti-histamines, Anti-TNFα (infliximab, adalimumab, certolizumab pegol, natalizumab) Ustekinumab), azathioprine, belimumab, beta interferon, calcineurin inhibitors, certolizumab, corticosteroids (prednisone, methylprednisolone), cromolyn, cyclosporin A, cyclosporine, dimethyl fumarate (tecfidera), etanercept, fingolimod (Gilenya), fumaric acid esters, glatiramer acetate (Copaxone), golimumab, hydroxyurea, IFNγ, IL-11, infliximab, leflunomide, leukotriene receptor antagonist, long-acting beta2 agonist, methotrexate, mitoxantrone, mycophenolate mofetil, natalizumab (tysabri), NSAIDs, ocrelizumab, pimecrolimus, probiotics (VSL #3), retinoids, rituximab, salicylic acid, short-acting beta2 agonist, sulfasalazine, tacrolimus, teriflunomide (Aubagio), theophylline, tocilizumab, ustekinumab (anti-IL12/IL23), and vedolizumab (Anti alpha3 beta7 integrin).

Dosing

Subjects that can be treated as described herein are subjects with an inflammatory or autoimmune disease or condition or condition. The methods described herein may include a step of selecting a treatment for a patient. The method includes (a) identifying (e.g., diagnosing) a patient who has an inflammatory or autoimmune disease or condition, and (b) selecting a serotonin receptor activator, e.g., a serotonin receptor activator described herein, to treat the condition in the patient. In some embodiments, the method includes administering the selected treatment (e.g., an effective amount of a serotonin receptor activator) to the subject. In some embodiments, the subject has had denervation (e.g., surgical denervation or traumatic denervation such as from spinal cord injury).

In some embodiments, the method includes administering the selected treatment to the subject.

In some embodiments, the agent is administered in an amount and for a time effective to result in one of (or more, e.g., 2 or more, 3 or more, 4 or more of): (a) reduced auto-antibody levels, (b) reduced inflammation, (c)

increased organ function (d) reduced pain, (e) decreased rate or number of relapses or flare-ups of the disease, (f) increased quality of life.

The methods described herein can include profiling an immune cell to determine whether it expresses one or more serotonin receptors (e.g., one or more serotonin receptors listed in Table 1, e.g., HTR1F, HTR2B, HTR2C, HTR3A, HTR6, and/or HTR7). Profiling can be performed using RNA sequencing, microarray analysis, or serial analysis of gene expression (SAGE). Other techniques that can be used to assess serotonin receptor expression include quantitative RT-PCR. Profiling results can be confirmed using other methods such as immunohistochemistry, western blot analysis, flow cytometry, or southern blot analysis. Profiling results can be used to determine which serotonin receptor activator should be administered to treat the patient.

In some embodiments, a serotonin receptor activator administered according to the methods described herein does not have a direct effect on the central nervous system (CNS) or gut. Any effect on the CNS or gut is reduced compared to the effect observed if the serotonin receptor activator is administered directly to the CNS or gut. In some embodiments, direct effects on the CNS or gut are avoided by modifying the serotonin receptor activator not to cross the BBB, as described herein above, or administering the agent locally to a subject.

Subjects with an autoimmune/inflammatory disease or condition are treated with an effective amount of a serotonin receptor activator. The methods described herein also include contacting immune cells with an effective amount of a serotonin receptor activator. In some embodiments, an effective amount of a serotonin receptor activator is an amount sufficient to decrease the development of HEVs or TLOs, decrease immune cell (e.g., T cell, B cell, NK cell, ILC1, ILC2, ILC3, monocyte, macrophage (M1 and M2), dendritic cell, or antigen presenting cell) migration, decrease immune cell proliferation, decrease immune cell recruitment, increase immune cell lymph node homing, decrease immune cell lymph node egress, decrease immune cell differentiation, decrease immune cell activation, decrease immune cell polarization, decrease immune cell cytokine production, decrease immune cell degranulation, decrease immune cell maturation, decrease immune cell ADCC, decrease immune cell ADCP, decrease immune cell antigen presentation, reduce immune cell serotonin receptor expression, treat the autoimmune or inflammatory condition, reduce symptoms of an autoimmune or inflammatory condition, reduce inflammation, reduce auto-antibody levels, increase organ function, or decrease rate or number of relapses or flare-ups.

In some embodiments, the method includes administering the selected treatment to the subject.

In certain embodiments, a serotonin receptor activator administered according to the methods described herein does not have a direct effect on the central nervous system (CNS) or gut. Any effect on the CNS or gut is reduced compared to the effect observed if the serotonin receptor activator is administered directly to the CNS or gut. In some embodiments, direct effects on the CNS or gut are avoided by modifying the serotonin receptor activator not to cross the BBB, as described herein above, or administering the agent locally to a subject.

The methods described herein may also include a step of assessing the subject for a parameter of immune response, e.g., assessing the subject for one or more (e.g., 2 or more, 3 or more, 4 or more) of: Th2 cells, T cells, circulating monocytes, neutrophils, peripheral blood hematopoietic stem cells, macrophages, mast cell degranulation, activated B cells, NKT cells, macrophage phagocytosis, macrophage polarization, antigen presentation, immune cell activation, immune cell proliferation, immune cell lymph node homing or egress, T cell differentiation, immune cell recruitment, immune cell migration, lymph node innervation, dendritic cell maturation, HEV development, TLO development, or cytokine production. In embodiments, the method includes measuring a cytokine or marker associated with the particular immune cell type, as listed in Table 4 (e.g., performing an assay listed in Table 4 for the cytokine or marker). In some embodiments, the method includes measuring a chemokine, receptor, or immune cell trafficking molecule, as listed in Tables 5 and 6 (e.g., performing an assay to measure the chemokine, marker, or receptor). The assessing may be performed after the administration, before the first administration and/or during a course a treatment, e.g., after a first, second, third, fourth or later administration, or periodically over a course of treatment, e.g., once a month, or once every 3 months. In one embodiment, the method includes assessing the subject prior to treatment or first administration and using the results of the assessment to select a subject for treatment. In certain embodiments, the method also includes modifying the administering step (e.g., stopping the administration, increasing or decreasing the periodicity of administration, increasing or decreasing the dose of the serotonin receptor activator) based on the results of the assessment. For example, in embodiments where decreasing a parameter of immune response described herein is desired (e.g., embodiments where a decrease in Th2 cells is desired), the method includes stopping the administration if a marker of Th2 cells is not decreased at least 5%, 10%, 15%, 20%, 30%, 40%, 50% or more; or the method includes increasing the periodicity of administration if the marker of Th2 cells is not decreased at least 5%, 10%, 15%, 20% or more; or the method includes increasing the dose of the serotonin receptor activator if the marker of Th2 cells is not decreased at least 5%, 10%, 15%, 20% or more.

In certain embodiments, immune effects (e.g., immune cell activities) are modulated in a subject (e.g., a subject having an inflammatory or autoimmune condition) or in a cultured cell by at least 1%, 2%, 5%, 10%, 15%, 20%, 25%, 30%, 35%, 40%, 50%, 60%, 70%, 80%, compared to before an administration, e.g., of a dosing regimen, of a serotonin receptor activator such as those described herein. In certain embodiments, the immune effects are modulated in the subject or a cultured cell between 5-20%, between 5-50%, between 10-50%, between 20-80%, between 20-70%, between 50-100%, between 100-500%. The immune effects described herein may be assessed by standard methods:

The serotonin receptor activators described herein are administered in an amount (e.g., an effective amount) and for a time sufficient to effect one of the outcomes described above. The serotonin receptor activator may be administered once or more than once. The serotonin receptor activator may be administered once daily, twice daily, three times daily, once every two days, once weekly, twice weekly, three times weekly, once biweekly, once monthly, once bimonthly, twice a year, or once yearly. Treatment may be discrete (e.g., an injection) or continuous (e.g., treatment via an implant or infusion pump). Subjects may be evaluated for treatment efficacy 1 week, 2 weeks, 1 month, 2 months, 3 months, 4 months, 5 months, 6 months or more following administration of a serotonin receptor activator depending on the serotonin receptor activator and route of administration used for treatment. Depending on the outcome of the evaluation, treatment may be continued or ceased, treatment frequency or dosage may change, or the patient may be treated with a different serotonin receptor activator. Subjects may be treated for a discrete period of time (e.g., 1, 2, 3, 4, 5, 6, 7, 8, 9, 10, 11, or 12 months) or until the disease or condition is alleviated, or treatment may be chronic depending on the severity and nature of the disease or condition being treated.

Kits

The invention also features a kit containing (a) a pharmaceutical composition including a serotonin receptor activator described herein, and (b) instructions for administering the pharmaceutical composition to treat an inflammatory or autoimmune disease or condition.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1—Identification of Serotonin Receptor Expression in Macrophages

CD14+ monocytes were isolated from human PBMCs using negative magnetic bead selection (Stemcell Technologies) on day 0. Cells were cultured two days with M-CSF to differentiate monocytes to macrophages. On day 3, macrophages were polarized to M1-like macrophages with IFNγ and LPS; and M2-like macrophages with IL4, IL10, and TGFβ. Cells were harvested on day 6. The cells were lysed and RNA was extracted using an RNA extraction kit (Qiagen). qPCR was performed using integrated fluidic circuits (IFCs) run on a real-time PCR machine (Fluidigm) with primers specific for HTR2B, HTR2C, and HTR7 (Life Technologies). Gene expression was normalized to HPRT1. Expression level was calculated by 2^(−delta CT), where delta CT is (GOI Ct—HPRT Ct).

Gene expression for HTR2B and HTR7 in M1-like and M2-like macrophages was determined. Both HTR2B and HTR7 expression levels were higher on M1-like macrophages, as shown in Table 15 below.

TABLE 15

EXPRESSION OF SEROTONIN RECEPTORS IN M1- AND M2-LIKE MACROPHAGES

| Cell Type | Gene Name | Expression Level (Relative to HPRT1) |
|---|---|---|
| M1-like Macrophages | HTR2B (Entrez: 3357) | 0.7687 |
| M2-like Macrophages | HTR2B (Entrez: 3357) | 0.0177 |
| M1-like Macrophages | HTR7 (Entrez: 3363) | 0.0162 |
| M2-like Macrophages | HTR7 (Entrez: 3363) | 0.0068 |

Example 2—Examination of Target Expression in Immune Cells

The Immunological Genome Project (ImmGen) dataset of mouse immune cell gene expression (www.immgen.org) was examined for expression of serotonin receptors in different cell subsets. The expression data was generated by RNAseq on sorted mouse immune cells and quantified using the DESeq2 algorithm (Love et al., Genome Biology 15:550, 2014). The output of the DESeq2 algorithm was expression level, in arbitrary units, normalized to an internal factor derived from the sequencing depth of the sample.

Mouse cells were sorted from MC38 (C57BL6 murine colon adenocarcinoma cells) syngeneic tumors. Cells were sorted on an Aria sorter using the following markers: dendritic cells (CD45+ live CD19− CD3− CD11 b+CD11c+), neutrophils (CD45+ live CD19− CD3− CD11 b+Ly6c lo Ly6G hi), monocytes (CD45+ live CD19− CD3− CD11b+ Ly6c hi F4/80 lo), M2-like macrophages (CD45+ live CD19-CD3− CD11b+F4/80 hi). Cells were lysed and RNA was extracted using the RNeasy Mini Kit (Qiagen). RNA was submitted for Smart-Seq2 (Illumina). Median based normalization was performed with DESeq2.

HTR2B, HTR2C and HTR7 were found to be expressed on multiple types of myeloid lineage cells, including macrophages and dendritic cells, as shown in Table 16 below.

TABLE 16

EXPRESSION OF SEROTONIN RECEPTORS IN MOUSE IMMUNE CELLS

| Cell Type | Gene Name | Expression Level (Relative to HPRT1) |
|---|---|---|
| Splenic Dendritic Cells | HTR2B (Entrez: 3357) | 22.12 |
| Peritoneal Macrophages | HTR2B (Entrez: 3357) | 6.51 |
| Alveolar Macrophages | HTR2C (Entrez: 3358) | 12.87 |
| Alveolar Macrophages | HTR2C (Entrez: 3358) | 329.65 |
| Splenic Dendritic Cells | HTR7 (Entrez: 3363) | 229.74 |
| Tumor-infiltrating Dendritic Cells | HTR7 (Entrez: 3363) | 89.49 |
| Tumor-infiltrating M2 Macrophages | HTR7 (Entrez: 3363) | 114.87 |
| Tumor-infiltrating Monocytes | HTR7 (Entrez: 3363) | 122.35 |
| Tumor-infiltrating Neutrophils | HTR7 (Entrez: 3363) | 68.70 |

Example 3—Modulation of Serotonin Receptors with Serotonin Receptor Agonists Decreases IL8 Secretion in Immune Cells CD14+ monocytes were isolated from human PBMCs using negative magnetic bead selection (Stemcell Technologies) on day 0. Cells were cultured with M-CSF to differentiate monocytes to macrophages. On day 6, cells were treated with LP44 (high affinity 5-HT7 agonist), BW 723C86 hydrochloride (5-HT2B agonist), MK 212 hydrochloride (5-HT2C agonist) (Sigma-Aldrich), at concentrations 1 μM and 10 μM overnight. Supernatant was collected and bead-based immunoassays (Biolegend) were performed to detect changes in cytokine secretion.

Across multiple human donors, secretion of the inflammatory cytokine, IL8, by macrophages was decreased after addition of each of the HTR2B, HTR2C, and HTR7 agonists, as show in Table 17 below.

TABLE 17

IL-8 SECRETION BY MACROPHAGES INCUBATED WITH SEROTONIN RECEPTOR AGONISTS

| Sample | Fold change of IL-8 (Normalized to Macs + LPS with no compound treatment) |
|---|---|
| Macs alone | 1.00 |
| Macs + LP44 (1 μM) | 0.340 |
| Macs + LP44 (10 μM) | 0.427 |
| Macs + BW723086 (1 μM) | 0.693 |
| Macs + BW723086 (10 μM) | 0.527 |

TABLE 17-continued

IL-8 SECRETION BY MACROPHAGES INCUBATED
WITH SEROTONIN RECEPTOR AGONISTS

| Sample | Fold change of IL-8 (Normalized to Macs + LPS with no compound treatment) |
|---|---|
| Macs + MK212 (1 μM) | 0.502 |
| Macs + MK212 (10 μM) | 0.484 |

Example 4—Administration of a Serotonin Receptor Activator to Treat Local Intestinal Inflammation According to the methods disclosed herein, a physician of skill in the art can treat a patient, such as a human patient with an inflammatory condition (e.g., intestinal inflammation, such as inflammatory bowel disease (IBD), ulcerative colitis (UC), or Hirschsprung's disease-associated enterocolitis (HAEC)), so as to reduce the inflammation that contributes to the condition. Before treating the patient, a physician can perform an endoscopy or colonoscopy to diagnose a patient with intestinal inflammation, or identify a patient as having intestinal inflammation based on results from an endoscopy or colonoscopy. To treat the patient, a physician of skill in the art can administer to the human patient a serotonin receptor activator that decreases macrophage activation (e.g., an agent that increases serotonin receptor signaling, such as serotonin receptor-specific activating antibodies, e.g., an HTR1F, HTR2B, HTR2C, HTR3A, HTR6, or HTR7-specific activating antibody). The serotonin receptor-specific activating antibody can be administered parenterally (e.g., by subcutaneous injection or intravenous infusion) to treat intestinal inflammation. The serotonin receptor-specific activating antibody is administered in a therapeutically effective amount, such as from 10 μg/kg to 500 mg/kg (e.g., 10 μg/kg, 100 μg/kg, 500 μg/kg, 1 mg/kg, 10 mg/kg, 50 mg/kg, 100 mg/kg, 250 mg/kg, or 500 mg/kg). In some embodiments, the serotonin receptor-specific activating antibody is administered bimonthly, once a month, once every two weeks, or at least once a week or more (e.g., 1, 2, 3, 4, 5, 6, or 7 times a week or more).

The serotonin receptor-specific activating antibody decreases macrophage production of one or more pro-inflammatory cytokines (e.g., IL-8). The serotonin receptor-specific activating antibody is administered to the patient in an amount sufficient to decrease pro-inflammatory cytokine levels by 10% or more (e.g., 10%, 20%, 30%, 40%, 50%, 60%, 70%, 80%, 90%, 95% or more), or improve symptoms of intestinal inflammation (e.g., abdominal pain, diarrhea, fever, and fatigue). Cytokine production can be assessed by collecting a blood sample from the patient and evaluating one or more pro-inflammatory cytokines (e.g., IL-8). The blood sample can be collected one day or more after administration of the serotonin receptor-specific activating antibody (e.g., 1, 2, 3, 4, 5, 6, 7, 10, 14, 21, or 30 or more days after administration). The blood sample can be compared to a blood sample collected from the patient prior to administration of the serotonin receptor-specific activating antibody (e.g., a blood sample collected earlier the same day, 1 day, 1 week, 2 weeks, one month or more before administration of the serotonin receptor-specific activating antibody). A restoration in intestinal health as evaluated using a colonoscopy, endoscopy or tissue biopsy, reduction in the symptoms of intestinal inflammation (e.g., abdominal pain, diarrhea, fever, and fatigue), a reduction in the markers of intestinal inflammation in a blood sample (e.g., CRP, ESR, calprotectin, or lactoferrin, as compared to levels in a blood sample before treatment), reduced pro-inflammatory cytokine levels, or increased IL-10, TGFβ, Arg1, IDO, PF4, CCL24, or IL4R alpha indicate that the serotonin receptor-specific activating antibody reduces inflammation, decreases macrophage activation, or treats intestinal inflammation.

Example 5—Identification of Serotonin Receptors in T Cells

Naïve CD4+ and CD8+ T cells were isolated from human PBMCs using negative magnetic bead selection (Stemcell Technologies). Cells were activated with human CD3/CD28 T cell activator (StemCell). Cells were lysed and RNA was extracted (Qiagen).

RNA was sequenced at the Broad Technology Labs (BTL) at the Broad Institute using their Smart-Seq2 protocol, a protocol for full-length transcript sequencing from single cells. Smart-Seq2 libraries were sequenced on a high output sequence machine (Illumina) using a high out-put flow cell and reagent kit to generate 2×25 bp reads (plus dual index reads). Further details are available through the BTL, but in brief, reads were demultiplexed and aligned utilizing an ultrafast RNAseq alignment algorithm (Dobin et al., Bioinformatics. 29:15, 2013) with the following parameters:
—twopassMode Basic,
—alignIntronMax 1000000, —alignMatesGapMax 1000000, —sjdbScore 2, —quantMode TranscriptomeSAM, and —sjdbOverhang 24.

Quantification of individual read counts was performed using the DESeq2 algorithm (Love et al., Genome Biology 15:550, 2014), a method for differential analysis of count data, using shrinkage estimation for dispersions and fold changes to improve stability and interpretability of estimates. This enabled a more quantitative analysis focused on the strength rather than the mere presence of differential expression. The output of the DESeq2 algorithm was an expression level, in arbitrary units, normalized to an internal factor derived from the sequencing depth of the sample.

Gene expression for select serotonin receptors (HTRs) was detected in different T cell subsets, as shown in Table 18 below.

TABLE 18

HTR EXPRESSION IN T CELL SUBSETS

| Cell Type | Gene Name | Expression Level (DESeq2 normalized) |
|---|---|---|
| Human aCD3/aCD28 activated CD8+ T-Cells | HTR1E (Entrez: 3354) | 0.3 |
| Human Naïve CD8+ | HTR1F (Entrez: 3355) | 0.65 |
| Human Naïve CD4+ | HTR1F (Entrez: 3355) | 4.9 |
| Human aCD3/aCD28 activated CD8+ T-Cells | HTR1F (Entrez: 3355) | 0.39 |
| Human Naïve CD8+ | HTR2B (Entrez: 3357) | 1.2 |
| Human Naïve CD4+ | HTR2B (Entrez: 3357) | 0.75 |
| Human aCD3/aCD28 activated CD8+ T-Cells | HTR2B (Entrez: 3357) | 0.6 |
| Human aCD3/aCD28 activated CD4+ T-Cells | HTR2B (Entrez: 3357) | 0.42 |
| Human Naïve CD8+ | HTR3A (Entrez: 3359) | 0.97 |
| Human Naïve CD8+ | HTR6 (Entrez: 3362) | 1.07 |
| Human Naïve CD4+ | HTR6 (Entrez: 3362) | 3.98 |
| Human aCD3/aCD28 activated CD8+ T-Cells | HTR6 (Entrez: 3362) | 0.19 |

TABLE 18-continued

HTR EXPRESSION IN T CELL SUBSETS

| Cell Type | Gene Name | Expression Level (DESeq2 normalized) |
|---|---|---|
| Human aCD3/aCD28 activated CD4+ T-Cells | HTR6 (Entrez: 3362) | 0.74 |
| Human Naïve CD8+ | HTR7 (Entrez: 3363) | 0.93 |
| Human Naïve CD4+ | HTR7 (Entrez: 3363) | 0.56 |

Example 6—Evaluation of Serotonin Secretion by T Cells

CD8+ T cells were isolated from human PBMCs using negative magnetic bead selection (Stemcell Technologies) and cultured in T-Cell Expansion Media (StemCell). T cells were activated with Dynabeads Human T-Activator CD3/CD28 (Invitrogen) and 30 ng/mL recombinant human IL-2 (Peprotech) or left unactivated.

CD8+ T cells in culture were found to produce serotonin, as detected by ELISA (Novus Biologicals). When CD8+ T cells were activated, serotonin levels dropped. Because there was no other cellular source of serotonin in the culture, it seems that CD8+ T cells actively produced and released serotonin.

Serotonin levels in the cultures of human CD8+ T cells that were activated or left unactivated are shown in Table 19 below.

TABLE 19

SEROTONIN LEVELS IN MEDIA OF CD8+ T CELLS

| Culture conditions | Average serotonin level (nM) |
|---|---|
| Media Only | <0.01 |
| Unactivated CD8+ T-Cells: Donor 1 | 0.0497 |
| Activated CD8+ T-Cells: Donor 1 | <0.01 |
| Unactivated CD8+ T-Cells: Donor 2 | 5.14 |
| Activated CD8+ T-Cells: Donor 2 | 3.24 |

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

What is claimed is:

1. A method of reducing IL-8 expression in a subject in need thereof, comprising administering to the subject a serotonin receptor agonist in an amount effective to reduce IL-8 expression in the subject by at least 30%, relative to a control, wherein the method further comprises measuring an IL-8 expression level in the subject.

2. The method of claim 1, wherein the subject has psoriasis.

3. The method of claim 1, wherein the subject has rheumatoid arthritis.

4. The method of claim 1, wherein the method further comprises administering to the subject a second therapeutic agent.

5. The method of claim 4, wherein the second therapeutic agent is a disease-modifying anti-rheumatic drug (DMARD), a biologic response modifier, a corticosteroid, a nonsteroidal anti-inflammatory medication (NSAID), prednisone, prednisolone, methylprednisolone, methotrexate, hydroxycholorquine, sulfasalazine, leflunomide, cyclophosphamide, azathioprine, tofacitinib, adalimumab, abatacept, anakinra, kineret, certolizumab, etanercept, golimumab, infliximab, rituximab tocilizumab, an anti-viral compound, a nucleoside-analog reverse transcriptase inhibitor (NRTI), a non-nucleoside reverse transcriptase inhibitor (NNRTI), an anti-bacterial compound, an anti-fungal compound, an anti-parasitic compound, 6-mercaptopurine, 6-thioguanine, alemtuzumab, an aminosalicylate, an antibiotic, an antihistamine, an anti-TNFα agent, azathioprine, belimumab, beta interferon, a calcineurin inhibitor, certolizumab, cromolyn, cyclosporin A, cyclosporine, dimethyl fumarate, fingolimod, a fumaric acid ester, glatiramer acetate, hydroxyurea, IFNγ, IL-11, leflunomide, leukotriene receptor antagonist, long-acting beta2 agonist, mitoxantrone, mycophenolate mofetil, natalizumab, ocrelizumab, pimecrolimus, a probiotic, a retinoid, salicylic acid, short-acting beta2 agonist, sulfasalazine, tacrolimus, teriflunomide, theophylline, ustekinumab, vedolizumab, a serotonin receptor function activator, a neurotransmission modulator, a neuronal growth factor modulator, or a combination thereof.

6. The method of claim 1, wherein the serotonin receptor agonist is administered to the subject locally.

7. The method of claim 1, wherein the serotonin receptor agonist is administered to the subject systemically.

8. The method of claim 1, wherein the serotonin receptor agonist is LP44, BW 723C86, or MK-212.

9. The method of claim 8, wherein the serotonin receptor agonist is MK-212.

10. The method of claim 1, wherein the amount of the serotonin receptor agonist is effective to reduce IL-8 secretion by macrophages by at least 30%, relative to a control.

* * * * *